(12) United States Patent
Hartmann et al.

(10) Patent No.: US 7,776,344 B2
(45) Date of Patent: *Aug. 17, 2010

(54) METHODS RELATED TO IMMUNOSTIMULATORY NUCLEIC ACID-INDUCED INTERFERON

(75) Inventors: Gunther Hartmann, Munich (DE); Robert L. Bratzler, Concord, MA (US); Arthur M. Krieg, Wellesley, MA (US)

(73) Assignees: University of Iowa Research Foundation, Iowa City, IA (US); Coley Pharmaceutical GmbH, Dusseldorf (DE); Coley Pharmaceutical Group, Inc., New York, NY (US)

( * ) Notice: Subject to any disclaimer, the term of this patent is extended or adjusted under 35 U.S.C. 154(b) by 870 days.

This patent is subject to a terminal disclaimer.

(21) Appl. No.: 11/179,008

(22) Filed: Jul. 8, 2005

(65) Prior Publication Data

US 2006/0286070 A1     Dec. 21, 2006

Related U.S. Application Data

(63) Continuation of application No. 09/672,126, filed on Sep. 27, 2000, now Pat. No. 6,949,520.

(60) Provisional application No. 60/156,147, filed on Sep. 27, 1999.

(51) Int. Cl.
*A61K 47/00* (2006.01)
*A61K 31/70* (2006.01)
*C07H 21/02* (2006.01)

(52) U.S. Cl. .................. 424/278.1; 536/23.1; 514/44 R

(58) Field of Classification Search .................. None
See application file for complete search history.

(56) References Cited

U.S. PATENT DOCUMENTS

| | | | |
|---|---|---|---|
| 3,906,092 A | 9/1975 | Hilleman et al. |
| 4,469,863 A | 9/1984 | Ts'o et al. |
| 5,023,243 A | 6/1991 | Tullis |
| 5,248,670 A | 9/1993 | Draper et al. |
| 5,359,052 A | 10/1994 | Stec et al. |
| 5,512,668 A | 4/1996 | Stec et al. |
| 5,585,479 A | 12/1996 | Hoke et al. |
| 5,635,363 A | 6/1997 | Altman et al. |
| 5,663,153 A | 9/1997 | Hutcherson et al. |
| 5,723,335 A | 3/1998 | Hutcherson et al. |
| 5,786,189 A | 7/1998 | Locht et al. |
| 5,849,719 A | 12/1998 | Carson et al. |
| 5,856,465 A | 1/1999 | Stec et al. |
| 5,883,237 A | 3/1999 | Stec et al. |
| 6,194,388 B1 | 2/2001 | Krieg et al. |
| 6,207,646 B1 | 3/2001 | Krieg et al. |
| 6,214,804 B1 | 4/2001 | Felgner et al. |
| 6,214,806 B1 | 4/2001 | Krieg et al. |
| 6,218,371 B1 | 4/2001 | Krieg et al. |
| 6,221,882 B1 | 4/2001 | Macfarlane |
| 6,239,116 B1 | 5/2001 | Krieg et al. |
| 6,399,068 B1 | 1/2002 | Krieg et al. |
| 6,399,630 B1 | 6/2002 | Macfarlane |
| 6,406,705 B1 | 6/2002 | Davis et al. |
| 6,429,199 B1 | 8/2002 | Krieg et al. |
| 6,476,000 B1 | 11/2002 | Agrawal et al. |
| 6,479,504 B1 | 11/2002 | Macfarlane et al. |
| 6,521,637 B2 | 2/2003 | Macfarlane |
| 6,653,292 B1 | 11/2003 | Krieg et al. |
| 6,727,230 B1 | 4/2004 | Hutcherson et al. |
| 6,815,429 B2 | 11/2004 | Agrawal |
| 6,821,957 B2 | 11/2004 | Krieg et al. |
| 6,943,240 B2 | 9/2005 | Bauer et al. |
| 6,949,520 B1 | 9/2005 | Hartmann et al. |
| 7,001,890 B1 | 2/2006 | Wagner et al. |
| 7,105,495 B2 | 9/2006 | Agrawal et al. |
| 7,129,222 B2 | 10/2006 | Van Nest et al. |
| 7,223,741 B2 | 5/2007 | Krieg |
| 7,271,156 B2 | 9/2007 | Krieg et al. |
| 2002/0091097 A1 | 7/2002 | Bratzler et al. |
| 2002/0164341 A1 | 11/2002 | Davis et al. |
| 2002/0165178 A1 | 11/2002 | Schetter et al. |
| 2002/0198165 A1 | 12/2002 | Bratzler et al. |

(Continued)

FOREIGN PATENT DOCUMENTS

EP     0 092 574 A1     4/1983

(Continued)

OTHER PUBLICATIONS

Sequence alignment.*

(Continued)

*Primary Examiner*—Ileana Popa
(74) *Attorney, Agent, or Firm*—Wolf, Greenfield & Sacks, P.C.; Gregg C. Benson

(57) ABSTRACT

Methods and compositions are provided for extending the clinical utility of IFN-α in the treatment of a variety of viral and proliferative disorders. Among other aspects, the invention provides methods which increase the efficacy of IFN-α treatment and reduce IFN-α treatment-related side effects. In addition, methods are provided for supporting the survival and for activating natural interferon producing cells (IPCs) in vitro without exogenous IL-3 or GM-CSF. The invention is based on the discovery that certain CpG and non-CpG ISNAs promote survival and stimulation of IPCs.

9 Claims, 18 Drawing Sheets

U.S. PATENT DOCUMENTS

| | | |
|---|---|---|
| 2003/0026801 A1 | 2/2003 | Weiner et al. |
| 2003/0050261 A1 | 3/2003 | Krieg et al. |
| 2003/0050263 A1 | 3/2003 | Krieg et al. |
| 2003/0050268 A1 | 3/2003 | Krieg et al. |
| 2003/0055014 A1 | 3/2003 | Bratzler |
| 2003/0091599 A1 | 5/2003 | Davis et al. |
| 2003/0100527 A1 | 5/2003 | Krieg et al. |
| 2003/0104523 A1 | 6/2003 | Bauer et al. |
| 2003/0139364 A1 | 7/2003 | Krieg et al. |
| 2003/0148316 A1 | 8/2003 | Lipford et al. |
| 2003/0148976 A1 | 8/2003 | Krieg et al. |
| 2003/0166001 A1 | 9/2003 | Lipford |
| 2003/0181406 A1 | 9/2003 | Schetter et al. |
| 2003/0191079 A1 | 10/2003 | Krieg et al. |
| 2003/0212026 A1 | 11/2003 | Krieg et al. |
| 2003/0224010 A1 | 12/2003 | Davis et al. |
| 2003/0232074 A1 | 12/2003 | Lipford et al. |
| 2003/0232856 A1 | 12/2003 | Macfarlane |
| 2004/0009949 A1 | 1/2004 | Krieg |
| 2004/0030118 A1 | 2/2004 | Wagner et al. |
| 2004/0053880 A1 | 3/2004 | Krieg |
| 2004/0067902 A9 | 4/2004 | Bratzler et al. |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0092472 A1 | 5/2004 | Krieg |
| 2004/0106568 A1 | 6/2004 | Krieg et al. |
| 2004/0131628 A1 | 7/2004 | Bratzler et al. |
| 2004/0132677 A1 | 7/2004 | Fearon et al. |
| 2004/0132685 A1 | 7/2004 | Krieg et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | Davis et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0009774 A1 | 1/2005 | Krieg et al. |
| 2005/0032734 A1 | 2/2005 | Krieg et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0043529 A1 | 2/2005 | Krieg et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0070491 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0148537 A1 | 7/2005 | Krieg et al. |
| 2005/0169888 A1 | 8/2005 | Hartman et al. |
| 2005/0171047 A1 | 8/2005 | Krieg et al. |
| 2005/0181422 A1 | 8/2005 | Bauer et al. |
| 2005/0182017 A1 | 8/2005 | Krieg |
| 2005/0197314 A1 | 9/2005 | Krieg et al. |
| 2005/0215500 A1 | 9/2005 | Krieg et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250726 A1 | 11/2005 | Krieg et al. |
| 2005/0256073 A1 | 11/2005 | Lipford et al. |
| 2005/0267057 A1 | 12/2005 | Krieg |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1 | 1/2006 | Ahluwalia et al. |
| 2006/0019916 A1 | 1/2006 | Krieg et al. |
| 2006/0019923 A1 | 1/2006 | Davis et al. |
| 2006/0058251 A1 | 3/2006 | Krieg et al. |
| 2006/0089326 A1 | 4/2006 | Krieg et al. |
| 2006/0094683 A1 | 5/2006 | Krieg et al. |
| 2006/0140875 A1 | 6/2006 | Krieg et al. |
| 2006/0154890 A1 | 7/2006 | Bratzler et al. |
| 2006/0172966 A1 | 8/2006 | Lipford et al. |
| 2006/0188913 A1 | 8/2006 | Krieg et al. |
| 2006/0211639 A1 | 9/2006 | Bratzler et al. |
| 2006/0211644 A1 | 9/2006 | Krieg et al. |
| 2006/0223769 A1 | 10/2006 | Dow et al. |
| 2006/0229271 A1 | 10/2006 | Krieg et al. |
| 2006/0241076 A1 | 10/2006 | Uhlmann et al. |
| 2006/0246035 A1 | 11/2006 | Ahluwalia et al. |
| 2006/0287263 A1 | 12/2006 | Davis et al. |
| 2007/0009482 A9 | 1/2007 | Krieg et al. |
| 2007/0010470 A9 | 1/2007 | Krieg et al. |
| 2007/0037767 A1 | 2/2007 | Bratzler et al. |
| 2007/0049550 A1 | 3/2007 | Fearon et al. |
| 2007/0065467 A1 | 3/2007 | Krieg et al. |
| 2007/0066553 A1 | 3/2007 | Krieg et al. |
| 2007/0066554 A1 | 3/2007 | Krieg et al. |
| 2007/0078104 A1 | 4/2007 | Krieg et al. |
| 2007/0129320 A9 | 6/2007 | Davis et al. |
| 2007/0142315 A1 | 6/2007 | Forsbach et al. |
| 2007/0184465 A1 | 8/2007 | Wagner et al. |
| 2007/0202128 A1 | 8/2007 | Krieg et al. |
| 2007/0224210 A1 | 9/2007 | Krieg et al. |
| 2007/0232622 A1 | 10/2007 | Lipford et al. |
| 2008/0009455 A9 | 1/2008 | Krieg et al. |
| 2008/0026011 A1 | 1/2008 | Krieg et al. |
| 2008/0031936 A1 | 2/2008 | Krieg et al. |
| 2008/0045473 A1 | 2/2008 | Uhlmann et al. |
| 2008/0113929 A1 | 5/2008 | Lipford et al. |
| 2008/0226649 A1 | 9/2008 | Schetter et al. |

FOREIGN PATENT DOCUMENTS

| | | |
|---|---|---|
| EP | 0 302 758 A1 | 2/1989 |
| EP | 0 174 143 B1 | 11/1989 |
| EP | 0 468 520 A2 | 1/1992 |
| EP | 0 855 184 A1 | 7/1998 |
| EP | 0 772 619 B1 | 6/2006 |
| EP | 1 220 684 B1 | 7/2007 |
| WO | WO 96/02555 A1 | 1/1966 |

| WO | WO 91/12811 A1 | 9/1991 |
| --- | --- | --- |
| WO | WO 92/03456 | 3/1992 |
| WO | WO 92/18522 A1 | 10/1992 |
| WO | WO 92/21353 A1 | 12/1992 |
| WO | WO 94/19945 A1 | 9/1994 |
| WO | WO 95/05853 A1 | 3/1995 |
| WO | WO 95/26204 | 10/1995 |
| WO | WO 96/35782 A1 | 11/1996 |
| WO | WO 97/28259 A1 | 8/1997 |
| WO | WO 98/14210 A1 | 4/1998 |
| WO | WO 98/18810 A1 | 5/1998 |
| WO | WO 98/32462 A1 | 7/1998 |
| WO | WO 98/33517 A1 | 8/1998 |
| WO | WO 98/37919 A1 | 9/1998 |
| WO | WO 98/40100 A1 | 9/1998 |
| WO | WO 98/52581 A1 | 11/1998 |
| WO | WO 98/55495 A2 | 12/1998 |
| WO | WO 99/51259 A2 | 10/1999 |
| WO | WO 99/56755 A1 | 11/1999 |
| WO | WO 99/58118 A2 | 11/1999 |
| WO | WO 99/61056 A2 | 12/1999 |
| WO | WO 00/06588 A1 | 2/2000 |
| WO | WO 00/14217 A3 | 3/2000 |
| WO | WO 00/67023 A1 | 11/2000 |
| WO | WO 01/22972 A2 | 4/2001 |
| WO | WO 02/069369 A2 | 9/2002 |
| WO | WO 2004/007743 A2 | 1/2004 |
| WO | WO 2004/026888 A2 | 4/2004 |
| WO | WO 2004/094671 A2 | 11/2004 |

OTHER PUBLICATIONS

Altman et al., Phenotypic analysis of antigen-specific T lymphocytes. Science. Oct. 4, 1996;274(5284):94-6.

Azad et al., Antiviral activity of a phosphorothioate oligonucleotide complementary to RNA of the human cytomegalovirus major immediate-early region. Antimicrob Agents Chemother. Sep. 1993;37(9):1945-54.

Azuma et al., Biochemical and Immunological Studies on Cellular Components of Tubercle Bacilli. Kekkaku. 1992; 69(9):45-55.

Ballas et al., Induction of NK activity in murine and human cells by CpG motifs in oligodeoxynucleotides and bacterial DNA. J Immunol. Sep. 1, 1996;157(5):1840-5.

Banchereau et al., Dendritic cells and the control of immunity. Nature. Mar. 19, 1998;392(6673):245-52.

Bartholome et al., Interferon-beta induce the maturation of IL-12-deficient myeloid dendritic cells able to induce Th2 type cytokine secretion. J Interferon Cytokine Res. 1999; 19(Suppl 1): s81.

Beaucage et al., Deoxynucleoside phosphoramidites—A new class of key intermediates for deoxypolynucleotide synthesis. Tetrahedron Letts. 1981; 22(20):1859-62.

Bennett et al., DNA binding to human leukocytes. Evidence for a receptor-mediated association, internalization, and degradation of DNA. J Clin Invest. Dec. 1985;76(6):2182-90.

Blaxter et al., Genes expressed in *Brugia malayi* infective third stage larvae. Mol Biochem Parasitol. Apr. 1996;77(1):77-93.

Boggs et al., Characterization and modulation of immune stimulation by modified oligonucleotides. Antisense Nucleic Acid Drug Dev. Oct. 1997;7(5):461-71.

Branda et al., Immune stimulation by an antisense oligomer complementary to the rev gene of HIV-1. Biochem Pharmacol. May 25, 1993;45(10):2037-43.

Branda et al., Amplification of antibody production by phosphorothioate oligodeoxynucleotides. J Lab Clin Med. Sep. 1996;128(3):329-38.

Cascinu et al., A phase I trial of 5-fluorouracil, leucovorin and interferon-alpha 2b administered by 24 h infusion in metastatic colorectal carcinoma. Anticancer Drugs. Jul. 1996;7(5):520-4.

Cella et al., Plasmacytoid monocytes migrate to inflamed lymph nodes and produce large amounts of type 1 interferon. Nat Med. Aug. 1999;5(8):919-23.

Cella et al., Maturation, activation, and protection of dendritic cells induced by double-stranded RNA. J Exp Med. Mar. 1, 1999;189(5):821-9.

Chace et al., Bacterial DNA-induced NK cell IFN-gamma production is dependent on macrophage secretion of IL-12. Clin Immunol Immunopathol. Aug. 1997;84(2):185-93.

Chace et al., Regulation of differentiation in CD5+ and conventional B cells. Sensitivity to LPS-induced differentiation and interferon-gamma-mediated inhibition of differentiation. Clin Immunol Immunopathol. Sep. 1993;68(3):327-32.

Chang et al., The palindromic series I repeats in the simian cytomegalovirus major immediate-early promoter behave as both strong basal enhancers and cyclic AMP response elements. J Virol. Jan. 1990;64(1):264-77.

Chehimi et al., Dendritic cells and IFN-alpha-producing cells are two functionally distinct non-B, non-monocytic HLA-DR+ cell subsets in human peripheral blood. Immunology. Dec. 1989;68(4):486-90.

Chu et al., CpG oligodeoxynucleotides act as adjuvants that switch on T helper 1 (Th1) immunity. J Exp Med. Nov. 17, 1997;186(10):1623-31.

Cowdery et al., Bacterial DNA induces NK cells to produce IFN-gamma in vivo and increases the toxicity of lipopolysaccharides. J Immunol. Jun. 15, 1996;156(12):4570-5.

Crystal et al., Transfer of genes to humans: early lessons and obstacles to success. Science. Oct. 20, 1995;270(5235):404-10.

Deonarain et al., Ligand-targeted receptor-mediated vectors for gene delivery. Exp Opin Ther Pats. 1998; 8:53-69.

Englisch et al., Chemically modified oligonucleotides as probes and inhibitors. Angew. Chem. Int. Ed. Eng. Jun. 1991;30(6):613-29.

Erb et al., Infection of mice with *Mycobacterium bovis*-Bacillus Calmette-Guerin (BCG) suppresses allergen-induced airway eosinophilia. J Exp Med. Feb. 16, 1998;187(4):561-9.

Etlinger et al., Carrier sequence selection—one key to successful vaccines. Immunol Today. Feb. 1992;13(2):52-5.

Ferbas et al., CD4+ blood dendritic cells are potent producers of IFN-alpha in response to in vitro HIV-1 infection. J Immunol. May 1, 1994;152(9):4649-62. Abstract only.

Froehler et al., Synthesis of DNA via deoxynucleoside H-phosphonate intermediates. Nucleic Acids Res. Jul. 11, 1986;14(13):5399-407.

Gaffney et al., Large-scale oligonucleotide synthesis by the H-phosphonate method. Tetrahedron Letts. 1988; 29(22):2619-22.

Galy et al., Distinct signals control the hematopoiesis of lymphoid-related dendritic cells. Blood. Jan. 1, 2000;95(1):128-37.

Garegg et al., Nucleoside H-phosphonates. III. Chemical synthesis of oligodeoxyribonucleotides by the hydrogenphosphonate approach. Tetrahedron Letts. 1986; 27(34):4051-4.

Garegg et al., Nucleoside H-phosphonates. IV. Automated solid phase synthesis of oligoribonucleotides by the hydrogenphosphonate approach. Tetrahedron Lett. 1986; 27(34):4055-8.

Gill et al., Interferon-alpha maintenance therapy after cytotoxic chemotherapy for treatment of acquired immunodeficiency syndrome-related Kaposi's sarcoma. J Biol Response Mod. Oct. 1990;9(5):512-6.

Goeddel et al., The structure of eight distinct cloned human leukocyte interferon cDNAs. Nature. Mar. 5, 1981;290(5801):20-6.

Goodchild et al., Conjugates of oligonucleotides and modified oligonucleotides: a review of their synthesis and properties. Bioconjug Chem. May-Jun. 1990;1(3):165-87.

Gray et al., Expression of human immune interferon cDNA in *E. coli* and monkey cells. Nature. Feb. 11, 1982;295(5849):503-8.

Grouard et al., The enigmatic plasmacytoid T cells develop into dendritic cells with interleukin (IL)-3 and CD40-ligand. J Exp Med. Mar. 17, 1997;185(6):1101-11.

Gura et al., Antisense has growing pains. Science. Oct. 27, 1995;270(5236):575-7.

Halpern et al., In vitro inhibition of murine IFN gamma production by phosphorothioate deoxyguanosine oligomers. Immunopharmacology. Feb. 1995;29(1):47-52.

Halpern et al., Bacterial DNA induces murine interferon-gamma production by stimulation of interleukin-12 and tumor necrosis factor-alpha. Cell Immunol. Jan. 10, 1996;167(1):72-8.

Hartmann et al., CpG DNA and LPS induce distinct patterns of activation in human monocytes. Gene Ther. May 1999;6(5):893-903.

Hartmann et al., Mechanism and function of a newly identified CpG DNA motif in human primary B cells. J Immunol. Jan. 15, 2000;164(2):944-53.

Hartmann et al., Specific suppression of human tumor necrosis factor-alpha synthesis by antisense oligodeoxynucleotides. Antisense Nucleic Acid Drug Dev. 1996 Winter;6(4):291-9.

Hartmann et al., Delineation of a CpG phosphorothioate oligodeoxynucleotide for activating primate immune responses in vitro and in vivo. J Immunol. Feb. 1, 2000;164(3):1617-24.

Hartmann et al., CpG DNA: a potent signal for growth, activation, and maturation of human dendritic cells. Proc Natl Acad Sci U S A. Aug. 3, 1999;96(16):9305-10.

Hartmann et al., Spontaneous and cationic lipid-mediated uptake of antisense oligonucleotides in human monocytes and lymphocytes. J Pharmacol Exp Ther. May 1998;285(2):920-8.

Hatzfeld et al., Release of early human hematopoietic progenitors from quiescence by antisense transforming growth factor beta 1 or Rb oligonucleotides. J Exp Med. Oct. 1, 1991;174(4):925-9.

Highfield et al., Sepsis: the more, the murkier. Biotechnology (N Y). Aug. 1994;12(8):828.

Iguchi-Ariga et al., CpG methylation of the cAMP-responsive enhancer/promoter sequence TGACGTCA abolishes specific factor binding as well as transcriptional activation. Genes Dev. May 1989;3(5):612-9.

Iho et al., Oligodeoxynucleotides containing palindrome sequences with internal 5'-CpG-3' act directly on human NK and activated T cells to induce IFN-gamma production in vitro. J Immunol. Oct. 1, 1999;163(7):3642-52.

Ishikawa et al., IFN induction and associated changes in splenic leukocyte distribution. J Immunol. May 1, 1993;150(9):3713-27.

Iversen et al., Pharmacokinetics of an antisense phosphorothioate oligodeoxynucleotide against rev from human immunodeficiency virus type 1 in the adult male rat following single injections and continuous infusion. Antisense Res Dev. 1994 Spring;4(1):43-52.

Jakway et al., Growth regulation of the B lymphoma cell line WEHI-231 by anti-immunoglobulin, lipopolysaccharide, and other bacterial products. J Immunol. Oct. 1, 1986;137(7):2225-31.

Jaroszewski et al., Cellular uptake of antisense oligodeoxynucleotides. Advanced Drug Delivery Reviews. 1991;6:235-50.

Kataoka et al., Antitumor activity of synthetic oligonucleotides with sequences from cDNA encoding proteins of *Mycobacterium bovis* BCG. Jpn J Cancer Res. Mar. 1992;83(3):244-7.

Kimura et al., Binding of oligoguanylate to scavenger receptors is required for oligonucleotides to augment NK cell activity and induce IFN. J Biochem (Tokyo). Nov. 1994;116(5):991-4.

Klinman et al., Contribution of CpG motifs to the immunogenicity of DNA vaccines. J Immunol. Apr. 15, 1997;158(8):3635-9.

Klinman et al., CpG motifs present in bacteria DNA rapidly induce lymphocytes to secrete interleukin 6, interleukin 12, and interferon gamma. Proc Natl Acad Sci U S A. Apr. 2, 1996;93(7):2879-83.

Kranzer et al. CpG-oligodeoxynucleotides enhance T-cell receptor-triggered interferon-gamma production and up-regulation of CD69 via induction of antigen-presenting cell-derived interferon type I and interleukin-12. Immunology. Feb. 2000;99(2):170-8.

Krieg et al., Oligodeoxynucleotide modifications determine the magnitude of B cell stimulation by CpG motifs. Antisense Nucleic Acid Drug Dev. 1996 Summer;6(2):133-9.

Krieg et al., Phosphorothioate oligodeoxynucleotides: antisense or anti-protein? Antisense Res Dev. 1995 Winter;5(4):241.

Krieg et al., Applied Antisense Oligonucleotide Technology, 431-448, 1998.

Krieg, CpG DNA: a pathogenic factor in systemic lupus erythematosus? J Clin Immunol. Nov. 1995;15(6):284-92.

Krieg et al., CpG motifs in bacterial DNA trigger direct B-cell activation. Nature. Apr. 6, 1995;374(6522):546-9.

Krieg et al., Modification of antisense phosphodiester oligodeoxynucleotides by a 5' cholesteryl moiety increases cellular association and improves efficacy. Proc Natl Acad Sci U S A. Feb. 1, 1993;90(3):1048-52.

Krieg et al., The role of CpG dinucleotides in DNA vaccines. Trends Microbiol. Jan. 1998;6(1):23-7.

Krieg, An innate immune defense mechanism based on the recognition of CpG motifs in microbial DNA. J Lab Clin Med. Aug. 1996;128(2):128-33.

Krieg et al., A role for endogenous retroviral sequences in the regulation of lymphocyte activation. J Immunol. Oct. 15, 1989;143(8):2448-51.

Krieg et al., Uptake of oligodeoxyribonucleotides by lymphoid cells is heterogeneous and inducible. Antisense Res Dev. 1991 Summer;1(2):161-71.

Krieger et al., Structures and functions of multiligand lipoprotein receptors: macrophage scavenger receptors and LDL receptor-related protein (LRP). Annu Rev Biochem. 1994;63:601-37.

Kuramoto et al., Oligonucleotide sequences required for natural killer cell activation. Jpn J Cancer Res. Nov. 1992;83(II):1128-31.

Kuzel et al., Interferon alfa-2a combined with phototherapy in the treatment of cutaneous T-cell lymphoma. J Natl Cancer Inst. Feb. 7, 1990;82(3):203-7.

Lee et al., Effects of a hexameric deoxyriboguanosine run conjugation into CpG oligodeoxynucleotides on their immunostimulatory potentials. J Immunol. Oct. 1, 2000;165(7):3631-9.

Lipford et al., Poly-guanosine motifs costimulate antigen-reactive CD8 T cells while bacterial CpG-DNA affect T-cell activation via antigen-presenting cell-derived cytokines. Immunology. Sep. 2000;101(1):46-52.

Lipford et al., CpG-containing synthetic oligonucleotides promote B and cytotoxic T cell responses to protein antigen: a new class of vaccine adjuvants. Eur J Immunol. Sep. 1997;27(9):2340-4.

Lipford et al., Immunostimulatory DNA: sequence-dependent production of potentially harmful or useful cytokines. Eur J Immunol. Dec. 1997;27(12):3420-6.

Lipford et al., Bacterial DNA as immune cell activator. Trends Microbiol. Dec. 1998;6(12):496-500.

Lyons et al., Determination of lymphocyte division by flow cytometry. J Immunol Methods. May 2, 1994;171(1):131-7.

Macaya et al., Thrombin-binding DNA aptamer forms a unimolecular quadruplex structure in solution. Proc Natl Acad Sci U S A. Apr. 15, 1993;90(8):3745-9.

MacFarlane et al., Antagonism of immunostimulatory CpG-oligodeoxynucleotides by quinacrine, chloroquine, and structurally related compounds. J Immunol. Feb. 1, 1998;160(3):1122-31.

Manzel et al., CpG-oligodeoxynucleotide-resistant variant of WEHI 231 cells. J Leukoc Biol. Nov. 1999;66(5):817-21.

Martin et al., Effects of the ribavirin-interferon alpha combination on cultured peripheral blood mononuclear cells from chronic hepatitis C patients. Cytokine. Aug. 1998;10(8):635-44.

Mastrangelo et al., Gene therapy for human cancer: an essay for clinicians. Semin Oncol. Feb. 1996;23(1):4-21.

Matson et al., Nonspecific suppression of [3H]thymidine incorporation by "control" oligonucleotides. Antisense Res Dev. 1992 Winter;2(4):325-30.

McIntyre et al., A sense phosphorothioate oligonucleotide directed to the initiation codon of transcription factor NF-kappa B p65 causes sequence-specific immune stimulation. Antisense Res Dev. 1993 Winter;3(4):309-22.

Messina et al., Stimulation of in vitro murine lymphocyte proliferation by bacterial DNA. J Immunol. Sep. 15, 1991;147(6):1759-64.

Messina et al., The influence of DNA structure on the in vitro stimulation of murine lymphocytes by natural and synthetic polynucleotide antigens. Cell Immunol. Mar. 1993;147(1):148-57.

Miller et al., Targeted vectors for gene therapy. FASEB J. Feb. 1995;9(2):190-9.

Mojcik et al., Administration of a phosphorothioate oligonucleotide antisense to murine endogenous retroviral MCF env causes immune effects in vivo in a sequence-specific manner. Clin Immunol Immunopathol. May 1993;67(2):130-6.

Mottram et al., A novel CDC2-related protein kinase from *Leishmania mexicana*, LmmCRK1, is post-translationally regulated during the life cycle. J Biol Chem. Oct. 5, 1993;268(28):21044-52.

Nyce et al., DNA antisense therapy for asthma in an animal model. Nature. Feb. 20, 1997;385(6618):721-5.

O'Doherty et al., Dendritic cells freshly isolated from human blood express CD4 and mature into typical immunostimulatory dendritic cells after culture in monocyte-conditioned medium. J Exp Med. Sep. 1, 1993;178(3):1067-76.

Perera et al., A phase I pilot study of pelvic radiation and alpha-2A interferon in patients with locally advanced or recurrent rectal cancer. Int J Radiat Oncol Biol Phys. Jan. 15, 1997;37(2):297-303.

Pisetsky et al., The immunologic properties of DNA. J Immunol. Jan. 15, 1996;156(2):421-3.

Pisetsky et al., Stimulation of murine lymphocyte proliferation by a phosphorothioate oligonucleotide with antisense activity for herpes simplex virus. Life Sci. 1994;54(2):101-7.

Pisetsky, Immunologic consequences of nucleic acid therapy. Antisense Res Dev. 1995 Fall;5(3):219-25.

Pisetsky et al., Stimulation of in vitro proliferation of murine lymphocytes by synthetic oligodeoxynucleotides. Mol Biol Rep. Oct. 1993;18(3):217-21.

Pisetsky et al., The influence of base sequence on the immunological properties of defined oligonucleotides. Immunopharmacology. Nov. 1998;40(3):199-208.

Pulendran et al., Distinct dendritic cell subsets differentially regulate the class of immune response in vivo: Proc Natl Acad Sci U S A. Feb. 2, 1999;96(3):1036-41.

Qui et al., Treatment of cutaneous T cell lymphoma with low doses of interferon alpha-2b. Chin Med J (Engl). May 1996;109(5):404-6.

Ramanathan et al., Inhibition of interferon-gamma-induced major histocompatibility complex class I expression by certain oligodeoxynucleotides. Transplantation. Feb. 27, 1994;57(4):612-5.

Raz et al., Preferential induction of a Th1 immune response and inhibition of specific IgE antibody formation by plasmid DNA immunization. Proc Natl Acad Sci U S A. May 14, 1996;93(10):5141-5.

Rissoan et al., Reciprocal control of T helper cell and dendritic cell differentiation. Science. Feb. 19, 1999;283(5405):1183-6.

Roman et al., Immunostimulatory DNA sequences function as T helper-1-promoting adjuvants. Nat Med. Aug. 1997;3(8):849-54.

Sato et al., Immunostimulatory DNA sequences necessary for effective intradermal gene immunization. Science. Jul. 19, 1996;273(5273):352-4.

Schnell et al., Identification and characterization of a Saccharomyces cerevisiae gene (PAR1) conferring resistance to iron chelators. Eur J Biochem. Sep. 1, 1991;200(2):487-93.

Shirakawa et al., The inverse association between tuberculin responses and atopic disorder. Science. Jan. 3, 1997;275(5296):77-9.

Siegal et al., The nature of the principal type 1 interferon-producing cells in human blood. Science. Jun. 11, 1999;284(5421):1835-7.

Sparwasser et al., Macrophages sense pathogens via DNA motifs: induction of tumor necrosis factor-alpha-mediated shock. Eur J Immunol. Jul. 1997;27(7):1671-9.

Stec et al., Diastereomers of nucleoside 3'-O-(2-thio-1,3,2-oxathia(selena)phospholanes): building blocks for stereocontrolled synthesis of oligo(nucleoside phosphorothioate)s. J Am Chem Soc. 1995; 17:12019.

Stein et al., Oligodeoxynucleotides as inhibitors of gene expression: a review. Cancer Res. May 15, 1988;48(10):2659-68.

Stull et al., Antigene, ribozyme and aptamer nucleic acid drugs: progress and prospects. Pharm Res. Apr. 1995;12(4):465-83.

Subramanian et al., Theoretical considerations on the "spine of hydration" in the minor groove of d(CGCGAATTCGCG). d(GCGCTTAAGCGC): Monte Carlo computer simulation. Proc Natl Acad Sci U S A. Mar. 1988;85(6):1836-40.

Sun et al. Type I interferon-mediated stimulation of T cells by CpG DNA. J Exp Med. Dec. 21, 1998;188(12):2335-42.

Sun et al. Multiple effects of immunostimulatory DNA on T cells and the role of type I interferons. Springer Semin Immunopathol. 2000;22(1-2):77-84.

Tam et al., Ribavirin polarizes human T cell responses towards a Type 1 cytokine profile. J Hepatol: Mar. 1999;30(3):376-82.

Tam et al., The ribavirin analog ICN 17261 demonstrates reduced toxicity and antiviral effects with retention of both immunomodulatory activity and reduction of hepatitis-induced serum alanine aminotransferase levels. Antimicrob Agents Chemother. May 2000;44(5):1276-83.

Tanaka et al., An antisense oligonucleotide complementary to a sequence in 1 gamma 2b increases gamma 2b germline transcripts, stimulates B cell DNA synthesis, and inhibits immunoglobulin secretion. J Exp Med. Feb. 1, 1992;175(2):597-607.

Tanaka et al., Natural and synthetic non-peptide antigens recognized by human gamma delta T cells. Nature. May 11, 1995;375(6527):155-8.

Thomas et al., Human peripheral blood dendritic cell subsets. Isolation and characterization of precursor and mature antigen-presenting cells. J Immunol. Nov. 1, 1994;153(9):4016-28.

Tokunaga et al., A synthetic single-stranded DNA, poly(dG,dC), induces interferon-alpha/beta and -gamma, augments natural killer activity, and suppresses tumor growth. Jpn J Cancer Res. Jun. 1988;79(6):682-6.

Tokunaga et al., Synthetic oligonucleotides with particular base sequences from the cDNA encoding proteins of Mycobacterium bovis BCG induce interferons and activate natural killer cells. Microbiol Immunol. 1992;36(1):55-66.

Tokunaga et al., Antitumor activity of deoxyribonucleic acid fraction from Mycobacterium bovis BCG. I. Isolation, physicochemical characterization, and antitumor activity. J Natl Cancer Inst. Apr. 1984;72(4):955-62.

Trinchieri et al., Biology of natural killer cells. Adv Immunol. 1989;47:187-376.

Uhlmann et al., Antisense oligonucleotides: a new therapeutic principle. Chem Rev. Jun. 1990;90(4):543-84.

Vallin et al., Anti-double-stranded DNA antibodies and immunostimulatory plasmid DNA in combination mimic the endogenous IFN-alpha inducer in systemic lupus erythematosus. J Immunol. Dec. 1, 1999;163(11):6306-13.

Verma et al., Gene therapy—promises, problems, and prospects. Nature. Sep. 18, 1997;389:239-42.

Verthelyi et al., Human peripheral blood cells differentially recognize and respond to two distinct CPG motifs. J Immunol. Feb. 15, 2001;166(4):2372-7.

Wagner et al., Potent and selective inhibition of gene expression by an antisense heptanucleotide. Nat Biotechnol. Jul. 1996;14(7):840-4.

Wagner et al., Gene inhibition using antisense oligodeoxynucleotides. Nature. Nov. 24, 1994;372(6504):333-5.

Wallace et al., Oligonucleotide probes for the screening of recombinant DNA libraries. Methods Enzymol. 1987;152:432-42.

Wu et al., Receptor-mediated gene delivery and expression in vivo. J Biol Chem. Oct. 15, 1988;263(29):14621-4.

Wu-Pong et al., Oligonucleotides: opportunities for drug therapy and research. Pharm Technol. Oct. 1994;18:102-14.

Wyatt et al. Combinatorially selected guanosine-quartet structure is a potent inhibitor of human immunodeficiency virus envelope-mediated cell fusion. Proc Natl Acad Sci U S A. Feb. 15, 1994;91(4):1356-60.

Yamamoto et al., Lipofection of synthetic oligodeoxyribonucleotide having a palindromic sequence of AACGTT to murine splenocytes enhances interferon production and natural killer activity. Microbiol Immunol. 1994;38(10):831-6.

Yamamoto et al., Unique palindromic sequences in synthetic oligonucleotides are required to induce IFN [correction of INF] and augment IFN-mediated [correction of INF] natural killer activity. J Immunol. Jun. 15, 1992;148(12):4072-6.

Yamamoto et al., Ability of oligonucleotides with certain palindromes to induce interferon production and augment natural killer cell activity is associated with their base length. Antisense Res Dev. 1994 Summer;4(2):119-22.

Yamamoto et al., Synthetic oligonucleotides with certain palindromes stimulate interferon production of human peripheral blood lymphocytes in vitro. Jpn J Cancer Res. Aug. 1994;85(8):775-9.

Yamamoto et al., In vitro augmentation of natural killer cell activity and production of interferon-alpha/beta and -gamma with deoxyribonucleic acid fraction from Mycobacterium bovis BCG. Jpn J Cancer Res. Jul. 1988;79(7):866-73.

Yamamoto et al., DNA from bacteria, but not from vertebrates, induces interferons, activates natural killer cells and inhibits tumor growth. Microbiol Immunol. 1992;36(9):983-97.

Yamamoto et al., Mode of action of oligonucleotide fraction extracted from *Mycobacterium bovis* BCG. Kekkaku. 1994;69(9):29-32.

Yi et al., Rapid immune activation by CpG motifs in bacterial DNA. Systemic induction of IL-6 transcription through an antioxidant-sensitive pathway. J Immunol. Dec. 15, 1996;157(12):5394-402.

Yi et al., IFN-gamma promotes IL-6 and IgM secretion in response to CpG motifs in bacterial DNA and oligodeoxynucleotides. J Immunol. Jan. 15, 1996;156(2):558-64.

Zhao et al., Comparison of cellular binding and uptake of antisense phosphodiester, phosphorothioate, and mixed phosphorothioate and methylphosphonate oligonucleotides. Antisense Res Dev. 1993 Spring;3(1):53-66.

Zhao et al., Stage-specific oligonucleotide uptake in murine bone marrow B-cell precursors. Blood. Dec. 1, 1994;84(11):3660-6.

Zhong et al., Human blood dendritic cell-like B cells isolated by the 5G9 monoclonal antibody reactive with a novel 220-kDa antigen. J Immunol. Aug. 1, 1999;163(3):1354-62.

Krieg AM, Mechanisms and applications of immune stimulatory CpG oligodeoxynucleotides. *Biochim Biophys Acta*. Dec. 10, 1999;1489(1):107-16.

Krug A et al., Identification of CpG oligonucleotide sequences with high induction of IFN-alpha/beta in plasmacytoid dendritic cells. *Eur J Immunol*. Jul. 2001;31(7):2154-63.

Lottspeich F et al., *Bioanalytik*, Spektrum Akademischer Verlag, Heidelberg, 1998, pp. 945-951.

Bennett, Intracellular delivery of oligonucleotides with cationic liposomes. In: Delivery Strategies for Antisense Oligonucleotide Therapeutics. Akthar, Ed. 1995:223-32.

Coley Pharmaceutical, Press Release, "Coley Pharmaceutical Group Updates Hepatitis C Drug Strategy," Jan. 22, 2007.

Coley Pharmaceutical, Press Release, "Coley Pharmaceutical Group Announces Pfizer's Discontinuation of Clinical Trials for PF-3512676 Combined with Cytotoxic Chemotherapy in Advanced Non Small Cell Lung Cancer," Jun. 20, 2007.

Crooke et al., Phosphorothioate Oligonucleotides. Therapeut Apps. 1995;ch5:63-84.

Norman et al., Liposome-mediated, nonviral gene transfer induces a systemic inflammatory response which can exacerbate pre-existing inflammation. Gene Ther. 2000;7:1425-30.

Uhlmann, Recent advances in the medicinal chemistry of antisense oligonucleotides. Curr Opin Drug Discov Devel Mar. 29, 2000; 3(2):203-13.

Whitmore et al., LPD lipopolyplex initiates a potent cytokine response and inhibits tumor growth. Gene Ther. 1999;6:1867-75.

Zhao et al., Immunostimulatory activity of CpG containing phosphorothioate oligodeoxynucleotide is modulated by modification of a single deoxynucleoside. Bioorg Med Chem Lett. May 15, 2000;10(10):1051-4. Abstract Only.

\* cited by examiner

METHODS RELATED TO IMMUNOSTIMULATORY NUCLEIC ACID-INDUCED INTERFERON

RELATED APPLICATIONS

This application is a continuation of co-pending U.S. patent application Ser. No. 09/672,126 filed on Sep. 27, 2000, which claims benefit under 35 U.S.C. 119(e) to U.S. Provisional Patent Application No. 60/156,147, filed Sep. 27, 1999. The entire content of both these applications is incorporated herein by reference.

GOVERNMENT SUPPORT

Aspects of the invention have been made with government support under Grant No. CA 66570 awarded by the National Institutes of Health. The government may have certain rights in the invention.

SEQUENCE LISTING

This application includes a sequence listing submitted in duplicate on each of two compact discs. Each compact disc contains a 61 kB file, named C1039.70044US02seqlist.txt and created on Jul. 8, 2005, containing a copy of the sequence listing. The entire contents of the sequence listing submitted on compact disc is incorporated herein by reference.

BACKGROUND OF THE INVENTION

Human interferon alpha (IFN-α), also known as leukocyte interferon and a interferon, comprises a family of extracellular signaling proteins with antiviral, antiproliferative, and immunomodulatory activities. The first type of interferon to be identified and commercialized, IFN-α remains the most widely used interferon for clinical applications.

IFN-α is a member of the family of Type I interferons, which also includes IFN-β, omega (leukocyte (II)) interferon and tau (trophoblast) interferon. Omega and tau interferons are not clinically used. IFN-β, also known as fibroblast interferon, is well characterized but less utilized than IFN-α in the clinic. Fibroblasts are the predominant cellular producers of IFN-β. IFN-β has been approved in the United States for the treatment of relapsing forms of multiple sclerosis. Interferon gamma (IFN-γ), also known as gamma interferon, is the only known type II interferon. IFN-γ is produced by activated T lymphocytes and plays an important role in the establishment of a Th1 immune response. Its therapeutic use is limited. In the United States, human IFN-γ has been approved for reducing the frequency and severity of infections with chronic granulomatous disease.

IFN-α itself represents a family of more than a dozen related, homologous proteins (isoforms, Table 1), each encoded by a unique gene and each exhibiting a unique activity profile. The activities of the different α interferon species on viruses can vary as much as twenty-fold or more.

IFN-α products in clinical use are recombinant proteins or highly purified natural proteins of a single isoform. Recombinant IFN-α has been approved for use in the treatment of a variety of tumors and viral diseases (Table 2).

Until recently, B lymphocytes were believed to be the predominant producers of IFN-α. Recently a new cell type has been identified in the peripheral blood as the major source of Type I interferon production. These previously unidentified "natural interferon producing cells" (IPC) had been described for many years as a rare CD4+/MHC class II+ population (1:1000 within peripheral blood mononuclear cells (PBMC)) capable of synthesizing extremely large amounts of type I IFN upon viral infection. Cella M et al. *Nat Med* 5:919 (1999); Galy A et al. *Blood* 95:128 (2000); Siegal F P et al. *Science* 284:1835 (1999). After isolation of IPCs from the peripheral blood, IL-3 is required for survival of this cell type.

TABLE 1

Family of Human IFN-α

| | |
|---|---|
| IFN-αA | (IFN-α2a) |
| IFN-α2 | (IFN-α2b) |
| IFN-α4b | (IFN-α4) |
| IFN-αB2 | (IFN-α8) |
| IFN-αC | (IFN-α10) |
| IFN-αD | (IFN-α1) |
| IFN-αF | (IFN-α21) |
| IFN-αG | (IFN-α5) |
| IFN-αH2 | (IFN-α14) |
| IFN-αI | (IFN-α17) |
| IFN-αJ1 | (IFN-α7) |
| IFN-αK | (IFN-α6) |
| IFN-αM1 | |
| IFN-αN | |
| IFN-αWA | (IFN-α16) |

TABLE 2

Current Clinical Approval of IFN-α

| Approved in the United States | Approved Outside the United States |
|---|---|
| Chronic hepatitis B | Multiple myeloma |
| Chronic hepatitis C | Renal cell carcinoma |
| Hairy cell leukemia | Bladder cell carcinoma |
| Cutaneous T-cell leukemia | Colon carcinoma |
| Chronic myeloid leukemia | Cervical dysplasia |
| Non-Hodgkin's lymphoma | Laryngeal papillomatosis |
| Adjuvant therapy for malignant melanoma | |
| Kaposi's Sarcoma (AIDS-related) | |
| Condylomata acuminata (venereal warts) | |

Dendritic cells (DC) are thought to play a key role in the priming of immune responses against neoantigens. Banchereau J et al., *Nature* 392:245 (1998). Recent evidence suggests the presence of several distinct DC subtypes in human peripheral blood. Zhong R K et al. *J Immunol* 163:1254 (1999). These subtypes of DC include myeloid DC (mDC) and plasmacytoid DC (pDC, also known as DC2 cells). Precursor dendritic cells contain two subsets, a CD11c+/CD123+/− population (precursor of mDC) and a CD11c−/CD123++ population (precursor of pDC). The latter has recently attracted major attention since it was reported to be identical with the natural type I IFN producing cell (IPC). O'Doherty U et al. *J Exp Med* 178:1067 (1993); Grouard G et al. *J Exp Med* 185:1101 (1997); Thomas R et al. *J Immunol* 153:4016 (1994). Upon maturation this cell type develops characteristic features of DC. O'Doherty U et al. *J Exp Med* 178:1067 (1993); Thomas R et al. *J Immunol* 153:4016 (1994); Galy A et al. *Blood* 95:128 (2000); Chehimi J et al. *Immunology* 68:488. (1989).

The frequency of IPCs in PBMC in normal individuals varies between 0.2 and 0.6 percent. They are characterized by the absence of lineage markers CD3 (T cells), CD14 (monocytes), CD19 (B cells) and CD56 (NK cells), by the absence of CD11c, and by their expression of CD4, CD123 (IL-3 receptor α, IL-3Rα) and MHC class II. Grouard G et al. *J Exp Med* 185:1101-11 (1997); Rissoan M-C et al. *Science* 283:

1183-6 (1999); Siegal F P et al. *Science* 284:1835-7 (1999); Cella M et al. *Nat Med* 5:919-23 (1999). Morphologically IPCs resemble lymphocytes. IPCs can be isolated from PBMC by a combination of magnetic bead activated cell sorting (MACS) and fluorescence-activated cell sorting (flow cytometry, FACS). Without addition of IL-3, most of the IPCs die within 3 days of cell culture. Infection of IPCs with herpes simplex virus (HSV, Siegal F P et al. *Science* 284:1835-7 (1999)) or influenza virus (Cella M et al. *Nat Med* 5:919-23 (1999)) leads to production of large amounts of type I interferons as measured by a bioassay (protection of fibroblasts against vesicular stomatitis virus).

Aside from its role in carrying the genetic code, DNA has recently been shown to function as a signaling molecule (Krieg A M, 1998, *Biodrugs*). The immune systems of higher eukaryotes appear to have evolved a mechanism to detect prokaryotic nucleic acids based on their content of unmethylated CpG dinucleotides in particular base contexts. Krieg A M et al. *Nature* 374:546-9 (1995). Unmethylated CpG dinucleotides are common in bacterial DNA, but are underrepresented ("CpG suppression") and are methylated in vertebrate DNA. Bird A P *Trends in Genetics* 3:342 (1987). DNA containing these unmethylated CpG dinucleotides in immune stimulatory base contexts ("CpG motifs") triggers humoral immunity by inducing B cell activation, resistance to activation-induced apoptosis, and IL-6 and IgM secretion. Krieg A M et al. *Nature* 374:546-9 (1995); Yi A K et al. *J Immunol* 157:5394 (1996); and Klinman D et al. *Proc Natl Acad Sci USA* 93:2879 (1996). Such CpG DNA also directly activates monocytes and macrophage to secrete Th1-like cytokines. Ballas Z K et al. *J Immunol* 157:1840 (1996); Cowdery J S et al. *J Immunol* 156:4570 (1996); and Halpern M D et al. *Cell Immunol* 167:72 (1996). This leads to the activation of natural killer (NK) cell lytic activity and IFN-γ secretion. Ballas Z K et al. *J Immunol* 157:1840 (1996); Cowdery J S et al. *J Immunol* 156:4570 (1996); and Chace J H *Clin Immunol Immunopath* 84:185-93 (1997).

Yamamoto et al. reported in 1988 their findings that a nucleic acid fraction, designated MY-1, extracted from *Mycobacterium bovis* (BCG) induced type I interferon in vitro. Yamamoto S et al. *Jpn J Cancer Res* 79:866-73 (1988). Subsequently Tokunaga et al. subsequently synthesized a panel of 45-mer oligonucleotides with sequence present in cDNA encoding three randomly selected known BCG proteins and found that one sequence, BCG-A4, was a strong inducer of type I IFN in mouse spleen cell suspensions. Tokunaga T et al. *Microbiol Immunol* 36:55-66 (1992). A 5' 30-mer fragment, BCG-A4a, was reported to be as potent an inducer of IFN as the intact 45-mer BCG-A4.

```
BCG-A4
ACCGATGACGTCGCCGGTGACGGCACCACGACGG  (SEQ ID NO:163)
CCACCGTGCTG

BCG-A4a
ACCGATGACGTCGCCGGTGACGGCACCACG      (SEQ ID NO:164)
```

These workers went on to report that all oligonucleotides that induced IFN included a hexamer palindromic sequence GACGTC (present in BCG-A4 and BCG-A4a), AGCGCT, and AACGTT, but not ACCGGT. Yamamoto S et al. *J Immunol* 148:4072-6 (1992). Kimura et al. then found that among 30-mer phosophodiester oligodeoxynucleotides (ODNs) containing the hexamer palindrome AACGTT and oligoA, oligoC, oligoT, and oligoG ends, the latter (GGGGGGGGGGGGGAACGTTGGGGGGGGGGGGG; SEQ ID NO:165) was the strongest inducer of type I IFN in mouse spleen cell suspensions. Kimura Y et al. *J Biochem (Tokyo)* 116:991-4 (1994).

Recently it was surprisingly discovered that CpG ODN sequences with the strongest activity on human B cells did not induce detectable levels of type I IFN in PBMC. Hartmann G et al. *J Immunol* 164:1617-24 (2000).

SUMMARY OF THE INVENTION

It was discovered according to the invention that certain immunostimulatory nucleic acids (ISNAs) are especially suited as single agents to promote both survival and stimulation of IPCs. It was also discovered according to the invention that certain ISNAs obviate the requirement of IL-3 for IPC survival and the requirement of viral infection for IPC activation.

In addition, it was surprisingly discovered according to the invention that certain CpG ISNA induce the production of large amounts of type I IFN but have minimal effects activating B cells, while certain other CpG ISNA strongly activate human B cells and IPCs but have minimal effects inducing type I IFN. Surprisingly, it was discovered that the CpG ISNA that are strong inducers of type I IFN do not necessarily contain a hexamer palindrome GACGTC, AGCGCT, or AACGTT described by Yamamoto and colleagues. Yamamoto S et al. *J Immunol* 148:4072-6 (1992).

These discoveries open avenues for the use of ISNA, and especially certain CpG ISNA, as a therapeutic agent for clinical applications which call for the use of IFN-α. Clinical strategies comprise local and systemic in vivo administration of ISNA as well as ex vivo strategies in which in vitro ISNA-activated isolated IPCs are reinfused into the patient locally or systemically. These therapeutic strategies include the combination with other growth factors (IL-3, GM-CSF, flt3-ligand, etc.) as well as with other stimuli (superantigens, viral products). CpG ISNA of the invention that are inducers of type I IFN also allow the in vitro production of natural interferons using a permanent cell line derived from IPCs. Since natural IFN-α is a family of more than a dozen separate gene products, the individual products of which have unique activity profiles, the clinical use of natural interferon may be preferable compared to recombinant IFN-α derived from a single recombinant IFN-α gene.

It was also surprisingly discovered according to the invention that type I IFN activates a subset of T lymphocytes called γδ T cells. In addition, it was further discovered according to the invention that CpG ODN that are strong inducers of type I IFN, but not CpG ODN that are strong activators of B cells and pDCs without being strong inducers of type I IFN, can activate γδ T cells present within a population of peripheral blood mononuclear cells (PBMCs). Without meaning to be held to a particular theory, it appears likely that type I IFN-inducing CpG ODN can activate γδ T cells present within the PBMC by their ability to induce secretion of type I IFN by IPCs also present in the PBMC.

In addition to the ability to activate γδ T cells, it was also surprisingly discovered according to the invention that type I IFN-inducing CpG ODN, but not CpG ODN that are strong activators of B cells and pDCs without being strong inducers of type I IFN, can enhance proliferation of antigen-activated γδ T cells present within a population of PBMCs. In particular, proliferation is enhanced in connection with the presence of specific nonpeptide antigen, for example, the phosphoantigen isopentenyl pyrophosphate (IPP).

It was also surprisingly discovered according to the invention that certain CpG ODN in combination with IPP synergistically induce the production of IFN-γ and perforin in γδ T cells.

In another surprising discovery according to the invention, it was found that type I IFN-inducing CpG ODN, but not CpG ODN that are strong activators of B cells and pDCs without being strong inducers of type I IFN, can block CD40-stimulated IL-12 production in PBMC. It was surprisingly found, in addition, that CpG ODN that are strong activators of B cells and pDCs without being strong inducers of type I IFN had the opposite effect, i.e., these ODN actually enhanced CD40-stimulated IL-12 production in PBMC.

It was further discovered according to the invention that that CpG ODN that are strong activators of B cells and pDCs without being strong inducers of type I IFN are better promoters of antigen-specific priming and recall of human cytotoxic T lymphocytes (CTLs) than are CpG ODN that are potent inducers of type I IFN.

According to one aspect of the invention, an improvement is provided for therapies involving administration of IFN-α to subjects. The improvement involves co-administering an effective amount of an isolated ISNA. In one embodiment, the IFN-α is administered at the clinically established effective dose for IFN-α alone. In another embodiment, the IFN-α is administered at a dosage below the clinically established effective dose for IFN-α alone. The IFN-α also can be administered at the maximum tolerated dose for IFN-α in the absence of the oligonucleotide. In other embodiments, the IFN-α is administered at 20 percent below, 30 percent below, 40 percent below, or even 50 percent below the maximum tolerated dose of IFN-α or the clinically established effective dose for IFN-α alone.

In some embodiments, the ISNA is a CpG nucleic acid. In other embodiments the ISNA is a non-CpG nucleic acid, i.e., the ISNA is not a CpG nucleic acid. The non-CpG nucleic acid in one embodiment is a T-rich nucleic acid. In another embodiment the non-CpG nucleic acid is a poly-G nucleic acid. In yet another embodiment the immunostimulatory nucleic acid is any combination of at least two nucleic acids selected from the group including CpG nucleic acids, T-rich nucleic acids, and poly-G nucleic acids.

In some embodiments, the ISNA is modified. In certain embodiments, the ISNA has a modified backbone with at least one nuclease-resistant internucleotide linkage. A nuclease-resistant internucleotide linkage can be selected from the group which includes a phosphorothioate linkage, a phosphorodithioate linkage, a methylphosphonate linkage, and a peptide linkage. In certain embodiments a modified ISNA includes at least one nucleotide analog or at least one nucleotide analog. The ISNA is a palindrome in certain embodiments, while in other embodiments, the ISNA is not a palindrome. In some preferred embodiments the ISNA is between 8 and 100 nucleotides in length, while in other preferred embodiments the ISNA is between 12 and 40 nucleotides in length. Preferred sizes, sequences and modifications are described in greater detail below.

In certain preferred embodiments the ISNA is a chimeric CpG ODN exemplified by formula 5' $Y_1N_1CGN_2Y_2$ 3' wherein $Y_1$ and $Y_2$ are, independent of one another, nucleic acid molecules having between 1 and 10 nucleotides, and wherein $Y_1$ includes at least one modified internucleotide linkage; $Y_2$ includes at least one modified internucleotide linkage; and $N_1$ and $N_2$ are nucleic acid molecules, each independent of one another, having between 0 and 20 nucleotides and in some embodiments, between 3 and 8 nucleotides, but wherein $N_1CGN_2$ has at least 6 nucleotides in total and wherein the nucleotides of $N_1CGN_2$ have a phosphodiester backbone.

In certain preferred embodiments the ISNA has a sequence corresponding to

| Sequence | ODN | SEQ ID |
|---|---|---|
| ggGGTCAACGTTGAggggggG | ODN 1585 | SEQ ID NO:1 |
| tcgtcgttttgtcgttttgtcgtt | ODN 2022 | SEQ ID NO:2 |
| ggggtcgtcgttttgggggg | ODN 2184 | SEQ ID NO:3 |
| tcgtcgttttgtcgttttggggggg | ODN 2185 | SEQ ID NO:4 |
| ggggtcgacgtcgagggggg | ODN 2192 | SEQ ID NO:5 |
| ggggtcatcgatgagggggg | ODN 2204 | SEQ ID NO:6 |
| ggGGGACGATCGTCgggggG | ODN 2216 | SEQ ID NO:7 |
| ggggggtcgtacgacgggggg | ODN 2217 | SEQ ID NO:8 |
| ggGGGACGATATCGTCggggG | ODN 2245 | SEQ ID NO:9 |
| ggGGGACGACGTCGTCggggG | ODN 2246 | SEQ ID NO:10 |
| ggGGGACGAGCTCGTCggggG | ODN 2247 | SEQ ID NO:11 |
| ggGGGACGTACGTCggggG | ODN 2248 | SEQ ID NO:12 |
| ggGGGACGATCGTTGggggG | ODN 2252 | SEQ ID NO:13 |
| ggGGAACGATCGTCgggggG | ODN 2253 | SEQ ID NO:14 |
| ggGGGGACGATCGTCgggggG | ODN 2254 | SEQ ID NO:15 |
| ggGGGACGATCGTCgggggG | ODN 2255 | SEQ ID NO:16 |
| ggGGGTCATCGATGAggggG | ODN 2260 | SEQ ID NO:17 |
| ggGGTCGTCGACGAggggGG | ODN 2293 | SEQ ID NO:18 |
| ggGGTCGTTCGAACGAggggG | ODN 2294 | SEQ ID NO:19 |
| ggGGACGTTCGAACGTggggG | ODN 2295 | SEQ ID NO:20 |
| ggGGAACGACGTCGTTggggG | ODN 2297 | SEQ ID NO:21 |
| ggGGAACGTACGTCggggG | ODN 2298 | SEQ ID NO:22 |
| ggGGAACGTACGTACGTTggggG | ODN 2299 | SEQ ID NO:23 |
| ggGGTCACCGGTGAggggG | ODN 2300 | SEQ ID NO:24 |
| ggGGTCGACGTACGTCGAggggG | ODN 2301 | SEQ ID NO:25 |
| ggGGACCGGTACCGGTgggggG | ODN 2302 | SEQ ID NO:26 |
| ggGTCGACGTCGAggggGG | ODN 2303 | SEQ ID NO:27 |
| ggGGTCGACGTCGaggggg | ODN 2304 | SEQ ID NO:28 |
| ggGGAACGTTAACGTTggggG | ODN 2305 | SEQ ID NO:29 |
| ggGGACGTCGACGTgggggG | ODN 2306 | SEQ ID NO:30 |
| ggGGGTCGTTCGTTgggggG | ODN 2311 | SEQ ID NO:31 |
| ggGACGATCGTCGggggGG | ODN 2328 | SEQ ID NO:32 |
| ggGTCGTCGACGAgggggG | ODN 2329 | SEQ ID NO:33 |
| ggTCGTCGACGAGgggggG | ODN 2330 | SEQ ID NO:34 |

-continued

```
ggGGACGATCGTCGggggG       ODN 2332, SEQ ID NO:35 ggGGTCGACGTCGACGTCGAGggggG ODN 2334, SEQ ID NO:36
and ggGGACGACGTCGTGggggG      ODN 2336, SEQ ID NO:37
``` wherein each lower case letter represents phosphorothioate linkage and each upper case letter indicates phosphodiester linkage.

In certain more preferred embodiments the ISNA has a sequence corresponding to

```
ggGGGACGAGCTCGTCggggG,    (ODN 2247; SEQ ID NO:11)

ggGGGACGATCGTCggggG,      (ODN 2255; SEQ ID NO:16)

ggGGACGTTCGAACGTggggG,    (ODN 2295; SEQ ID NO:20)

ggGGTCGACGTCGACGTCGAGgg   (ODN 2334; SEQ ID NO:36)
gggG,
or ggGGACGACGTCGTGggggG,     (ODN 2336; SEQ ID NO:37)
``` wherein each lower case letter represents phosphorothioate linkage and each upper case letter indicates phosphodiester linkage.

In one embodiment, the improvement further involves co-administering granulocyte-monocyte colony-stimulating factor (GM-CSF) to the subject.

In another embodiment, the subject has a condition selected from the group consisting of a proliferative disorder and a viral infection. In one embodiment, the subject has a proliferative disorder such as hairy cell leukemia, chronic myelogenous leukemia, cutaneous T-cell leukemia, multiple myeloma, follicular lymphoma, malignant melanoma, squamous cell carcinoma, AIDS-related Kaposi's sarcoma, renal cell carcinoma, prostate carcinoma, bladder cell carcinoma, cervical dysplasia, and colon carcinoma. In another embodiment the subject has a viral infection such as hepatitis B, hepatitis C, condyloma acuminatum, human immunodeficiency virus, herpes, cytomegalovirus, Epstein-Barr virus, and papillomavirus.

According to another aspect of the invention, a method is provided for supplementing IFN-α treatment of a subject. This aspect of the invention involves administering to a subject in need of IFN-α treatment an effective amount of IFN-α and an ISNA of the invention. The IFN-α doses, ISNAs, concurrent therapy, and conditions calling for treatment with IFN-α according to this aspect of the invention are the same as those described above.

According to another aspect of the invention, a method is provided for treating a subject to activate IPCs of the subject. The method involves isolating IPCs from the subject in need of such treatment, culturing the isolated IPCs in vitro, contacting the IPCs in vitro with an effective amount of an isolated ISNA, and returning the contacted cells to the subject. The cells can also be contacted in vitro with a growth factor or with a cytokine. In one embodiment, the method further involves contacting the IPC cells in vitro with IL-3 or GM-CSF. In another embodiment, the cells are cultured in vitro in the absence of IL-3 and/or GM-CSF. The ISNAs and conditions calling for treatment with IFN-α according to this aspect of the invention are as described above.

According to another aspect of the invention, a method is provided for increasing the efficacy of IFN-α treatment of a subject. The method involves administering to a subject in need of treatment with IFN-α a pharmaceutical composition including IFN-α and co-administering to the subject a pharmaceutical composition including an ISNA in an amount which, together with the administered IFN-α, is an effective IFN-α treatment. The efficacy of the IFN-α treatment is greater than the efficacy of administering the same amount of IFN-α in the absence of co-administering the ISNA. The ISNAs and conditions calling for treatment with IFN-α according to this aspect of the invention are as described above. In one embodiment, the pharmaceutical compositions are administered locally.

According to another aspect of the invention, a method is provided for decreasing the dose of IFN-α needed for effective treatment of a subject. The method involves administering to a subject in need of treatment with IFN-α a pharmaceutical composition comprising IFN-α and co-administering to the subject a pharmaceutical composition including an ISNA. The amount of administered IFN-α is less than an amount of IFN-α required to achieve the same therapeutic benefit in the absence of co-administering the ISNA. In certain embodiments, the amount of administered IFN-α is at least 20 percent, at least 30 percent, at least 40 percent, or even at least 50 percent below the amount of IFN-α required in the absence of coadministering the immunostimulatory nucleic acid. The pharmaceutical composition including the ISNA can be administered locally. The ISNAs and conditions calling for treatment with IFN-α according to this aspect of the invention are as described above.

According to another aspect of the invention, a method is provided for preventing an IFN-α treatment-related side effect in a subject receiving or in need of treatment with IFN-α. The method involves administering to a subject in need of the treatment an IFN-α pharmaceutical composition and a pharmaceutical composition comprising an immunostimulatory nucleic acid in an amount which, together with the administered IFN-α, is an effective IFN-α treatment. The IFN-α treatment-related side effect is reduced in comparison to the side effect when IFN-α is administered in the absence of co-administering ISNA. The IFN-α treatment-related side effect may be systemic. The IFN-α treatment-related side effect prevented by the method can include any one of flu-like syndrome, fever, headache, chills, myalgia, fatigue, anorexia, nausea, vomiting, diarrhea, and depression. The pharmaceutical composition including the ISNA can be administered locally. The ISNAs and conditions calling for treatment with IFN-α according to this aspect of the invention are as described above.

According to another aspect of the invention, a method is provided for enhancing the efficacy of IFN-α treatment in a subject in need of such treatment. The method involves administering to a subject in need of such treatment an effective amount of a pharmaceutical composition containing IFN-α for treating the condition, isolating natural IFN-producing cells from a donor, contacting the isolated IFN-producing cells ex vivo with an amount of an ISNA effective for inducing the IFN-producing cells to release IFN-α, and administering the contacted cells to the subject. The donor can be, but does not have to be, the subject. The method further can comprise contacting the isolated cells with an antigen. The administration of the cells can be accomplished in any manner suitable for the purposes of the method, and can include local injection. The local injection can be via a blood vessel supplying a target tissue. The blood vessel can be selected from, among others, hepatic artery, portal vein, celiac artery, and splenic artery. The ISNAs and conditions calling for treatment with IFN-α according to this aspect of the invention are as described above.

According to another aspect of the invention, a method is provided for supporting survival of IPCs in vitro. The method involves isolating such cells from a subject, culturing the cells in a sterile medium suitable for tissue culture, and contacting the cells in vitro with an amount of ISNA effective to support the growth of the cells in the absence of IL-3. In a preferred embodiment the cells can be precursor type 2 dendritic cells. The culture conditions also can be selected to be free of IL-3 and/or free of GM-CSF, or they can include IL-3, GM-CSF, or other growth factors and cytokines. Preferred ISNAs, including oligonucleotides, sequences, modifications and the like according to this aspect of the invention, are as described above.

According to another aspect of the invention, a method is provided for stimulating isolated IPCs in vitro. The method involves isolating such cells from a subject, culturing the cells in a sterile medium suitable for tissue culture, and contacting the cells in vitro with an amount of ISNA effective to induce secretion of at least one type I interferon or the expression of CD 80. The culture conditions can be in the presence or absence of interleukin-3, GM-CSF, or other growth factors and cytokines. The IPCs can be precursor type 2 dendritic cells. Preferred ISNAs, including oligonucleotides, sequences, modifications and the like according to this aspect of the invention, are as described above.

According to another aspect of the invention, a method is provided for stimulating the production of an array of at least 3, 4, 5, 6, 7 or even 8 or more interferon sub-types. The method involves contacting IFN-producing cells with an ISNA. The cells may or may not be isolated. The contacting may be in vivo or in vitro. Preferred ISNAs, including oligonucleotides, sequences, modifications and the like according to this aspect of the invention, are as described herein.

According to another aspect of the invention, a method is provided for inhibiting IL-12 production. The method involves contacting IL-12-producing cells, in the presence of interferon-producing cells under conditions in which the IL-12-producing cells normally produce IL-12, with an immunostimulatory nucleic acid in an amount effective for inducing secretion of type I interferon. In certain embodiments the immunostimulatory nucleic acid includes at least one of SEQ ID NO:1-37.

According to yet another aspect of the invention, a method for activating γδ T cells is provided. In one embodiment the method involves contacting γδ T cells with type I IFN. In another embodiment the method involves contacting γδ T cells within a population of cells that includes interferon-producing cells with an immunostimulatory nucleic acid in an amount effective for inducing type I IFN.

In another aspect the invention provides a method for promoting the proliferation of γδ T cells. The method involves contacting a γδ T cell with an immunostimulatory nucleic acid and an inducer of γδ T cell proliferation, in an amount effective to induce a greater proliferative response in the presence of the immunostimulatory nucleic acid than in its absence. In certain embodiments the immunostimulatory nucleic acid is a CpG nucleic acid. In preferred embodiments the immunostimulatory nucleic acid is selected from among SEQ ID NO:1-37. The inducer of γδ T cell proliferation in some embodiments is a phosphoantigen, preferably IPP.

In another aspect the invention provides an isolated nucleic acid having a sequence selected from the group which includes:

| Sequence | ODN | SEQ ID |
|---|---|---|
| tcgtcgttttgtcgttttgtcgtt | ODN 2022 | SEQ ID NO:2 |
| ggggtcgtcgttttgggggg | ODN 2184 | SEQ ID NO:3 |
| tcgtcgttttgtcgttttgggggg | ODN 2185 | SEQ ID NO:4 |
| ggggtcgacgtcgagggggg | ODN 2192 | SEQ ID NO:5 |
| ggggtcatcgatgagggggg | ODN 2204 | SEQ ID NO:6 |
| ggGGGACGATCGTCgggggG | ODN 2216 | SEQ ID NO:7 |
| gggggtcgtacgacgggggg | ODN 2217 | SEQ ID NO:8 |
| ggGGGACGATATCGTCgggggG | ODN 2245 | SEQ ID NO:9 |
| ggGGGACGACGTCGTCgggggG | ODN 2246 | SEQ ID NO:10 |
| ggGGGACGAGCTCGTCgggggG | ODN 2247 | SEQ ID NO:11 |
| ggGGGACGTACGTCgggggG | ODN 2248 | SEQ ID NO:12 |
| ggGGGACGATCGTTgggggG | ODN 2252 | SEQ ID NO:13 |
| ggGGAACGATCGTCgggggG | ODN 2253 | SEQ ID NO:14 |
| ggGGGGACGATCGTCgggggG | ODN 2254 | SEQ ID NO:15 |
| ggGGGACGATCGTCGgggggG | ODN 2255 | SEQ ID NO:16 |
| ggGGGTCATCGATGAgggggG | ODN 2260 | SEQ ID NO:17 |
| ggGGTCGTCGACGAgggggG | ODN 2293 | SEQ ID NO:18 |
| ggGGTCGTTCGAACGAgggggG | ODN 2294 | SEQ ID NO:19 |
| ggGGACGTTCGAACGTgggggG | ODN 2295 | SEQ ID NO:20 |
| ggGGAACGACGTCGTTgggggG | ODN 2297 | SEQ ID NO:21 |
| ggGGAACGTACGTCgggggG | ODN 2298 | SEQ ID NO:22 |
| ggGGAACGTACGTACGTTgggggG | ODN 2299 | SEQ ID NO:23 |
| ggGGTCACCGGTGAgggggG | ODN 2300 | SEQ ID NO:24 |
| ggGGTCGACGTACGTCGAgggggG | ODN 2301 | SEQ ID NO:25 |
| ggGGACCGGTACCGGTgggggG | ODN 2302 | SEQ ID NO:26 |
| ggGTCGACGTCGAgggggG | ODN 2303 | SEQ ID NO:27 |
| ggGGTCGACGTCGaggggg | ODN 2304 | SEQ ID NO:28 |
| ggGGAACGTTAACGTTgggggG | ODN 2305 | SEQ ID NO:29 |
| ggGGACGTCGACGTgggggG | ODN 2306 | SEQ ID NO:30 |
| ggGGGTCGTTCGTTgggggG | ODN 2311 | SEQ ID NO:31 |
| ggGACGATCGTCGgggggG | ODN 2328 | SEQ ID NO:32 |
| ggGTCGTCGACGAgggggggG | ODN 2329 | SEQ ID NO:33 |
| ggTCGTCGACGAGgggggG | ODN 2330 | SEQ ID NO:34 |
| ggGGACGATCGTCGgggggG | ODN 2332 | SEQ ID NO:35 |
| ggGGTCGACGTCGACGTCGAgggggG and | ODN 2334, | SEQ ID NO:36 |
| ggGGACGACGTCGTgggggG | ODN 2336, | SEQ ID NO:37 | wherein each lower case letter represents phosphorothioate linkage and each upper case letter indicates phosphodiester linkage.

In yet another aspect the invention provides a pharmaceutical composition containing an isolated nucleic acid having a sequence selected from the group which includes:

| | | |
|---|---|---|
| tcgtcgttttgtcgttttgtcgtt | ODN 2022 | SEQ ID NO:2 |
| ggggtcgtcgttttggggggg | ODN 2184 | SEQ ID NO:3 |
| tcgtcgttttgtcgttttgggggg | ODN 2185 | SEQ ID NO:4 |
| ggggtcgacgtcgagggggg | ODN 2192 | SEQ ID NO:5 |
| ggggtcatcgatgagggggg | ODN 2204 | SEQ ID NO:6 |
| ggGGGACGATCGTCgggggG | ODN 2216 | SEQ ID NO:7 |
| gggggtcgtacgacgggggg | ODN 2217 | SEQ ID NO:8 |
| ggGGGACGATATCGTCgggggG | ODN 2245 | SEQ ID NO:9 |
| ggGGGACGACGTCGTCgggggG | ODN 2246 | SEQ ID NO:10 |
| ggGGGACGAGCTCGTCgggggG | ODN 2247 | SEQ ID NO:11 |
| ggGGGACGTACGTCgggggG | ODN 2248 | SEQ ID NO:12 |
| ggGGGACGATCGTTgggggG | ODN 2252 | SEQ ID NO:13 |
| ggGGAACGATCGTCgggggG | ODN 2253 | SEQ ID NO:14 |
| ggGGGGACGATCGTCgggggG | ODN 2254 | SEQ ID NO:15 |
| ggGGGACGATCGTCGgggggG | ODN 2255 | SEQ ID NO:16 |
| ggGGGTCATCGATGAgggggG | ODN 2260 | SEQ ID NO:17 |
| ggGGTCGTCGACGAgggggG | ODN 2293 | SEQ ID NO:18 |
| ggGGTCGTTCGAACGAgggggG | ODN 2294 | SEQ ID NO:19 |
| ggGGACGTTCGAACGTgggggG | ODN 2295 | SEQ ID NO:20 |
| ggGGAACGACGTCGTTgggggG | ODN 2297 | SEQ ID NO:21 |
| ggGGAACGTACGTCgggggG | ODN 2298 | SEQ ID NO:22 |
| ggGGAACGTACGTACGTTgggggG | ODN 2299 | SEQ ID NO:23 |
| ggGGTCACCGGTGAgggggG | ODN 2300 | SEQ ID NO:24 |
| ggGGTCGACGTACGTCGAgggggG | ODN 2301 | SEQ ID NO:25 |
| ggGGACCGGTACCGGTgggggG | ODN 2302 | SEQ ID NO:26 |
| ggGTCGACGTCGAgggggG | ODN 2303 | SEQ ID NO:27 |
| ggGGTCGACGTCGaggggg | ODN 2304 | SEQ ID NO:28 |
| ggGGAACGTTAACGTTgggggG | ODN 2305 | SEQ ID NO:29 |
| ggGGACGTCGACGTgggggG | ODN 2306 | SEQ ID NO:30 |
| ggGGGTCGTTCGTTgggggG | ODN 2311 | SEQ ID NO:31 |
| ggGACGATCGTCGgggggG | ODN 2328 | SEQ ID NO:32 |
| ggGTCGTCGACGAgggggGG | ODN 2329 | SEQ ID NO:33 |
| ggTCGTCGACGAGgggggG | ODN 2330 | SEQ ID NO:34 |
| ggGGACGATCGTCGgggggG | ODN 2332 | SEQ ID NO:35 |
| ggGGTCGACGTCGACGTCGAGgggggG and | ODN 2334, | SEQ ID NO:36 |
| ggGGACGACGTCGTGgggggG | ODN 2336, | SEQ ID NO:37 | wherein each lower case letter represents phosphorothioate linkage and each upper case letter indicates phosphodiester linkage, plus a pharmaceutically acceptable carrier. In some embodiments the pharmaceutical composition also contains IFN-α.

According to another aspect of the invention, an interferon composition for administration to a subject is provided. The composition includes interferon in a container for administration to a subject. The amount of the interferon in the container is at least about 10 percent less than the maximum tolerated dose (MTD). Preferably the amount of interferon in the container is at least about 20 percent below the MTD, at least 30 percent below the MTD, at least 40 percent below the MTD, or even at least 50 percent below the MTD. The container also can include an ISNA.

In still another aspect of the invention, kits for administration of interferon and an ISNA to a subject are provided. The kits include a container containing a composition which includes IFN-α and instructions for administering the interferon to a subject in need of such treatment in an amount which is at least about 10 percent less than the MTD, 20 percent less than the MTD, 30 percent less than the MTD, 40 percent less than the MTD, or 50 percent less than the MTD. The kit can include, in the same container or in a separate container, an ISNA. The kit also can include instructions for treating a subject with a condition susceptible to treatment with IFN-α.

Each of the limitations of the invention can encompass various embodiments of the invention. It is, therefore, anticipated that each of the limitations of the invention involving any one element or combinations of elements can be included in each aspect of the invention.

These and other aspects of the invention are described in greater detail below.

DETAILED DESCRIPTION OF THE INVENTION

Figure 1:
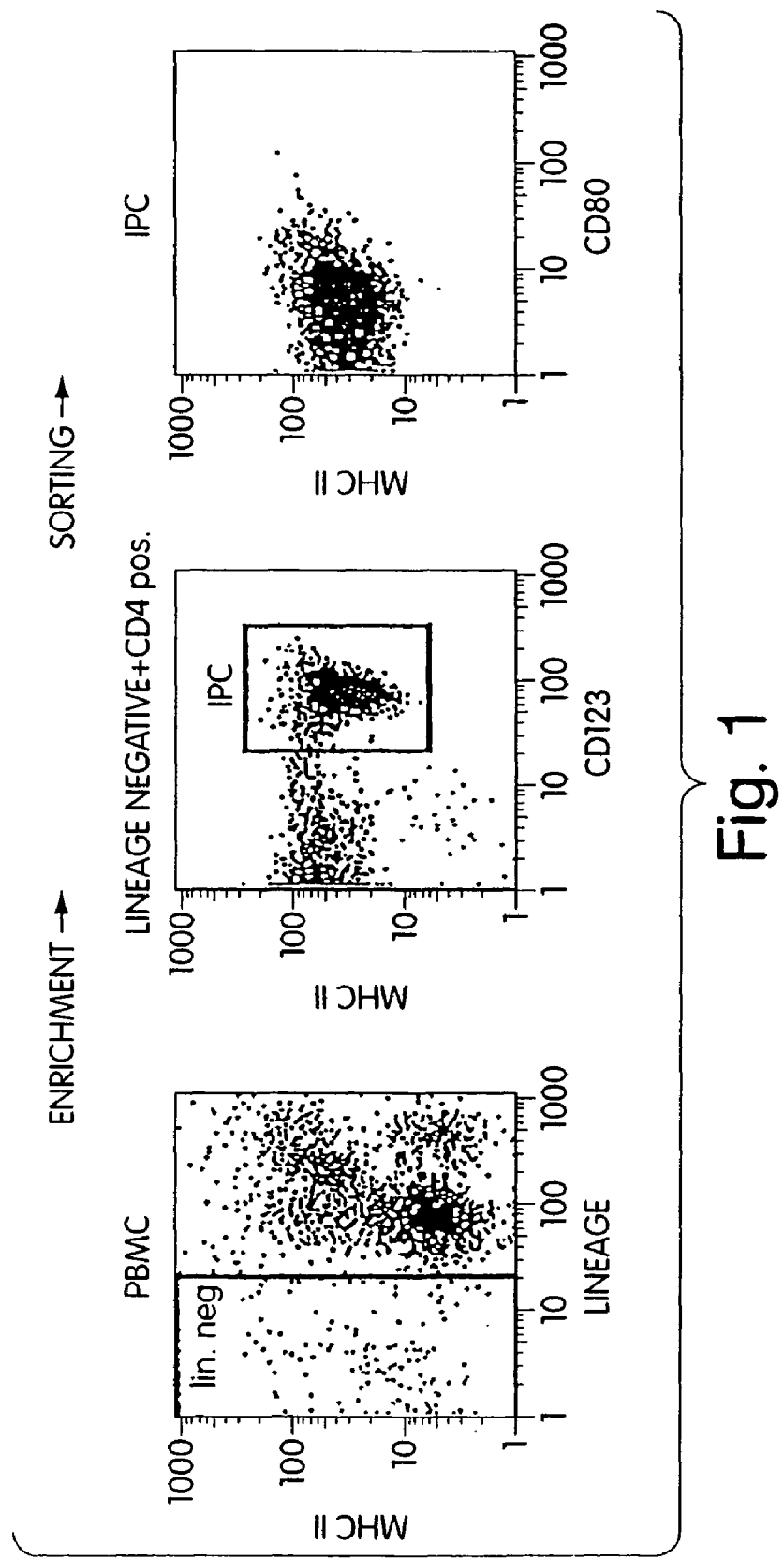
FIG. 1 depicts FACS analyses of cell populations during the isolation and characterization of IPCs performed with magnetic beads and flow cytometry. From left to right are shown: selection of lin−/MHC class II+ cells from PBMCs; further selection of CD123+/MHC class II+ cells from lin−/CD4+/MHC class II+ cells; and characterization of freshly isolated lin−/CD4+/MHC class II+/CD123+ IPCs as CD80−.

The invention involves the discovery that a particular subset of blood cells, natural IFN-producing cells (IPCs), are stimulated by ISNAs to produce IFN-α. This discovery was surprising because it was previously unknown what component of UV-irradiated virus or of heat-killed bacteria was responsible for inducing IFN-α production by IPCs. Siegal F P et al. *Science* 284:1835-7 (1999). The discovery was also surprising because mature DC2s, which arise from the IPCs, are not strong producers of IFN-α. Furthermore, it was also known that monocyte-derived dendritic cells (DC1s) do not produce IFN-α in response to CpG nucleic acids. It also was surprising that a broad array of IFN-α molecules is stimulated. In addition, the invention involves the local induction of IFN-α at the site of ISNA administration, thus avoiding toxic effects associated with systemic administration of IFN-α in doses necessary to achieve similar local concentration of IFN-α. The invention also involves the unexpected discovery that ISNAs can stimulate IFN-producing cells to activate them to express the costimulatory molecule CD80 (B7-1). Another unexpected discovery is that ISNAs can support the survival of IFN-producing cells even in the absence of interleukin-3. These various discoveries have led to the in vivo, ex vivo and in vitro inventions described herein.

An ISNA is a nucleic acid molecule which, upon contacting cells of the immune system, is itself capable of inducing contacted cells of the immune system to proliferate and/or to become activated. The contacting can be direct or indirect, e.g., the ISNA may directly stimulate a first type of immune cell to express a product which may in turn stimulate a second type of immune cell which has not been exposed to, or is not responsive to, the ISNA. The immunostimulatory effect of the ISNA is separate from any product that might happen to be encoded by the sequence of the ISNA. Similarly, the immunostimulatory effect of an ISNA is distinct from and does not rely upon any antisense mechanism. Only certain nucleic acids are ISNAs. Originally it was believed that certain palindromic sequences were immunostimulatory. Tokunaga T et al. *Microbiol Immunol* 36:55-66 (1992); Yamamoto T et al. *Antisense Res Dev* 4:119-22 (1994). Further work demonstrated that non-palindromic sequences are also immunostimulatory provided they contained CpG dinucleotides within particular sequence contexts (CpG motifs). Krieg A M et al. *Nature* 374:546-9 (1995). The ISNAs can be single-stranded or double-stranded. Generally, double-stranded nucleic acid molecules are more stable in vivo, while single-stranded nucleic acid molecules have increased immune activity. Thus in some aspects of the invention it is preferred that the ISNA be single-stranded and in other aspects it is preferred that the ISNA be double-stranded.

The terms "nucleic acid" and "oligonucleotide" are used interchangeably to mean multiple, covalently linked nucleotides, wherein each nucleotide comprises a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G)).

As used herein, the terms "nucleic acid" and "oligonucleotide" refer to oligoribonucleotides as well as oligodeoxyribonucleotides. The terms shall also include polynucleotides (i.e., a polynucleotide minus the phosphate) and any other organic base-containing polymer. Nucleic acid molecules can be obtained from existing nucleic acid sources (e.g., genomic DNA or cDNA), but are preferably synthetic (e.g., produced by oligonucleotide synthesis).

The terms "nucleic acid" and "oligonucleotide" also encompass nucleic acids or oligonucleotides with a covalently modified base and/or sugar. For example, they include nucleic acids having backbone sugars which are covalently attached to low molecular weight organic groups other than a hydroxyl group at the 3' position and other than a phosphate group at the 5' position. Thus modified nucleic acids may include a 2'-O-alkylated ribose group. In addition, modified nucleic acids may include sugars such as arabinose instead of ribose. Thus the nucleic acids may be heterogeneous in backbone composition thereby containing any possible combination of polymer units linked together such as peptide nucleic acids (which have an amino acid backbone with nucleic acid bases). In some embodiments the nucleic acids are homogeneous in backbone composition.

Nucleic acids also can include base analogs such as C-5 propyne modified bases. Wagner et al. *Nature Biotechnology* 14:840-844 (1996). Purines and pyrimidines include but are not limited to adenine, cytosine, guanine, thymine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties.

The nucleic acid is a linked polymer of bases, nucleobase analogs, or nucleotides. As used herein with respect to linked units of a nucleic acid, "linked" or "linkage" means two entities are bound to one another by any physicochemical means. Any linkage known to those of ordinary skill in the art, covalent or non-covalent, is embraced. Such linkages are well known to those of ordinary skill in the art. Natural linkages, which are those ordinarily found in nature connecting the individual units of a nucleic acid, are most common. The individual units of a nucleic acid may be linked, however, by synthetic or modified linkages.

A CpG oligonucleotide is an oligonucleotide which includes at least one unmethylated CpG dinucleotide. An oligonucleotide containing at least one unmethylated CpG dinucleotide is a nucleic acid molecule which contains an unmethylated cytosine-guanine dinucleotide sequence (i.e., "CpG DNA" or DNA containing a 5' cytosine followed by 3' guanine and linked by a phosphate bond) and activates the immune system. The entire CpG oligonucleotide can be unmethylated or portions may be unmethylated but at least the C of the 5' CG 3' must be unmethylated. The CpG oligonucleotides can be double-stranded or single-stranded. The terms CpG oligonucleotide or CpG nucleic acid as used herein refer to an immunostimulatory CpG oligonucleotide or a nucleic acid unless otherwise indicated.

In one preferred embodiment the invention provides a CpG oligonucleotide represented by at least the formula:

$$5'X_1X_2CGX_3X_43'$$

wherein $X_1$, $X_2$, $X_3$, and $X_4$ are nucleotides. In one embodiment $X_2$ is adenine, guanine, or thymine. In another embodiment $X_3$ is cytosine, adenine, or thymine.

In another embodiment the invention provides an isolated CpG oligonucleotide represented by at least the formula:

$$5'N_1X_1X_2CGX_3X_4N_23'$$

wherein $X_1$, $X_2$, $X_3$, and $X_4$ are nucleotides and N is any nucleotide and $N_1$ and $N_2$ are nucleic acid sequences composed of from about 0-25 N's each. In one embodiment $X_1X_2$ is a dinucleotide selected from the group consisting of: GpT, GpG, GpA, ApA, ApT, ApG, CpT, CpA, CpG, TpA, TpT, and TpG; and $X_3X_4$ is a dinucleotide selected from the group consisting of: TpT, ApT, TpG, ApG, CpG, TpC, ApC, CpC, TpA, ApA, and CpA. Preferably $X_1X_2$ is GpA or GpT and $X_3X_4$ is TpT. In other embodiments $X_1$ or $X_2$ or both are purines and $X_3$ or $X_4$ or both are pyrimidines or $X_1X_2$ is GpA and $X_3$ or $X_4$ or both are pyrimidines. In another preferred embodiment $X_1X_2$ is a dinucleotide selected from the group consisting of: TpA, ApA, ApC, ApG, and GpG. In yet another embodiment $X_3X_4$ is a dinucleotide selected from the group consisting of: TpT, TpA, TpG, ApA, ApG, GpA, and CpA. $X_1X_2$ in another embodiment is a dinucleotide selected from the group consisting of: TpT, TpG, ApT, GpC, CpC, CpT, TpC, GpT and CpG; $X_3$ is a nucleotide selected from the group consisting of A and T and $X_4$ is a nucleotide, but wherein when $X_1X_2$ is TpC, GpT, or CpG, $X_3X_4$ is not TpC, ApT or ApC.

In another preferred embodiment the CpG oligonucleotide has the sequence 5' $TCN_1TX_1X_2CGX_3X_4$ 3'. The CpG oligonucleotides of the invention in some embodiments include $X_1X_2$ selected from the group consisting of GpT, GpG, GpA and ApA and $X_3X_4$ is selected from the group consisting of TpT, CpT and TpC.

For facilitating uptake into cells, ISNAs, including CpG-containing oligonucleotides, are preferably in the range of 8 to 100 bases in length. However, nucleic acids of any size greater than 8 nucleotides (even many kb long) are capable of inducing an immune response according to the invention if sufficient immunostimulatory motifs are present, since larger nucleic acids are degraded into oligonucleotides inside of cells. Preferably the ISNA is in the range of between 8 and 100 nucleotides in length. In some preferred embodiments the ISNA is between 12 and 40 nucleotides in length. In more preferred embodiments the ISNA is between 8 and 30 nucleotides in length. In most preferred embodiments the ISNA is between 8 and 24 nucleotides in length.

"Palindromic sequence" shall mean an inverted repeat, i.e., a sequence such as ABCDEE'D'C'B'A' in which A and A', B and B', C and C', D and D', and E and E' are bases capable of forming the usual Watson-Crick base pairs. In vivo, such palindromic sequences may form double-stranded structures. In one embodiment the CpG oligonucleotide contains a palindromic sequence. A palindromic sequence used in this context refers to a palindrome in which the CpG is part of the palindrome, and preferably is the center of the palindrome. In another embodiment the CpG oligonucleotide is free of a palindrome. A CpG oligonucleotide that is free of a palindrome is one in which the CpG dinucleotide is not part of a palindrome. Such an oligonucleotide may include a palindrome in which the CpG is not the center of the palindrome.

The CpG nucleic acid sequences of the invention are those broadly described above as well as disclosed in PCT Published Patent Applications PCT/US95/01570 and PCT/US97/19791 claiming priority to U.S. Ser. Nos. 08/386,063 and 08/960,774, filed on Feb. 7, 1995 and Oct. 30, 1997 respectively. Exemplary sequences include but are not limited to those immunostimulatory sequences shown in Table 3 and Table 5.

TABLE 3

| Exemplary CpG ISNAs | |
|---|---|
| AACGTTCT | SEQ ID NO:38 |
| ACCATGGACGAACTGTTTCCCCTC | SEQ ID NO:39 |
| ACCATGGACGACCTGTTTCCCCTC | SEQ ID NO:40 |
| ACCATGGACGAGCTGTTTCCCCTC | SEQ ID NO:41 |
| ACCATGGACGATCTGTTTCCCCTC | SEQ ID NO:42 |
| ACCATGGACGGTCTGTTTCCCCTC | SEQ ID NO:43 |
| ACCATGGACGTACTGTTTCCCCTC | SEQ ID NO:44 |
| ACCATGGACGTTCTGTTTCCCCTC | SEQ ID NO:45 |
| AGCTATGACGTTCCAAGG | SEQ ID NO:46 |
| ATAGGAGGTCCAACGTTCTC | SEQ ID NO:47 |
| ATCGACTCTCGAACGTTCTC | SEQ ID NO:48 |
| ATCGACTCTCGAGCGTTCTC | SEQ ID NO:49 |
| ATGACGTTCCTGACGTT | SEQ ID NO:50 |
| ATGGAAGGTCCAACGTTCTC | SEQ ID NO:51 |
| ATGGAAGGTCCAGCGTTCTC | SEQ ID NO:52 |
| ATGGACTCTCCAGCGTTCTC | SEQ ID NO:53 |
| ATGGAGGCTCCATCGTTCTC | SEQ ID NO:54 |
| CAACGTT | SEQ ID NO:55 |
| CACGTTGAGGGGCAT | SEQ ID NO:56 |
| CCAACGTT | SEQ ID NO:57 |
| GAGAACGATGGACCTTCCAT | SEQ ID NO:58 |
| GAGAACGCTCCAGCACTGAT | SEQ ID NO:59 |
| GAGAACGCTCGACCTTCCAT | SEQ ID NO:60 |
| GAGAACGCTCGACCTTCGAT | SEQ ID NO:61 |
| GAGAACGCTGGACCTTCCAT | SEQ ID NO:62 |
| GCATGACGTTGAGCT | SEQ ID NO:63 |
| GCGTGCGTTGTCGTTGTCGTT | SEQ ID NO:64 |
| GCTAGACGTTAGCGT | SEQ ID NO:65 |
| GCTAGACGTTAGTGT | SEQ ID NO:66 |
| GCTAGATGTTAGCGT | SEQ ID NO:67 |

TABLE 3-continued

| Exemplary CpG ISNAs | |
|---|---|
| GGGGTCAACGTTGACGGGG | SEQ ID NO:68 |
| GGGGTCAGTCGTGACGGGG | SEQ ID NO:69 |
| GTCGYT | SEQ ID NO:70 |
| TCAACGTC | SEQ ID NO:71 |
| TCAACGTT | SEQ ID NO:72 |
| TCAGCGCT | SEQ ID NO:73 |
| TCAGCGTGCGCC | SEQ ID NO:74 |
| TCATCGAT | SEQ ID NO:75 |
| TCCACGACGTTTTCGACGTT | SEQ ID NO:76 |
| TCCATAACGTTCCTGATGCT | SEQ ID NO:77 |
| TCCATAGCGTTCCTAGCGTT | SEQ ID NO:78 |
| TCCATCACGTGCCTGATGCT | SEQ ID NO:79 |
| TCCATGACGGTCCTGATGCT | SEQ ID NO:80 |
| TCCATGACGTCCCTGATGCT | SEQ ID NO:81 |
| TCCATGACGTGCCTGATGCT | SEQ ID NO:82 |
| TCCATGACGTTCCTGACGTT | SEQ ID NO:83 |
| TCCATGACGTTCCTGATGCT | SEQ ID NO:84 |
| TCCATGCCGGTCCTGATGCT | SEQ ID NO:85 |
| TCCATGCGTGCGTGCGTTTT | SEQ ID NO:86 |
| TCCATGCGTTGCGTTGCGTT | SEQ ID NO:87 |
| TCCATGGCGGTCCTGATGCT | SEQ ID NO:88 |
| TCCATGTCGATCCTGATGCT | SEQ ID NO:89 |
| TCCATGTCGCTCCTGATGCT | SEQ ID NO:90 |
| TCCATGTCGGTCCTGACGCA | SEQ ID NO:91 |
| TCCATGTCGGTCCTGATGCT | SEQ ID NO:92 |
| TCCATGTCGGTCCTGCTGAT | SEQ ID NO:93 |
| TCCATGTCGTCCCTGATGCT | SEQ ID NO:94 |
| TCCATGTCGTTCCTGTCGTT | SEQ ID NO:95 |
| TCCATGTCGTTTTGTCGTT | SEQ ID NO:96 |
| TCCTGACGTTCCTGACGTT | SEQ ID NO:97 |
| TCCTGTCGTTCCTGTCGTT | SEQ ID NO:98 |
| TCCTGTCGTTCCTTGTCGTT | SEQ ID NO:99 |
| TCCTGTCGTTTTTTGTCGTT | SEQ ID NO:100 |
| TCCTTGTCGTTCCTGTCGTT | SEQ ID NO:101 |
| TCGTCGCTGTCTCCCCTTCTT | SEQ ID NO:102 |
| TCGTCGCTGTCTGCCCTTCTT | SEQ ID NO:103 |
| TCGTCGCTGTTGTCGTTTCTT | SEQ ID NO:104 |
| TCGTCGTCGTCGTT | SEQ ID NO:105 |
| TCGTCGTTGTCGTTGTCGTT | SEQ ID NO:106 |

TABLE 3-continued

Exemplary CpG ISNAs

| | |
|---|---|
| TCGTCGTTGTCGTTTTGTCGTT | SEQ ID NO:107 |
| TCGTCGTTTTGTCGTTTTGTCGTT | SEQ ID NO:108 |
| TCTCCCAGCGGGCGCAT | SEQ ID NO:109 |
| TCTCCCAGCGTGCGCCAT | SEQ ID NO:110 |
| TCTTCGAA | SEQ ID NO:111 |
| TCTTCGAT | SEQ ID NO:112 |
| TGTCGTTGTCGTT | SEQ ID NO:113 |
| TGTCGTTGTCGTTGTCGTT | SEQ ID NO:114 |
| TGTCGTTGTCGTTGTCGTTGTCGTT | SEQ ID NO:115 |
| TGTCGTTTGTCGTTTGTCGTT | SEQ ID NO:116 |
| TGTCGYT | SEQ ID NO:117 |

The immunostimulatory nucleic acids of the invention also include nucleic acids having T-rich motifs. As used herein, a "T-rich nucleic acid" is a nucleic acid which includes at least one poly-T sequence and/or which has a nucleotide composition of greater than 25% T nucleotide residues. A nucleic acid having a poly-T sequence includes at least four Ts in a row, such as 5' TTTT 3'. Preferably the T-rich nucleic acid includes more than one poly-T sequence. In preferred embodiments the T-rich nucleic acid may have 2, 3, 4, etc., poly-T sequences. One of the most highly immunostimulatory T-rich oligonucleotides is a nucleic acid composed entirely of T nucleotide residues. Other T-rich nucleic acids have a nucleotide composition of greater than 25% T nucleotide residues, but do not necessarily include a poly-T sequence. In these T-rich nucleic acids the T nucleotide residues may be separated from one another by other types of nucleotide residues, i.e., G, C, and A. In some embodiments the T-rich nucleic acids have a nucleotide composition of greater than 35%, 40%, 50%, 60%, 70%, 80%, 90%, and 99%, T nucleotide residues and every integer % in between. Preferably the T-rich nucleic acids have at least one poly-T sequence and a nucleotide composition of greater than 25% T nucleotide residues.

T-rich nucleic acids are also described and claimed in U.S. Ser. No. 09/669,187 filed on Sep. 25, 2000, claiming priority to U.S. Provisional Patent Application No. 60/156,113 filed on Sep. 25, 1999, which is hereby incorporated by reference. Many of the CpG ODN presented in Table 3 are also T-rich nucleic acids as defined here.

A number of references also describe the immunostimulatory properties of poly-G nucleic acids (defined below). Pisetsky and Reich (1993) *Mol Biol Reports* 18:217-221; Krieger and Herz (1994) *Ann Rev Biochem* 63:601-637; Macaya et al. (1993) *Proc Natl Acad Sci USA* 90:3745-3749; Wyatt et al. (1994) *Proc Natl Acad Sci USA* 91:1356-1360; Rando and Hogan (1998) In: Applied Antisense Oligonucleotide Technology, eds. Krieg and Stein, p. 335-352; and Kimura et al. (1994) *J Biochem* 116:991-994. Poly-G-containing oligonucleotides are useful for treating and preventing bacterial and viral infections.

It was previously suggested in the prior art that poly-G rich oligonucleotides inhibit the production of IFN-γ by compounds such as CpG oligonucleotides, concanavalin A, bacterial DNA, or the combination of phorbol 12-myristate 13-acetate (PMA) and the calcium ionophore A 23187 (Halperin and Pisetsky (1995) *Immunopharmacol* 29:47-52), as well as block the downstream effects of IFN-γ. For instance, Ramanathan et al. has shown that a poly-G oligonucleotide inhibits the binding of IFN-γ to its receptor, which prevents the normal enhancement of MHC class I and ICAM-1 in response to IFN-γ. Ramanathan et al. (1994) *Transplantation* 57:612-615. Poly-G oligonucleotides were also found to be able to inhibit the secretion of IFN-γ from lymphocytes. Halperin and Pisetsky (1995) *Immunopharmacol* 29:47-52.

Poly-G nucleic acids preferably are nucleic acids having the following formula:

5'$X_1X_2GGGX_3X_4$3' wherein $X_1$, $X_2$, $X_3$, and $X_4$ are nucleotides. In preferred embodiments at least one of $X_3$ and $X_4$ is a G. In other embodiments both of $X_3$ and $X_4$ are G's. In yet other embodiments the preferred formula is 5' GGGNGGG 3' (SEQ ID NO:168) or 5' GGGNGGGNGGG 3' (SEQ ID NO:169), wherein N represents between 0 and 20 nucleotides. In other embodiments the poly-G nucleic acid is free of CpG dinucleotides, such as, for example, the nucleic acids listed in Table 4 as SEQ ID NOs 95-114, 117-121, 123-130, 132, and 133. In other embodiments the poly-G nucleic acid includes at least one CpG dinucleotide, such as, for example, the nucleic acids listed in Table 4 as SEQ ID NOs 115, 116, 122, 131, and 134-136. Particularly preferred ISNAs are SEQ ID NOs 134, 135, and 136.

TABLE 4

Poly-G ISNAs

| | |
|---|---|
| ATGGAAGGTCCAAGGGGCTC | SEQ ID NO:118 |
| ATGGAAGGTCCAGGGGGCTC | SEQ ID NO:119 |
| ATGGAAGGTCCGGGGTTCTC | SEQ ID NO:120 |
| ATGGACTCTCCGGGGTTCTC | SEQ ID NO:121 |
| ATGGACTCTGGAGGGGGCTC | SEQ ID NO:122 |
| ATGGACTCTGGAGGGGTCTC | SEQ ID NO:123 |
| ATGGACTCTGGGGGGTTCTC | SEQ ID NO:124 |
| ATGGAGGCTCCATGGGGCTC | SEQ ID NO:125 |
| GAGAAGGGGCCAGCACTGAT | SEQ ID NO:126 |
| GAGAAGGGGGGACCTTCCAT | SEQ ID NO:127 |
| GAGAAGGGGGGACCTTGGAT | SEQ ID NO:128 |
| GCATGAGGGGGAGCT | SEQ ID NO:129 |
| GCTAGAGGGAGTGT | SEQ ID NO:130 |
| GCTAGAGGGGAGGGT | SEQ ID NO:131 |
| GCTAGATGTTAGGGG | SEQ ID NO:132 |
| GGGGGACGATCGTCGGGGGG | SEQ ID NO:133 |
| GGGGGGGGGGGGGGGGGGGG | SEQ ID NO:134 |
| GGGGTCAACGTTGAGGGGGG | SEQ ID NO:135 |
| GGGGTCGACGTCGAGGGGGG | SEQ ID NO:136 |
| TCCATCGGGGGCCTGATGCT | SEQ ID NO:137 |

TABLE 4-continued

Poly-G ISNAs

| | |
|---|---|
| TCCATGAGGGGCCTGATGCT | SEQ ID NO:138 |
| TCCATGCGGGTGGGGATGCT | SEQ ID NO:139 |
| TCCATGGGGGTCCTGATGCT | SEQ ID NO:140 |
| TCCATGGGGTCCCTGATGCT | SEQ ID NO:141 |
| TCCATGGGGTGCCTGATGCT | SEQ ID NO:142 |
| TCCATGGGGTTCCTGATGCT | SEQ ID NO:143 |
| TCCATGTGGGGCCTGATGCT | SEQ ID NO:144 |
| TCCATGTGGGGCCTGCTGAT | SEQ ID NO:145 |
| TCCATGTGGGTGGGGATGCT | SEQ ID NO:146 |

More generally, ISNAs of the invention can include any combination of at least two types of ISNAs, including CpG nucleic acids, T-rich nucleic acids, and poly-G nucleic acids. Such combinations can occur in the form of chimeric nucleic acids, in which the at least two types of ISNA are represented in a single nucleic acid molecule.

In addition, at least two individual nucleic acid molecules with different sequences and/or different types of ISNA, can be used together. The at least two individual nucleic acid molecules used together can represent a single type or at least two types of ISNA.

A preferred composition for inducing IFN-α is a composition including an oligonucleotide having a phosphate modification at the 3' and 5' ends of the molecule with a phosphodiester central region. This preferred molecule is exemplified by the following formula:

5'$Y_1N_1CGN_2Y_2$3' wherein $Y_1$ and $Y_2$ are, independent of one another, nucleic acid molecules having between 1 and 10 nucleotides, and wherein $Y_1$ includes at least one modified internucleotide linkage and $Y_2$ includes at least one modified internucleotide linkage and wherein $N_1$ and $N_2$ are nucleic acid molecules, each independent of one another having between 0 and 20 nucleotides and in some embodiments, between 3 and 8 nucleotides, but wherein $N_1CGN_2$ has at least 6 nucleotides in total and wherein the nucleotides of $N_1CGN_2$ have a phosphodiester backbone. Oligonucleotides having one or more phosphorothioate-modified internucleotide linkages with a central region having one or more phosphodiester internucleotide linkages demonstrated unexpectedly high ability to induce IFN-α. The activity of these oligonucleotides was particularly high when the first two and last five internucleotide linkages include phosphate modifications and/or the oligonucleotide included poly-G ends.

$Y_1$ and $Y_2$ are considered independent of one another. This means that each of $Y_1$ and $Y_2$ may or may not have different sequences and different backbone linkages from one another in the same molecule. The sequences vary, but in some cases $Y_1$ and $Y_2$ have a poly-G sequence. A poly-G sequence refers to at least 3 Gs in a row. In other embodiments the poly-G sequence refers to at least 4, 5, 6, 7, or 8 Gs in a row.

In some embodiments $Y_1$ and $Y_2$ have between 3 and 8 or between 4 and 7 nucleotides. At least one of these nucleotides includes a modified internucleotide linkage. In some embodiments $Y_1$ and $Y_2$ include at least two modified internucleotide linkages, and in other embodiments $Y_1$ and $Y_2$ include between two and five modified internucleotide linkages. In yet other embodiments $Y_1$ has two modified internucleotide linkages and $Y_2$ has five modified internucleotide linkages. In other embodiments $Y_1$ has five modified internucleotide linkages and $Y_2$ has two modified internucleotide linkages.

Exemplary preferred ISNAs of the invention for inducing secretion of type I IFN are shown in Table 5 below with lower case letters indicating phosphorothioate linkages and upper case letters indicating phosphodiester linkages.

TABLE 5

Exemplary Preferred ISNAs for Inducing Type I IFN

| | | |
|---|---|---|
| ggGGTCAACGTTGAggggggG | ODN 1585 | SEQ ID NO:1 |
| tcgtcgttttgtcgttttgtcgtt | ODN 2022 | SEQ ID NO:2 |
| ggggtcgtcgttttgggggg | ODN 2184 | SEQ ID NO:3 |
| tcgtcgttttgtcgttttggggg | ODN 2185 | SEQ ID NO:4 |
| ggggtcgacgtcgaggggggg | ODN 2192 | SEQ ID NO:5 |
| ggggtcatcgatgaggggggg | ODN 2204 | SEQ ID NO:6 |
| ggGGGACGATCGTCggggggG | ODN 2216 | SEQ ID NO:7 |
| gggggtcgtacgacgggggg | ODN 2217 | SEQ ID NO:8 |
| ggGGGACGATATCGTCggggggG | ODN 2245 | SEQ ID NO:9 |
| ggGGGACGACGTCGTCggggggG | ODN 2246 | SEQ ID NO:10 |
| ggGGGACGAGCTCGTCggggggG | ODN 2247 | SEQ ID NO:11 |
| ggGGGACGTACGTCggggggG | ODN 2248 | SEQ ID NO:12 |
| ggGGGACGATCGTTGggggggG | ODN 2252 | SEQ ID NO:13 |
| ggGGAACGATCGTCggggggG | ODN 2253 | SEQ ID NO:14 |
| ggGGGGACGATCGTCggggggG | ODN 2254 | SEQ ID NO:15 |
| ggGGGACGATCGTCggggggG | ODN 2255 | SEQ ID NO:16 |
| ggGGGTCATCGATGAggggggG | ODN 2260 | SEQ ID NO:17 |
| ggGGTCGTCGACGAggggggG | ODN 2293 | SEQ ID NO:18 |
| ggGGTCGTTCGAACGAggggggG | ODN 2294 | SEQ ID NO:19 |
| ggGGACGTTCGAACGTggggggG | ODN 2295 | SEQ ID NO:20 |
| ggGGAACGACGTCGTTggggggG | ODN 2297 | SEQ ID NO:21 |
| ggGGAACGTACGTCggggggG | ODN 2298 | SEQ ID NO:22 |
| ggGGAACGTACGTACGTTggggggG | ODN 2299 | SEQ ID NO:23 |
| ggGGTCACCGGTGAggggggG | ODN 2300 | SEQ ID NO:24 |
| ggGGTCGACGTACGTCGAggggggG | ODN 2301 | SEQ ID NO:25 |
| ggGGACCGGTACCGGTggggggG | ODN 2302 | SEQ ID NO:26 |
| ggGTCGACGTCGAggggggG | ODN 2303 | SEQ ID NO:27 |
| ggGGTCGACGTCGagggg | ODN 2304 | SEQ ID NO:28 |
| ggGGAACGTTAACGTTggggggG | ODN 2305 | SEQ ID NO:29 |
| ggGGACGTCGACGTggggggG | ODN 2306 | SEQ ID NO:30 |
| ggGGGTCGTTCGTTggggggG | ODN 2311 | SEQ ID NO:31 |
| ggGACGATCGTCGggggggG | ODN 2328 | SEQ ID NO:32 |
| ggGTCGTCGACGAggggggG | ODN 2329 | SEQ ID NO:33 |

TABLE 5-continued

Exemplary Preferred ISNAs for Inducing Type I IFN

| | | |
|---|---|---|
| ggTCGTCGACGAGgggggG | ODN 2330 | SEQ ID NO:34 |
| ggGGACGATCGTCGgggggG | ODN 2332 | SEQ ID NO:35 |
| ggGGTCGACGTCGACGTCGAGgggggG and | ODN 2334, | SEQ ID NO:36 |
| ggGGACGACGTCGTGgggggG | ODN 2336. | SEQ ID NO:37 |

For use in the instant invention, the nucleic acids can be synthesized de novo using any of a number of procedures well known in the art. For example, the nucleic acids can be synthesized using the β-cyanoethyl phosphoramidite method (Beaucage S L and Caruthers M H *Tetrahedron Lett* 22:1859 (1981)) or the nucleoside H-phosphonate method (Garegg et al. *Tetrahedron Lett* 27:4051 (1986); Froehler et al. *Nucl Acid Res* 14:5399 (1986); Garegg et al. *Tetrahedron Lett* 27:4055 (1986); Gaffney et al. *Tetrahedron Lett* 29:2619 (1988)). These chemistries can be performed by a variety of automated oligonucleotide synthesizers available in the market. These oligonucleotides are referred to as synthetic oligonucleotides. Alternatively, ISNAs can be produced on a large scale in plasmids, (see Sambrook, T., et al., "Molecular Cloning: A Laboratory Manual", Cold Spring Harbor Laboratory Press, New York, 1989) and separated into smaller pieces or administered whole. Oligonucleotides can be prepared from existing nucleic acid sequences (e.g., genomic DNA or cDNA) using known techniques, such as those employing restriction enzymes, exonucleases or endonucleases. Oligonucleotides prepared in this manner are referred to as isolated oligonucleotides. The term ISNA encompasses both synthetic and isolated immunostimulatory nucleic acids.

For use in vivo, ISNAs are preferably relatively resistant to degradation (e.g., are stabilized). A "stabilized nucleic acid molecule" shall mean a nucleic acid molecule that is relatively resistant to in vivo degradation (e.g., via an exo- or endo-nuclease). Stabilization can be a function of length or secondary structure. For example, ISNAs that are tens to hundreds of kbs long are relatively resistant to in vivo degradation. For shorter ISNAs, secondary structure can stabilize and increase their effect. For example, if the 3' end of an oligonucleotide has self-complementarity to an upstream region, so that it can fold back and form a sort of stem loop structure, then the oligonucleotide becomes stabilized and therefore exhibits more activity.

Alternatively, nucleic acid stabilization can be accomplished via phosphate backbone modifications. Preferred stabilized oligonucleotides of the instant invention have a modified backbone. It has been demonstrated that modification of the oligonucleotide backbone provides enhanced activity of the ISNAs when administered in vivo. These stabilized structures are preferred because the ISNAs of the invention have at least a partial modified backbone. For example, CpG oligonucleotides of a given sequence which include at least two phosphorothioate linkages at the 5' end of the oligonucleotide and multiple phosphorothioate linkages at the 3' end, preferably five, provide maximal activity and protect the oligonucleotide from degradation by intracellular exo- and endo-nucleases. Other modified oligonucleotides include phosphodiester modified oligonucleotides, combinations of phosphodiester and phosphorothioate oligonucleotide, methylphosphonate, methylphosphorothioate, phosphorodithioate, and combinations thereof. Each of these combinations and their particular effects on immune cells is discussed in more detail in PCT Published Patent Applications PCT/US95/01570 and PCT/US97/19791 claiming priority to U.S. Ser. Nos. 08/386,063 and 08/960,774, filed on Feb. 7, 1995 and Oct. 30, 1997, respectively, the entire contents of which is hereby incorporated by reference. It is believed that these modified backbone oligonucleotides may show more stimulatory activity due to enhanced nuclease resistance, increased cellular uptake, increased protein binding, and/or altered intracellular localization.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described. Uhlmann E and Peyman A *Chem Rev* 90:544 (1990); Goodchild J *Bioconjugate Chem* 1: 165 (1990).

Other stabilized oligonucleotides include: nonionic DNA analogs, such as alkyl- and aryl-phosphates (in which the charged phosphonate oxygen is replaced by an alkyl or aryl group), and alkylphosphodiester and alkylphosphotriesters (in which the charged oxygen moiety is alkylated). Oligonucleotides which contain diol, such as tetraethyleneglycol or hexaethyleneglycol, at either or both termini have also been shown to be substantially resistant to nuclease degradation.

In some embodiments the ISNAs useful according to the invention are S and R chiral ISNAs. An "S chiral ISNA" as used herein is an ISNA wherein at least two nucleotides have a backbone modification forming a chiral center and wherein a plurality of the chiral centers have S chirality. An "R chiral ISNA" as used herein is an ISNA wherein at least two nucleotides have a backbone modification forming a chiral center and wherein a plurality of the chiral centers have R chirality. The backbone modification may be any type of modification that forms a chiral center. The modifications include but are not limited to phosphorothioate, phosphorodithioate, methylphosphonate, methylphosphorothioate, and combinations thereof.

The chiral ISNAs must have at least two nucleotides within the oligonucleotide that have a backbone modification. All or less than all of the nucleotides in the oligonucleotides, however, may have a modified backbone. Of the nucleotides having a modified backbone (referred to as chiral centers), a plurality have a single chirality, S or R. A "plurality" as used herein refers to an amount greater than 50 percent. Thus, less than all of the chiral centers may have S or R chirality as long as a plurality of the chiral centers have S or R chirality. In some embodiments at least 55 percent, 60 percent, 65 percent, 70 percent, 75 percent, 80 percent, 85 percent, 90 percent, 95 percent, or 100 percent of the chiral centers have S or R chirality. In other embodiments at least 55 percent, 60 percent, 65 percent, 70 percent, 75 percent, 80 percent, 85 percent, 90 percent, 95 percent, or 100 percent of the nucleotides have backbone modifications.

The S and R chiral ISNAs may be prepared by any method known in the art for producing chirally pure oligonucleotides. Many references teach methods for producing stereopure phosphorothioate oligodeoxynucleotides using an oxathiaphospholane method have been published. Stec W J et al. *J Am Chem Soc* 117:12019 (1995). Other methods for making chirally pure oligonucleotides have been described by companies such as ISIS Pharmaceuticals. U.S. Patents have also described these methods. For instance, U.S. Pat. Nos. 5,883,237; 5,837,856; 5,599,797; 5,512,668; 5,856,465; 5,359,052; 5,506,212; 5,521,302; and 5,212,295, each of which is hereby incorporated by reference in its entirety, disclose methods for generating stereopure oligonucleotides.

A "subject" shall mean a human or vertebrate animal including but not limited to a dog, cat, horse, cow, pig, sheep, goat, chicken, non-human primate (e.g., monkey), fish (aquaculture species, e.g., salmon), rabbit, rat, and mouse.

A "subject having a proliferative disorder" is a subject that has detectable and unwanted proliferating cells. The unwanted proliferating cell can be cancerous cells in a subject with cancer. The cancer may be a malignant or non-malignant cancer. Cancers or tumors include but are not limited to biliary tract cancer; bladder cancer; brain cancer; breast cancer; cervical cancer; choriocarcinoma; colon cancer; endometrial cancer; esophageal cancer; gastric cancer; intraepithelial neoplasms; leukemia; liver cancer; lung cancer (e.g., small cell and non-small cell); lymphoma; melanoma; multiple myeloma; neuroblastomas; oral cancer; ovarian cancer; pancreas cancer; prostate cancer; rectal cancer; renal cancer, sarcomas; skin cancer; stomach cancer; testicular cancer; and thyroid cancer; as well as other carcinomas and sarcomas. In other embodiments the unwanted proliferating cells can be non-cancerous, e.g., cells associated with an autoimmune condition or inflammatory condition.

A "subject having a viral infection" is a subject that has been exposed to a virus and has acute or chronic manifestations or detectable levels of the virus in the body.

Examples of viruses that have been found in humans include but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., hepatitis C virus (HCV), dengue viruses, encephalitis viruses, yellow fever viruses); Coronoviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); Iridoviridae (e.g., African swine fever virus); and unclassified viruses (e.g., the etiological agents of spongiform encephalopathies, the agent of delta hepatitis (thought to be a defective satellite of hepatitis B virus), the unclassified agents of non-A, non-B hepatitis (class 1=internally transmitted; class 2=parenterally transmitted); Norwalk and related viruses, and astroviruses).

Although many of the viruses described above relate to human disorders, the invention is also useful for treating nonhuman vertebrates. Nonhuman vertebrates are also capable of developing infections which can be prevented or treated with the ISNAs disclosed herein. For instance, in addition to the treatment of infectious human diseases, the methods of the invention are useful for treating infections of animals.

Infectious virus of both human and non-human vertebrates include retroviruses, RNA viruses and DNA viruses. This group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-2, simian T-cell leukemia virus (STLV), and bovine leukemia virus (BLV). The foamy viruses include human foamy virus (HFV), simian foamy virus (SFV) and bovine foamy virus (BFV).

Examples of other RNA viruses that are antigens in vertebrate animals include, but are not limited to, the following: members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, murine rotavirus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus Cardiovirus (encephalomyocarditis virus (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); the family Rhabdoviridae, including the genus Vesiculovirus (VSV), Chandipura virus, Flanders-Hart Park virus), the genus Lyssavirus (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that are antigens in vertebrate animals include, but are not limited to: the family Poxviridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the α-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A,B,C,D,E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc.). Finally, DNA viruses may include viruses which do not fit into the above families such as Kuru and Creutzfeldt-Jacob disease viruses and chronic infectious neuropathic agents (CHINA virus).

Each of the foregoing lists is illustrative, and is not intended to be limiting. In addition, these viruses, either in intact form or as fragments thereof, can be used as antigens in immunization procedures. An antigen is a substance recognized by the immune system as foreign and which induces specific immunity. Antigens can be carbohydrates (including, e.g., polysaccharides, glycolipids, and glycoproteins), proteins and polypeptides, as well as other oligomers, polymers, and small molecules which can bind to antigen receptors on immune cells. Specific immunity to an antigen can involve antigen recognition by T cells and/or B cells.

Nucleic acids containing an appropriate ISNA can be effective in any vertebrate. Different nucleic acids containing an ISNA can cause optimal immune stimulation depending on the mammalian species. Thus an oligonucleotide causing optimal stimulation or inhibition in humans may not cause optimal stimulation or inhibition in a mouse, and vice versa. One of skill in the art can identify the optimal oligonucleotides useful for a particular mammalian species of interest using routine assays described herein and/or known in the art, using the guidance supplied herein.

The ISNA may be directly administered to the subject or may be administered in conjunction with a nucleic acid delivery complex. A "nucleic acid delivery complex" shall mean a nucleic acid molecule associated with (e.g., ionically or covalently bound to; or encapsulated within) a targeting means (e.g., a molecule that results in higher affinity binding to target cell (e.g., B cell surfaces and/or increased cellular uptake by target cells). Examples of nucleic acid delivery complexes include nucleic acids associated with: a sterol (e.g., cholesterol), a lipid (e.g., a cationic lipid, virosome or liposome), or a target cell specific binding agent (e.g., a ligand recognized by target cell specific receptor). Preferred complexes may be sufficiently stable in vivo to prevent significant uncoupling prior to internalization by the target cell. However, the complex can be cleavable under appropriate conditions within the cell so that the nucleic acid is released in a functional form.

The ISNA or other therapeutics may be administered alone (e.g., in saline or buffer) or using any delivery vehicles known in the art. For instance the following delivery vehicles have been described: cochleates (Gould-Fogerite et al., 1994, 1996); emulsomes (Vancott et al., 1998, Lowell et al., 1997); ISCOMs (Mowat et al., 1993, Carlsson et al., 1991, Hu et., 1998, Morein et al., 1999); liposomes (Childers et al., 1999, Michalek et al., 1989, 1992, de Haan 1995a, 1995b); live bacterial vectors (e.g., *Salmonella, Escherichia coli, Bacillus Calmette-Guerin, Shigella, Lactobacillus*) (Hone et al., 1996, Pouwels et al., 1998, Chatfield et al., 1993, Stover et al., 1991, Nugent et al., 1998); live viral vectors (e.g., Vaccinia, adenovirus, Herpes Simplex) (Gallichan et al., 1993, 1995, Moss et al., 1996, Nugent et al., 1998, Flexner et al., 1988, Morrow et al., 1999); microspheres (Gupta et al., 1998, Jones et al., 1996, Maloy et al., 1994, Moore et al., 1995, O'Hagan et al., 1994, Eldridge et al., 1989); nucleic acid vaccines (Fynan et al., 1993, Kuklin et al., 1997, Sasaki et al., 1998, Okada et al., 1997, Ishii et al., 1997); polymers (e.g., carboxymethylcellulose, chitosan) (Hamajima et al., 1998, Jabbal-Gill et al., 1998); polymer rings (Wyatt et al., 1998); Proteosomes (Vancott et al., 1998, Lowell et al., 1988, 1996, 1997); sodium fluoride (Hashi et al., 1998); transgenic plants (Tacket et al., 1998, Mason et al., 1998, Haq et al., 1995); virosomes (Gluck et al., 1992, Mengiardi et al., 1995, Cryz et al., 1998); virus-like particles (Jiang et al., 1999, Leibl et al., 1998). Those skilled in the art will recognize that other delivery vehicles that are known in the art may also be used.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular ISNA being administered (e.g., the number of unmethylated CpG motifs or their location in the nucleic acid, the degree of chirality to the oligonucleotide), the antigen, the size of the subject, or the severity of the disease or condition. One of ordinary skill in the art can empirically determine the effective amount of a particular ISNA and/or antigen and/or other therapeutic agent without necessitating undue experimentation.

For adult human subjects, doses of the ISNA compounds described herein typically range from about 50 µg/dose to 20 mg/dose, more typically from about 80 µg/dose to 8 mg/dose, and most typically from about 800 µg/dose to 4 mg/dose. Stated in terms of subject body weight, typical dosages range from about 0.5 to 500 µg/kg/dose, more typically from about 1 to 100 µg/kg/dose, and most typically from about 10 to 50 µg/kg/dose. Doses will depend on factors including the route of administration, e.g., oral administration may require a substantially larger dose than subcutaneous administration.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The ISNA can be given in conjunction with other agents known in the art to be useful in combination with IFN-α to treat viral and proliferative disorders. Examples of such other agents currently used or under investigation for use in combination with IFN-α include ribavirin, amantadine, chemotherapeutic agents (e.g., 5-fluorouracil and BCNU), radiation therapy, phototherapy, and cytokines, including IL-2, IL-12, and IFN-γ.

For use in therapy, an effective amount of the ISNA can be administered to a subject by any mode that delivers the ISNA to the desired site, e.g., mucosal, systemic. "Administering" the pharmaceutical composition of the present invention may be accomplished by any means known to the skilled artisan.

Preferred routes of administration include but are not limited to oral, parenteral, intralesional, topical, transdermal, intramuscular, intranasal, intratracheal, inhalational, ocular, vaginal, and rectal.

For oral administration, the compounds (i.e., ISNA, antigen, other therapeutic agent) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion.

Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer *Science* 249:1527 (1990), which is incorporated herein by reference.

The ISNAs may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulfuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2 percent w/v); citric acid and a salt (1-3 percent w/v); boric acid and a salt (0.5-2.5 percent w/v); and phosphoric acid and a salt (0.8-2 percent w/v). Suitable preservatives include benzalkonium chloride (0.003-0.03 percent w/v); chlorobutanol (0.3-0.9 percent w/v); parabens (0.01-0.25 percent w/v) and thimerosal (0.004-0.02 percent w/v).

The pharmaceutical compositions of the invention contain an effective amount of an ISNA and optionally antigens and/or other therapeutic agents optionally included in a pharmaceutically-acceptable carrier. The term "pharmaceutically-acceptable carrier" means one or more compatible solid or liquid filler, diluants or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

A variety of administration routes are available. The particular mode selected will depend, of course, upon the particular adjuvants or antigen selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are discussed above.

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories. For treatment of a patient, depending on activity of the compound, manner of administration, purpose of the immunization (i.e., prophylactic or therapeutic), nature and severity of the disorder, age and body weight of the patient, different doses may be necessary. The administration of a given dose can be carried out both by single administration in the form of an individual dose unit or else several smaller dose units.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer-based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

As used herein, a method which calls for administration of IFN-α refers to a clinical method for treating a subject by administration of IFN-α with the aim of achieving a desired therapeutic result. There are a number of clinical indications for which IFN-α is an established therapeutic agent. A subject in need of IFN-α treatment has a clinical indication for which IFN-α is an established therapeutic agent. These clinical indications include certain viral infections and certain proliferative disorders, notably cancers and pre-cancerous conditions. The viral infections for which IFN-α has current approval for use in the United States are hepatitis B, hepatitis C, and condylomata acuminata (venereal or anogenital warts). The neoplasms for which IFN-α has current approval for use in the United States are hairy cell leukemia, cutaneous T-cell leukemia, chronic myelogenous leukemia (CML), non-Hodgkin's lymphoma, malignant melanoma, and AIDS-related Kaposi's sarcoma. Outside of the United States, IFN-α is also in clinical use for bladder cell carcinoma, colon carcinoma, renal cell carcinoma, multiple myeloma, cervical dysplasia, and laryngeal papillomatosis. Other indications under investigation for IFN-α treatment include other viral infections and other cancers, including, for example, Behçet's disease, HIV, prostate cancer, small cell lung cancer, pancreatic cancer, squamous cell carcinoma, glioma, and malignant pleural mesothelioma, among others.

As used herein, a pharmaceutical composition comprising IFN-α refers to a preparation of recombinant or natural IFN-α suitable for pharmaceutical use. IFN-α may be derived from natural material (e.g., leukocytes, myeloblasts, lymphocytes) or material derived therefrom (e.g., cell lines), or those prepared with recombinant DNA technology. Details of the cloning of IFN-α and the direct expression thereof, especially in *Escherichia coli*, have been the subject of many publications. The preparation of recombinant IFNs is known, for example, from Gray et al. *Nature* 295:503-8 (1982), Goeddel et al. *Nature* 284:316-20 (1980), Goeddel et al. *Nature* 290:20-26 (1981), and EP 174143. In the United States IFN-α is available as recombinant human IFN-α2a (ROFERON-A), recombinant human IFN-α2b (INTRON A), and as purified natural IFN-αn3 (ALFERON N). Outside the United States, IFN-α is also available as purified natural IFN-αn1 (WELLFERON).

As used herein, a clinically established effective dose for IFN-α alone refers to a dose of recombinant or natural IFN-α, administered in the absence of another agent that increases IFN-α bioavailability, that is the standard recommended dose for a particular clinical indication. A clinically established effective dose for IFN-α alone can encompass, however, the use of IFN-α in combination with other agents and treatment modalities, such as conventional chemotherapy, radiation therapy, antiviral agents, and surgery. In a majority of subjects the standard recommended dose of IFN-α for a particular clinical indication would be expected to exert a desired clinical effect. In a given clinical application in a given subject, a clinically established effective dose for IFN-α alone can also refer to a dose of IFN that is, or has been, or would be expected to be effective in that subject for treating a condition of the subject. For example, a subject might be responsive to a dose of IFN-α alone that is less than the standard recommended dose. Conversely, a subject might be unable to tolerate a clinically established effective dose due to actual or anticipated side effects of the IFN-α treatment.

The maximum tolerated dose (MTD) for any therapeutic compound is identified as part of its clinical evaluation. For example, phase I trials can include a determination of the maximum tolerated dose, dose-limiting toxicities (DLT) and pharmacokinetics of a test compound. Thus, the MTD for any Food and Drug Administration (FDA) approved therapeutic compound is known to those of ordinary skill in the art as a matter of the public record. The MTD for any particular therapeutic compound may vary according to its formulation (e.g., injectable formulation, implantable bioerodible polymer formulation, oral formulation), route of delivery (e.g., intravenous, oral, intratumoral), manner of delivery (e.g., infusion, bolus injection), dosing schedule (e.g., hourly, daily, weekly) and the like. MTD frequently is defined as the highest dose level at which 50 percent of subjects administered with the drug develop a dose-limiting toxicity. Other definitions which are clinically relevant and generally accepted will be known to one of ordinary skill in the art.

Examples of MTD for various types of IFN-a have been published in studies involving various routes of administration, indications, combinations with other agents, and clinical settings. In one study the MTD of recombinant IFN-α2a was 18 million international units (IU) when given intramuscularly three times weekly in combination with phototherapy for treatment of cutaneous T-cell lymphoma (mycosis fungoides and Sézary syndrome). Kuzel T M et al. *J Natl Cancer Inst* 82:203-7 (1990). In an independent study, the MTD of IFN-α2b for the treatment of cutaneous T-cell lymphoma was found to be 18 million IU given intramuscularly three times a week. Qiu B and Chen M *Chin Med J* (Engl) 109:404-6 (1996). The MTD for IFN-α2a was lower, 3 million IU subcutaneously three times a week, for patients undergoing high dose pelvic radiation for rectal cancer. Perera F et al. *Int J Radiat Oncol Biol Phys* 37:297-303 (1997). The MTD for IFN-α2b was 10 million IU daily for patients with AIDS-related Kaposi's sarcoma following cytotoxic chemotherapy. Gill P S et al. *J Biol Response Mod* 9:512-6 (1990). In yet another study the MTD of IFN-α2b was 18 million IU/m$^2$ given weekly as a 24-hour infusion in combination with 5-fluorouracil and leucovorin to patients with metastatic colorectal cancer. Cascinu S et al. *Anticancer Drugs* 7:520-4 (1996).

Measurement of maximum tolerated dose may be expressed as weight of drug per weight of subject, weight of drug per body surface area, etc. The MTD of anticancer compounds is frequently expressed as weight per square meters (mg/m$^2$) of body surface area. MTD also may be expressed as a dose relative to a time component, such as weight of drug per body surface area per day.

For therapeutics which have not yet been subjected to human clinical trials, or subjected to any determination of the MTD in humans (e.g., experimental or highly toxic compounds), one of skill in the art can estimate the MTD by using animal models. Calculation of MTD in animals may be based on a number of physiological parameters, such as death, particular toxicities, and drug-induced weight loss. Using death as an endpoint, the MTD may be the highest dose given test animals in which each member of the test group survived. Using toxicity as an endpoint, the MTD may be the dose at which moderate but not severe toxicity is observed. Using weight loss as an endpoint, the MTD may be the dose above which a certain percent change in body weight is induced.

Other methods for determining MTDs using animal models and various endpoints are known to one of ordinary skill in the art. Correlation of animal MTDs to human MTDs for a therapeutic compound is an accepted practice in the pharmaceutical arts.

Thus the invention in one aspect provides compositions and formulations for administration to a subject, preferably a human subject, containing an amount of interferon which is below the maximum tolerated dose for interferon.

In one aspect of the invention, an improved method is provided for treating a subject in need of treatment with IFN-α which entails coadministration of an effective amount of an isolated ISNA in conjunction with administration of IFN-α. As used herein, an effective amount of an isolated ISNA refers to that amount of an isolated ISNA that causes cells to produce IFN-α. In one preferred embodiment an effective amount of an isolated ISNA refers to that amount of an isolated ISNA that causes cells in vivo to produce IFN-α. In another preferred embodiment an effective amount of an isolated ISNA refers to that amount of an isolated ISNA corresponding to an amount that causes cells in vitro to produce IFN-α. In another preferred embodiment an effective amount of an isolated ISNA refers to that amount of an isolated ISNA that causes an increase in the local or circulating amount of IFN-α above the corresponding level which would occur only from the administration of exogenous IFN-α. In another preferred embodiment an effective amount of an isolated ISNA refers to that amount of an isolated ISNA that increases the therapeutic benefit of exogenous IFN-α above that which would be obtained without the ISNA. In yet another embodiment an effective amount of an isolated ISNA refers to that amount of an isolated ISNA that would allow the same therapeutic effect to be achieved for a given amount of IFN-α when the oligonucleotide is coadministered with a lower dose of IFN-α.

As used herein, the term coadminister refers to administering at least two agents in clinical association with one another. Coadministration can include administering the at least two agents together or sequentially. In a preferred embodiment, ISNA is administered either before, at the same time as, or after administering IFN-α, provided the local or systemic concentration of IFN-α is increased over the corresponding concentration of IFN-α that would be achieved by administering the same amount of IFN-α alone. Coadminister means the administration of interferon-α close enough in time to the administration of the ISNA such that their effects are more than the effects that would be achieved if administering either one on its own at the same dose. Preferably, the effects are at least additive. They also may be administered via different modes, for example such as administering the interferon systemically and administering the ISNA locally.

In certain embodiments involving simultaneous coadministration, the IFN-α and the ISNA may be prepared as a single formulation. In other embodiments involving simultaneous coadministration, the IFN-α and the ISNA may be prepared and administered separately. In this latter instance individual IFN-α and ISNA formulations may be packaged together as a kit with instructions for simultaneous administration. Similarly, in embodiments calling for consecutive coadministration, individual IFN-α and ISNA formulations may be packaged together as a kit with instructions for their sequential administration.

As used herein, administered locally refers to administration by a route that achieves a local concentration of IFN-α that exceeds the systemic concentration of IFN-α. For example, local administration to a particular lesion or organ could be accomplished by direct injection into the lesion or organ or by direct injection into an afferent blood vessel associated with and supplying the lesion or organ to be treated. In the example local administration to the liver, local administration can be accomplished by injection or infusion into the hepatic artery, the celiac artery, or the portal vein.

In another aspect, the invention provides a method of supplementing IFN-α treatment of a subject in need of IFN-α treatment wherein an effective amount of IFN-α and an isolated ISNA are both administered to the subject. The IFN-α induced by the ISNA supplements the IFN-α directly administered to the subject, thus extending the clinical efficacy of a given dose of IFN-α. Furthermore, because the ISNA-induced IFN-α typically includes a plurality of subtypes, while the directly administered IFN-α typically includes only a single subtype, the range of biological effects afforded by IFN-α treatment is also expanded by the coadministration of the ISNA and the IFN-α.

The invention also provides a method of increasing the efficacy of IFN-α treatment of a subject. The method according to this aspect of the invention involves administering to a subject in need of treatment with IFN-α a pharmaceutical composition comprising IFN-α and coadministering to the subject in need of such treatment a pharmaceutical composition comprising an ISNA in an amount which, together with the administered IFN-α, is an effective IFN-α treatment, wherein the efficacy of the IFN-α treatment is greater than the efficacy of administering the same amount of IFN-α in the absence of coadministering the ISNA.

As used herein, a method of enhancing efficacy or increasing efficacy of IFN-α treatment of a subject refers to a method in which the effect of administering a given dose of IFN-α to a subject results in a greater clinical effect than expected or previously observed when using that same dose of IFN-α. In a preferred embodiment the method entails coadministering an amount of ISNA in an amount effective for inducing the production of IFN-α by IPCs. The amount of IFN-α achieved locally or systemically in this method reflects contributions both from administered IFN-α and from induced IFN-α, thereby achieving an enhanced efficacy of IFN-α treatment for a given dose of administered IFN-α. The increased efficacy could be manifested as, for example, a greater degree of response to treatment, a more rapid course of response to treatment, or improved compliance with the treatment regimen.

According to another aspect of the invention, a method is provided for decreasing a dose of IFN-α effective for treating a subject in need of treatment with IFN-α. The method involves administering to a subject in need of treatment with IFN-α a pharmaceutical composition comprising IFN-α, and coadministering to the subject in need of such treatment a pharmaceutical composition comprising an immunostimulatory nucleic acid in an amount which, together with the administered IFN-α, is an effective IFN-α treatment, and wherein the amount of administered IFN-α is less than an amount of IFN-α required in the absence of coadministering the immunostimulatory nucleic acid.

As used herein, a method of decreasing a dose of IFN-α effective for treating a subject refers to a method in which IFN-α is administered to a subject in an amount or with a frequency that is reduced compared to a previously established amount or frequency, while achieving a desired clinical effect in treating a condition of the subject. In a preferred embodiment the dose amount can be reduced by a clinically determined extent to an amount that is, for example, at least 10 percent below the customary or maximum tolerated dose of IFN-α alone. In other more preferred embodiments, the IFN-α dose amount can be reduced by a clinically determined extent to an amount that is at least 20 percent, at least 30 percent, or at least 40 percent below the customary or maximum tolerated dose of IFN-α alone. In a most preferred embodiment, the IFN-α dose amount can be reduced by a clinically determined extent to an amount that is at least 50 percent below the customary or maximum tolerated dose of IFN-α alone. In another preferred embodiment the dose frequency can be reduced by a clinically determined extent to a frequency that is, for example, at least 10 percent below the customary or maximum tolerated dose of IFN-α alone. In other more preferred embodiments, the IFN-α dose frequency can be reduced by a clinically determined extent to a frequency that is at least 20 percent, at least 30 percent, or at least 40 percent below the customary or maximum tolerated dose of IFN-α alone. In a most preferred embodiment, the IFN-α dose frequency can be reduced by a clinically determined extent to a frequency that is at least 50 percent below the customary or maximum tolerated dose of IFN-α alone.

Yet another aspect of the invention is a method of preventing an IFN-α treatment-related side effect in a subject receiving or in need of treatment with IFN-α. The method entails administering to a subject in need of treatment with IFN-α a pharmaceutical composition comprising IFN-α and coadministering to the subject in need of such treatment a pharmaceutical composition comprising an immunostimulatory nucleic acid in an amount which, together with the administered IFN-α, is an effective IFN-α treatment, and wherein an IFN-α treatment-related side effect is reduced in comparison to the side effect when IFN-α is administered in the absence of coadministering the immunostimulatory nucleic acid.

Assays for IFN-α are well known in the art. These include direct tests, e.g., enzyme-linked immunosorbent assay (ELISA) specific for at least one IFN-α, and indirect tests, e.g., functional tests including NK cell activation/cytotoxicity (Trinchieri G *Adv Immunol* 47:187-376 (1989) and phenotyping by fluorescence-activated cell sorting (FACS) analysis for class I MHC. Additional specific assay methods well known in the art can be particularly useful in settings where local concentration or local presence of IFN-α is of interest; these methods include, for example, immunohistochemistry, nucleic acid hybridization (e.g., Northern blotting), Western blotting, reverse transcriptase/polymerase chain reaction (RT/PCR), and in situ RT/PCR. A further method, involving detection of intracellular IFN-α by flow cytometry, is disclosed below in Example 6.

As used herein, a method of preventing an IFN-α treatment-related side effect in a subject refers to a method of reducing the incidence or severity of an IFN-α treatment-related side effect experienced by a subject receiving IFN-α treatment. As used herein, an IFN-α treatment-related side effect is a clinical side effect that is induced in a subject as a result of administration of IFN-α to the subject. A number of such side effects have been well documented through clinical experience and clinical trials. Such side effects are frequently dose-limiting in a subject. Systemic IFN-α treatment-related side effects most commonly encountered include: influenza-like syndrome, fever, headache, chills, myalgia, fatigue, anorexia, nausea, vomiting, diarrhea, depression, hypothyroidism, neutropenia, and anemia. In a preferred embodiment the IFN-α treatment-related side effect is reduced sufficiently to promote greater compliance with IFN-α treatment. In another preferred embodiment the IFN-α treatment-related side effect is reduced sufficiently to permit resumption of IFN-α treatment otherwise precluded by the side effect. In another preferred embodiment the IFN-α treatment-related side effect is reduced sufficiently to permit an intensification of IFN-α treatment.

In another aspect of the invention, a second method is provided for enhancing efficacy of IFN-α treatment in a subject in need of such treatment. The method involves the steps of administering to a subject in need of such treatment an amount of a pharmaceutical composition comprising IFN-α effective for treating a condition of the subject, isolating natural interferon-producing cells (IPCs) from a donor, contacting the isolated IPCs ex vivo with an amount of a pharmaceutical composition comprising an immunostimulatory nucleic acid effective for inducing the IPCs to release IFN-α and administering the contacted cells to the subject. The donor and the subject can be a single individual or they can be different individuals. In certain embodiments the contacted cells are administered to the subject in a local fashion, e.g., via injection or infusion into a blood vessel supplying a target tissue to be treated. The method according to this aspect of the invention can optionally include contacting the isolated IPCs with an antigen. In certain embodiments the method may also include contacting the isolated IPCs with a growth factor which the IPCs do not produce themselves. Such a growth factor not produced by IPCs can include, for example, IL-3 or GM-CSF, and would exclude IL-8 and TNF-α.

As used herein, the term growth factor refers to a soluble signaling factor that induces a responsive cell type to undergo maturation and mitosis. Categories of growth factors include a number of cytokines, growth factors per se, and hormones. Specific examples of growth factors include, without limitation, IL-1, IL-2, IL-3, IL-6, GM-CSF, G-CSF, PDGF, TGF-β, NGF, IGFs, growth hormone, erythropoietin, thrombopoietin, and the like. In addition to naturally occurring growth factors, growth factor analogs and growth factor derivatives such as fusion proteins can be used for the purposes of the invention.

As used herein, the term natural interferon-producing cell (IPC) refers to a specialized type of leukocyte that is the chief producer of IFN-α in response to enveloped viruses, bacteria, and tumors. IPCs are lineage negative (lin−)/CD4+/MHC class II+ cells that are present in low frequency in peripheral blood mononuclear cells (PBMCs) and in tonsillar tissue. Siegal F P et al. *Science* 284:1835-7 (1999); Grouard G et al. *J Exp Med* 185:1101-11 (1997). The frequency of IPCs in PBMCs in normal individuals varies between 0.2 and 0.6 percent. They are characterized by the absence of lineage markers CD3 (T cells), CD 14 (monocytes), CD19 (B cells) and CD56 (NK cells), by the absence of CD11c, and by their expression of CD4, CD123 (IL-3 receptor α, IL-3Rα) and MHC class II. Grouard G et al. *J Exp Med* 185:1101-11 (1997); Rissoan M-C et al. *Science* 283:1183-86 (1999); Siegal F P et al. *Science* 284:1835-7 (1999); Cella M et al. *Nat Med* 5:919-23 (1999).

As used herein, isolating IPCs from a subject refers to a process of removing from the subject a body fluid or tissue containing IPCs and enriching for the IPCs from the body fluid or tissue to an extent that at least 1 percent of the cells are IPCs. In a most preferred embodiment at least 99 percent of cells are IPCs. In another preferred embodiment at least 95 percent of cells are IPCs. In another preferred embodiment at least 90 percent of cells are IPCs. In another preferred embodiment at least 80 percent of cells are IPCs. In another preferred embodiment at least 70 percent of cells are IPCs. In another preferred embodiment at least 60 percent of cells are IPCs. In another preferred embodiment at least 50 percent of cells are IPCs. In another preferred embodiment at least 40 percent of cells are IPCs. In another preferred embodiment at least 30 percent of cells are IPCs. In another preferred embodiment at least 20 percent of cells are IPCs. In another preferred embodiment at least 10 percent of cells are IPCs. In another preferred embodiment at least 5 percent of cells are IPCs. The enriching can be achieved by a series of selecting steps which can include, for example, a negative selection of lineage-positive cells by contacting cells with magnetic beads conjugated with antibodies specific for lineage markers (i.e., anti-CD3, anti-CD11c, anti-CD14, anti-CD16, anti-CD19, anti-CD56) and then passing the contacted cells over a depletion column in the presence of a strong magnetic field; a positive selection step involving contacting the cells passing through the depletion column with microbead-conjugated anti-CD4 and passing the contacted cells over a positive selection column; and further enhancement for IPCs by fluorescence-activated cell sorting (FACS) using anti-CD 123 and anti-MHC class II. Other methods can be employed to equal effect, as will be appreciated by those skilled in the art, provided they result in the isolation or enrichment of (lin–)/CD4+/CD123+/MHC class II+ interferon producing cells to an extent that at least 1 percent of the viable cells are IPCs.

In yet another aspect of the invention, a method is provided for supporting the survival of natural interferon-producing cells (IPCs) in vitro. The method involves isolating IPCs from a subject (as described above), culturing the IPCs in a sterile medium suitable for tissue culture, and contacting the IPCs in vitro with an amount of immunostimulatory nucleic acid effective to support the growth of the IPCs in the absence of interleukin 3 (IL-3). In a preferred embodiment, the IPCs are precursor type 2 dendritic cells (pDC2s; plasmacytoid monocytes). Siegal F P et al. *Science* 284:1835-7 (1999). The IPCs can be cultured under suitable tissue culture conditions either with or, more notably, without exogenous IL-3 and/or GM-CSF.

As used herein, a method of supporting survival of interferon-producing cells (IPCs) in vitro refers to providing a factor or inducing a signal that promotes the viability of IPCs placed in in vitro culture. For example, in the absence of IL-3, normally most IPCs die within three days of being placed into cell culture. Addition of IL-3 to IPCs will support the survival of IPCs in culture. According to this aspect of the invention, IL-3 is not required for IPC survival in vitro if the IPCs are contacted with an effective amount of ISNA.

The invention in another aspect provides a method for stimulating isolated interferon-producing cells (IPCs) in vitro. The method includes the steps of isolating IPCs from a subject (described above), culturing the IPCs in a sterile medium suitable for tissue culture, and contacting the IPCs in vitro with an amount of immunostimulatory nucleic acid effective to induce secretion of at least one type I interferon. In a preferred embodiment the type I interferon induced by the method is IFN-α. As described above, preferred IPCs are precursor type 2 dendritic cells (pDC2s; plasmacytoid monocytes). Siegal F P et al. *Science* 284:1835-7 (1999). Importantly, the IPCs can be stimulated in culture in the absence of GM-CSF and without viral infection by, e.g., Sendai virus, HSV or influenza virus. Activation can be assayed using methods well known in the art, including FACS analysis of the cell surface activation marker CD80 and ELISA or bioassay (e.g., protection of fibroblasts against vesicular stomatitis virus) for type I IFN.

As used herein, a method of stimulating isolated interferon-producing cells (IPCs) in vitro refers to providing a factor or inducing a signal that results in a change in IPC size, morphology, or expression of a cell surface antigen, transcript, or a secreted product that is not characteristic of IPCs in the absence of the factor or signal. Freshly isolated IPCs, in the absence of a signal provided by viral infection, CD40L ligation, or GM-CSF, display a smooth round lymphoid morphology with a diameter of 8-10 μm and do not express CD80 or CD86 on their cell surface. Grouard G et al. *J Exp Med* 185:1101-11 (1999). Similarly, freshly isolated IPCs do not secrete IFN-α in large amounts. Siegal F P et al. *Science* 284:1835-7 (1999). In contrast, IPCs exposed to IL-3 in vitro develop pseudopods and a veiled morphology, express CD80 and CD86 on their surface, and secrete large amounts of type I IFN (IFN-α and IFN-β) when exposed to ultraviolet-irradiated herpes simplex virus, Sendai virus, or heat-killed *Staphylococcus aureus*. Grouard G et al. *J Exp Med* 185:1101-11 (1999); Siegal F P et al. *Science* 284:1835-7 (1999). According to this aspect of the invention, ISNA can be used in place of viral infection, CD40L ligation, or GM-CSF to induce a signal effective for stimulating isolated IPCs in vitro.

The invention further provides a method for treating a subject to activate interferon-producing cells (IPCs) of the subject. The method involves isolating IPCs from a subject in need of such treatment, culturing the IPCs in vitro, contacting the IPCs in vitro with an effective amount of an isolated immunostimulatory nucleic acid, and returning the contacted IPCs to the subject. IPCs are isolated from a subject as described above and placed into culture under suitable in vitro cell culture conditions. Such culture conditions may optionally include provision of exogenous growth factor, including IL-3 or GM-CSF. However, IL-3 or GM-CSF may not be required for the purposes of the method. According to this method, the subject may be treated without direct administration of a pharmaceutical preparation of IFN-α. Activation of the IPCs can be assayed as described above, with reference made to IPCs similarly obtained and cultured but not contacted with ISNA.

In yet another aspect, the invention provides a method for stimulating production of a plurality of type I IFN subtypes. The method involves contacting IPCs with an amount of immunostimulatory nucleic acid effective to induce secretion of at least two type I interferons. In one embodiment the IPCs are brought into contact with ISNA in vivo. In another embodiments the IPCs are isolated and/or are contacted with ISNA in vitro under suitable cell culture conditions. Various other embodiments result in the induction of at least three, at least four, at least five, at least six, at least seven, and at least eight subtypes of type I IFN. The various subtypes can be determined using methods well described in the art and known to those of skill in the art, e.g., subtype-specific ELISA, amino-terminal sequencing, and mass spectrometry (MS).

Matrix-assisted laser desorption/ionization time-of-flight (MALDI TOF)-MS and electrospray ionization (ESI)-MS are now standard methods used for identifying peptides available in femtomole quantities. Mann M and Talbo G *Curr Opin Biotechnol* 7:11-19 (1996); Mann M and Wilm M *Trends Biochem Sci* 20:219-24 (1995); Mann M et al. *Anal Chem* 61:1702-8 (1989). Individual bands were cut out of the polyacrylamide gel, cleaved with trypsin and then eluted to yield peptide fragments that are subjected to MALDI TOF-MS or ESI-MS analysis. The combination of mass/charge data from the MS, cleavage site specificity of the trypsin digest, and peptide sequence data permitted identification of individual proteins and peptides. MALDI TOF-MS analysis gives a mass fingerprint of the cleaved and analyzed proteins. The fingerprint is useful only for scanning against a database of calculated peptide masses corresponding to fully sequenced proteins. The ESI-MS analysis is more difficult, but it permits identification based on comparison to either complete or partial sequence data. Mass accuracies for either method can exceed 0.01 percent, i.e., 1 Da per 10 kDa.

In another aspect the invention relates to the discovery that type I IFN induces activation and proliferation of γδ T cells. The γδ T cells are antigen-specific T cells in a preactivated stage which respond to common phosphate-containing non-peptide antigens. Examples of γδ T cell antigens include phosphate-containing non-peptide molecules from heat-killed mycobacteria; isopentenyl pyrophosphate (IPP) and related prenyl pyrophosphate derivatives; monoethyl phosphate; and γ-monoethyl derivatives of nucleoside and deoxynucleoside triphosphates. Tanaka Y et al. *Nature* 375:155-8 (1995). Previous studies showed that γδ T cells can secrete a variety of lymphockines and mount cytolytic responses. For example, exposure of γδ T cells to these phosphate-containing non-peptide antigens stimulates IFN-γ production in the absence of APC. While clearly belonging to the T-cell lineage, human γδ T cells are distinctly different from α/β T cells, and they share several features with NK cells. The observations that γδ cells accumulate in lesions caused by mycobacterial infections, respond to virally infected cells in a virus-nonspecific manner, require neither antigen-processing nor antigen-presenting cells, and that they are preferentially located in various epithelia, together suggest that γδ cells may be responsive to pattern recognition and responsible for a first line of defense.

It was discovered according to this aspect of the invention that CpG ODN in combination with IPP synergistically induced activation of human γδ T cells present within PBMC, as measured by the production of IFN-γ and perforin. In addition, it was also discovered according to this aspect of the invention that CpG ODN in combination with IPP synergistically induced proliferation of human γδ T cells present within PBMC. These effects were abrogated by isolating γδ T cells from PBMC or by addition of neutralizing antibodies to type I IFN, and they were reproduced by the addition of recombinant type I IFN. Notably, ODN 2216 and 1585, both strong inducers of type I IFN, were more potent in their effects on γδ T cells than ODN 2006.

In humans Th1 responses are driven by IL-12 and/or IFN-γ. IL-12 and IFN-γ/δ both promote IFN-γ synthesis in T cells and NK cells. It was previously known that IL-12 promotes γδ T cells to secrete IFN-γ. Since IFN-β has been described to downregulate IL-12 production, experiments were performed to study the effect on IL-12 production exerted by ISNA which induce type I IFN. The results of these experiments (Example 13) demonstrate that certain CpG ODN suppress CD40-dependent IL-12p70 production by an IFN-α/β-mediated negative feedback mechanism on IL-12p40 mRNA production. Thus the interaction of T cells and antigen-presenting cells via CD40L leads to a cytokine milieu dominated by IL-12 or IFN-α/β. Although both promote Th1 responses, CpG ODN which are better inducers of B cell activation than of type I IFN may be superior for priming naive T cells, and conversely CpG ODN which are strong inducers of type I IFN may have higher activity to support preactivated and memory T cells.

According to another aspect of the invention, an interferon composition for administration to a subject is provided. The composition includes recombinant or natural interferon in a container for administration to a subject. The amount of the interferon in the container is at least about 10 percent less than the maximum tolerated dose (MTD). Preferably the amount of interferon in the container is at least about 20 percent below the MTD, at least 30 percent below the MTD, at least 40 percent below the MTD, or even at least 50 percent below the MTD. In other embodiments, the amount of interferon in the container is at least about 20 percent below, 30 percent below, 40 percent below, or even 50 percent below the clinically established effective dose. The container also can include an ISNA.

Figure 18:
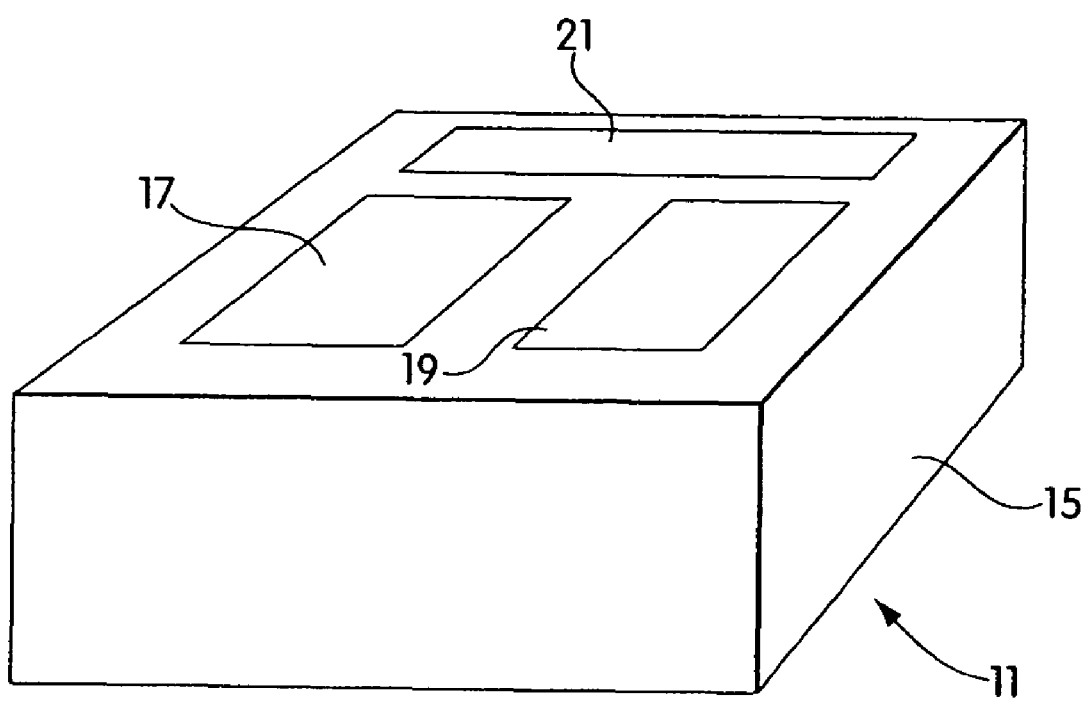
FIG. 18 is a schematic representation of a kit which includes a container containing a composition which includes IFN-α in an amount which is at least about 10 percent less than the maximum tolerated dose (MTD) and, in the same container or in a separate container, an ISNA. The kit also can include instructions for treating a subject with a condition susceptible to treatment with IFN-α.

In still another aspect of the invention, kits for administration of interferon and an ISNA to a subject are provided. Referring to FIG. 18 depicting a kit 11, the kits include a container 19 containing a composition 17 which includes IFN-α and instructions 21 for administering the interferon to a subject in need of such treatment in an amount which is at least about 10 percent less than the maximum tolerated dose (MTD), 20 percent less than the MTD, 30 percent less than the MTD, 40 percent less than the MTD, or 50 percent less than the MTD. The kit 11 can include, in the same container or in a separate container 19, an ISNA. The kit also can include instructions 21 for treating a subject with a condition susceptible to treatment with IFN-α. Examples of such conditions, proliferative and viral, are as described above. Kit 11 also includes a box-like package 15.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Isolation and Characterization of IPCs

Peripheral blood mononuclear cells (PBMCS) contain a total of 0.2 to 0.4 percent IPCs, which are characterized by the lack of lineage markers (CD3, CD 14, CD16, CD19, CD20, CD56) and can be distinguished from other lineage-negative cells by the expression of CD4, CD123 (IL-3Rα), and MHC class II.

IPCs were isolated from peripheral blood by using the VARIOMACS technique (Milteny Biotec, Auburn, Calif.) and the technique previously described. O'Doherty U et al. *J Exp Med* 178:1067-76 (1993). PBMCs were obtained from buffy coats of healthy blood donors by Ficoll-Paque density gradient centrifugation (Histopaque-1077, Sigma) as previously described. Hartmann G et al. *Antisense Nucleic Acid Drug Dev* 6:291-9 (1996). Monoclonal antibodies directed to CD3 (UCHT1), CD14 (M5E2), and CD19 (B43) were purchased from PharMingen (San Diego). PBMCs were incubated with anti-CD3, CD14, CD16, CD19, and CD56 antibodies conjugated to colloidal superparamagnetic microbeads and passed over a depletion column in a strong magnetic field. Resulting lineage-negative (lin–) cells in the flow-through were incubated with a microbead-conjugated antibody to CD4 and passed over a positive selection column. Further purification of IPCs to >99 percent from lin–/CD4+ cells was achieved by fluorescence-activated cell sorting (FACS) using phycoerythrin (PE)-labeled anti-CD123 and FITC-labeled anti-MHC class II.

Surface antigen staining was performed as previously described. Hartmann G et al. *J Pharmacol Exp Ther* 285: 920-8 (1998). Monoclonal antibodies to MHC class II (HLA-DR, Immun-357) and CD80 (MAB104) were purchased from Immunotech (Marseilles, France). All other antibodies were purchased from PharMingen (San Diego): mAbs to CD3 (UCHT1), CD14 (M5E2), CD19 (B43), and CD86 (2331 (FUN-1)). FITC-labeled IgG1,κ (MOPC-21) and phycoerythrin-labeled IgG2b,κ were used to control for specific staining. Lyons A B and Parish C R *J Immunol Methods* 171:131-7 (1994).

Flow cytometric data were acquired on a FACScan (Becton Dickinson Immunocytometry Systems, San Jose, Calif.). Spectral overlap was corrected by appropriate compensation. Analysis was performed on viable cells within a morphologic gate (forward scattering (FSC), side scattering (SSC), >94 percent of cells MHC class II positive and lineage marker negative). Data were analyzed with the computer program FLOWJO (version 2.5.1, Tree Star, Stanford, Calif.).

Results. Viability as determined by trypan blue exclusion was >95 percent. Freshly isolated IPCs are negative for costimulatory molecules CD80 and CD86. FIG. 1 depicts FACS analyses of IPCs isolated from PBMCs with magnetic beads and flow cytometry. From left to right are shown: selection of lin–/MHC class II+ cells from PBMCs; further selection of CD123+/MHC class II+ cells from lin–/MHC class II+ cells; and characterization of freshly isolated lin–/MHC class II+/CD123+ IPCs as CD80–.

Example 2

CpG Oligonucleotide Supports the Survival and Activation of IPCs In Vitro

The majority of freshly isolated IPCs die within 3 days if not incubated in the presence of IL-3 or GM-CSF. Remaining live cells are not activated or are only weakly activated. If CpG oligonucleotide but no other growth factors are added to the cell culture of IPCs, IPCs survive and become highly activated as shown by their increased expression of costimulatory molecules (e.g., CD80, FIG. 2).

Freshly isolated IPCs (see Example 1) were suspended in RPMI 1640 culture medium supplemented with 10 percent (vol/vol) heat-inactivated (56° C., 1 h) FCS (HyClone), 1.5 mM L-glutamine, 100 units/ml penicillin, and 100 µg/ml streptomycin (all from GIBCO/BRL) (complete medium). All compounds were purchased endotoxin-tested. Freshly prepared IPCs (final concentration $5\times10^5$ cells per ml) were cultured for two days in complete medium alone or complete medium supplemented with 6 µg/ml phosphorothioate CpG ODN 2006 (5'-tcgtcgttttgtcgttttgtcgtt-3'; SEQ ID NO:147), 100 ng/ml LPS (from *Salmonella typhimurium*, Sigma catalog no. L2262), 800 units/ml GM-CSF ($1.25\times10^4$ units/mg, Genzyme), or CpG oligonucleotide in combination with GM-CSF. Expression of CD80 and MHC class II on IPCs was examined by flow cytometry (see Example 1).

Figure 2:
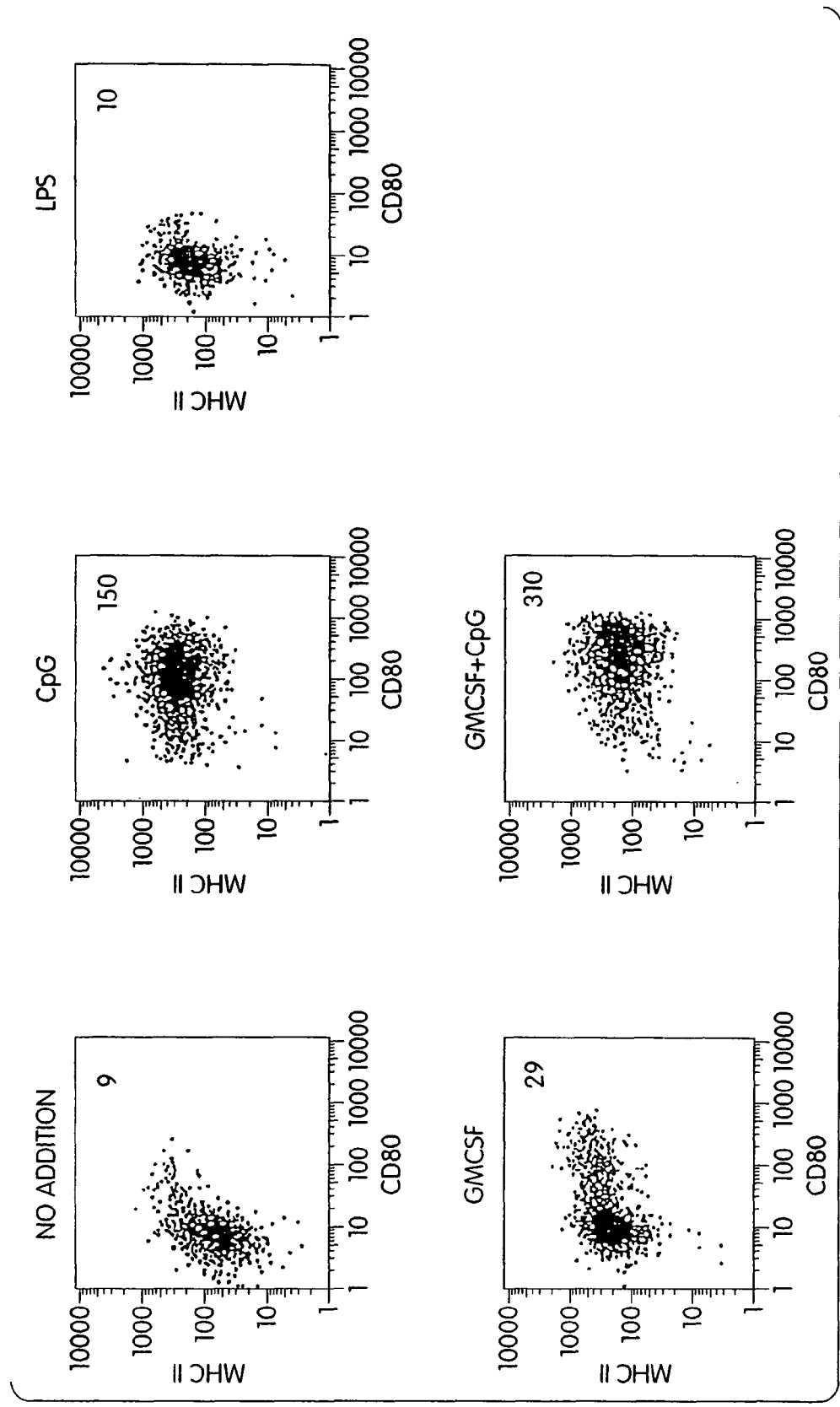
FIG. 2 depicts FACS analyses of survival and activation (CD80) of freshly isolated IPCs after incubation for two days in the presence of selected growth factors and stimuli. Growth factor (GM-CSF) and/or stimulus (CpG oligonucleotide or LPS) for each panel: top left, none; top middle, CpG oligonucleotide; top right, LPS; bottom left, GM-CSF; and bottom middle, GM-CSF plus CpG oligonucleotide. The number in the upper right corner of each panel is the mean fluorescence intensity (MFI) for CD80. Results are representative of five independent experiments.

Results. Representative results of five independent experiments are depicted in FIG. 2. A single addition of CpG ODN 2006 (SEQ ID NO:147, 2 µg/ml) to freshly prepared IPCs was superior to GM-CSF (800 units/ml) in promoting cell survival (74.3 percent±5.2 percent vs. 57.1 percent±2.3 percent). The combination of GM-CSF and CpG ODN 2006 (SEQ ID NO:147) further increased the number of viable cells (81.0 percent±6.7 percent). Freshly isolated IPCs placed into culture for two days without IL-3 or GM-CSF remained unactivated, as indicated by the lack of staining for CD80, even when LPS was added to the media. Addition of GM-CSF induced CD80. Addition of CpG ODN 2006 (SEQ ID NO:147, 6 µg/ml) activated IPCs to an even greater degree than GM-CSF (800 units/ml). Further activation of IPCs occurred when GM-CSF and CpG oligonucleotide were present together. This demonstrates that CpG substitutes for IL-3 and GM-CSF in supporting the survival of IPCs. LPS did not contribute either to survival or activation of IPCs (FIG. 2).

Example 3

CpG Oligonucleotide, but not Poly IC, Activates IPCs In Vitro

Figure 3:
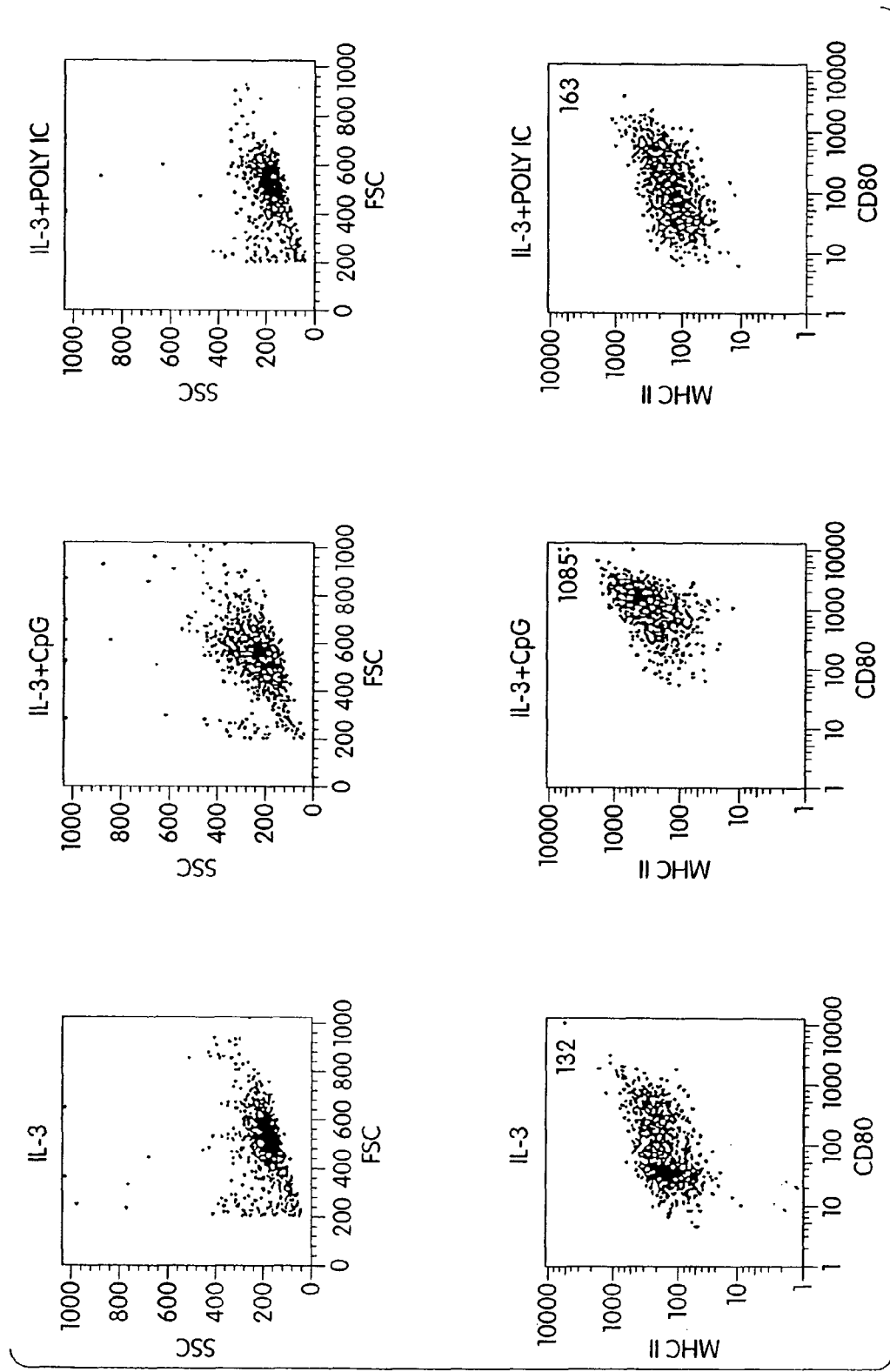
FIG. 3 depicts FACS analyses showing the different effects CpG and poly IC have on the survival and activation of freshly isolated IPCs. All cells were cultured for three days in the presence of IL-3. Cells were then cultured for an additional 24 hours with the addition of: nothing (left panels); CpG (middle panels); or poly IC (right panels). MFI for CD80 is shown in the top right of each of the bottom panels. Results are representative of three independent experiments.

IL-3 provides excellent survival of IPCs but does not activate IPCs. When IL-3 was combined with CpG oligonucleotide, expression of CD80 increased by 5 to 20-fold (FIG. 3). Poly IC, another polynucleotide with well known immunostimulatory functions on myeloid cells (dendritic cells, macrophages), did not stimulate IPCs.

Freshly prepared IPCs (see Example 1, final concentration $3\times10^5$ cells per ml) were cultured for three days in complete medium (see Example 2) supplemented with 10 ng/ml IL-3. Cultures of IPCs were then continued for a further 24 hours (a) without any additional supplements, (b) following the addition of 6 µg/ml CpG ODN 2006 (SEQ ID NO:147), and (c) following the addition of 10 µg/ml poly IC. Forward scattering (FSC), side scattering (SSC), and expression of CD80 and MHC class II on IPCs were examined by flow cytometry (see Example 1).

Results. Representative results of three independent experiments are shown in FIG. 3. IPCs cultured in complete media supplemented with IL-3 and CpG ODN 2006 (SEQ ID NO:147, 6 µg/ml) were larger and more granular than IPCs cultured in complete media containing IL-3 alone or in complete media supplemented with IL-3 and poly IC. In addition, IPCs cultured in complete media supplemented with IL-3 and CpG ODN 2006 (SEQ ID NO:147, 6 µg/ml) were more highly activated than IPCs cultured in complete media containing IL-3 alone or in complete media supplemented with IL-3 and poly IC. This demonstrates that CpG oligonucleotide activates IPCs in vitro.

Example 4

CpG Oligonucleotide Induces IFN-α Production by IPCs

Induction of type I interferons by CpG in whole PBMC has been previously demonstrated. Sun S et al. *J Exp Med* 188: 2335-42 (1998). Here is shown for the first time that IFN-α is induced in IPCs by CpG oligonucleotide within 48 hours using an ELISA specific for 9 out of 10 subspecies of IFN-α tested.

Freshly prepared IPCs (see Example 1, final concentration $3\times10^5$ cells per ml) were cultured for two days in complete medium (see Example 2) supplemented with 10 ng/ml IL-3 and 800 units/ml GM-CSF ($1.25\times10^4$ units/mg, Genzyme). Half of the cultures were supplemented with 6 µg/ml CpG ODN 2006 (SEQ ID NO:147). IFN-α was measured in the supernatant using a combination of separate ELISAs specific for IFN-α (human IFN-α multispecies ELISA, PBL Biomedical Laboratories, New Brunswick, N.J.) and for IFN-β (PBL Biomedical Laboratories, New Brunswick, N.J.) performed according to the supplier's instructions. The multispecies IFN-α ELISA has a range from 100 to 5000 pg/ml, detects all of the human IFN-α subtypes except IFN-αF, and does not detect IFN-β or IFN-γ. The IFN-β ELISA has a range of 250-10,000 pg/ml.

Figure 4:
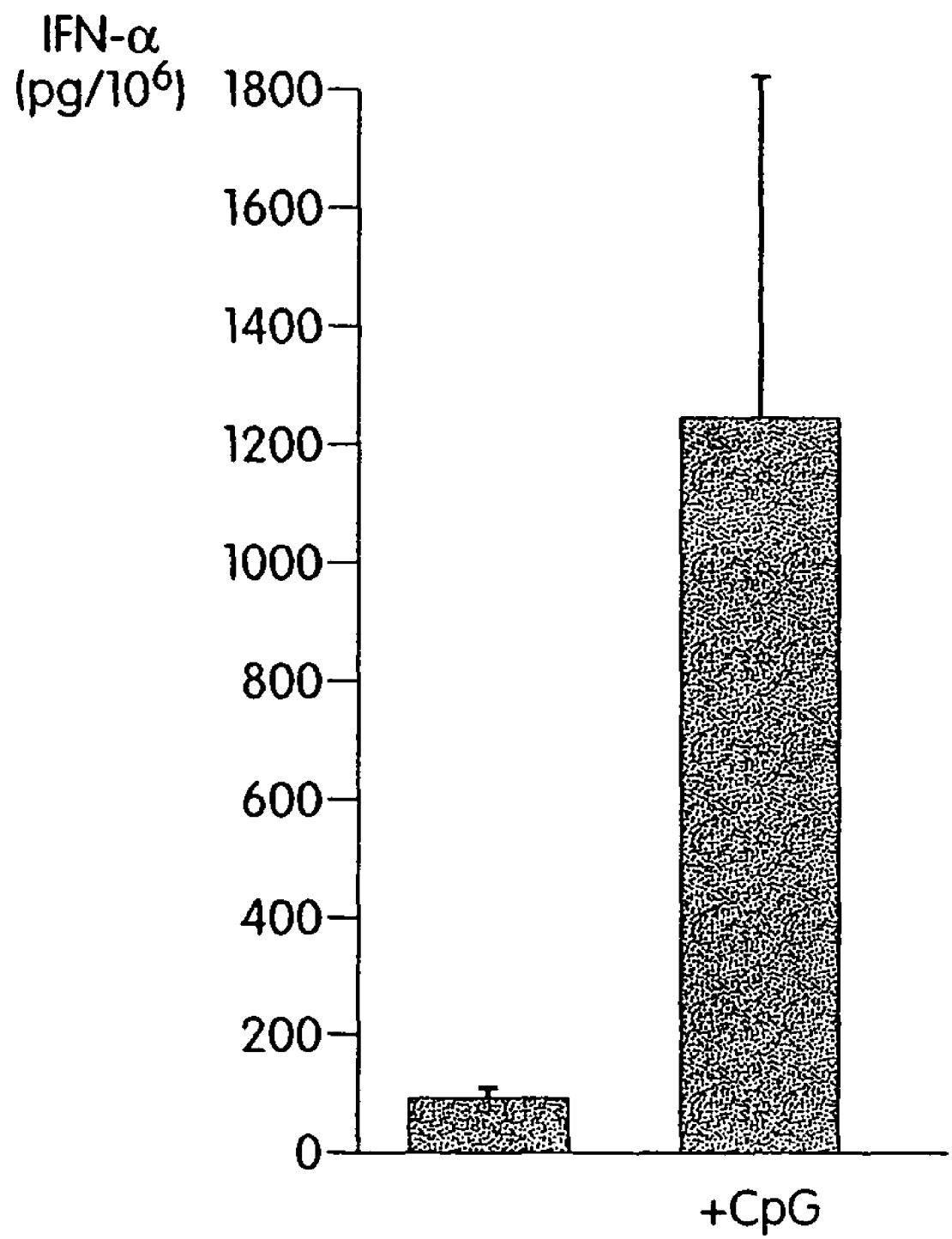
FIG. 4 is a graph depicting the concentration of IFN-α (determined by IFN-α-specific ELISA) present in the supernatant of IPCs cultured for two days in the presence of IL-3 and GM-CSF, either with CpG oligonucleotide (solid bar) or without CpG oligonucleotide (open bar). Results are representative of three independent experiments.

Results. Representative results of three independent experiments appear in FIG. 4. IPCs cultured for 48 hours in complete media supplemented with 10 ng/ml IL-3, 800 units/ml GM-CSF and 6 µg/ml CpG ODN 2006 (SEQ ID NO:147) were strongly induced to secrete IFN-α compared to similar cultures without added CpG oligonucleotide. This result demonstrates CpG oligonucleotide induces human IPCs to secrete multiple subspecies of IFN-α. This result also indicates CpG oligonucleotide would permit the in vitro production of natural interferons using a permanent cell line derived from IPCs.

Example 5

Identification of CpG ODN with IFN-α and IFN-β Inducing Activity

The 24mer CpG ODN 2006 (SEQ ID NO:147) which contains three consecutive "human" CpG motifs (5' GTCGTT 3') is one of the most potent CpG sequences to activate human B cells. Hartmann G et al. *J Immunol* 164: 944-53 (2000); Hartmann G et al. *J Immunol* 164:1617-24 (2000). In contrast to other microbial stimuli such as LPS and poly (I:C), ODN 2006 strongly promotes survival and activation of pDC precursors. However, compared to its strong ability to activate NK cells, the ability of ODN 2006 to induce type I IFN in pDC is relatively poor.

In order to test the hypothesis that other CpG ODN may activate NK cells by inducing type I IFN in pDC, a panel of CpG ODN with known NK cell activity were tested for their capability to stimulate IFN-α production in PBMC. The panel of CpG ODN included the following, where lower case letters signify phosphorothioate linkages, upper case letters signify phosphodiester linkages, and m signifies 7-deaza-guanosine:

| | |
|---|---|
| tcgtcgttttgtcgttttgtcgtt | ODN 2006 (SEQ ID NO:147) |
| ggGGTCAACGTTGAgggggG | ODN 1585 (SEQ ID NO:1) |
| gmGGTCAACGTTGAgggmggG | ODN 2197 (SEQ ID NO:148) |
| ggGGAGTTCGTTGAgggggG | ODN 2198 (SEQ ID NO:149) |

All ODN were dissolved in TE buffer (10 mM Tris-HCl, 1 mM EDTA, pH 8) at a concentration of 20 mg/ml. Aliquots diluted in PBS (0.4 mg/ml) were stored at −20° C. and thawed prior to use. Pyrogen-free reagents were used for all dilutions. ODN were tested for endotoxin using the LAL assay (Bio-Whittaker, Walkersville, Md.; lower detection limit 0.1 EU/ml).

Figure 5:
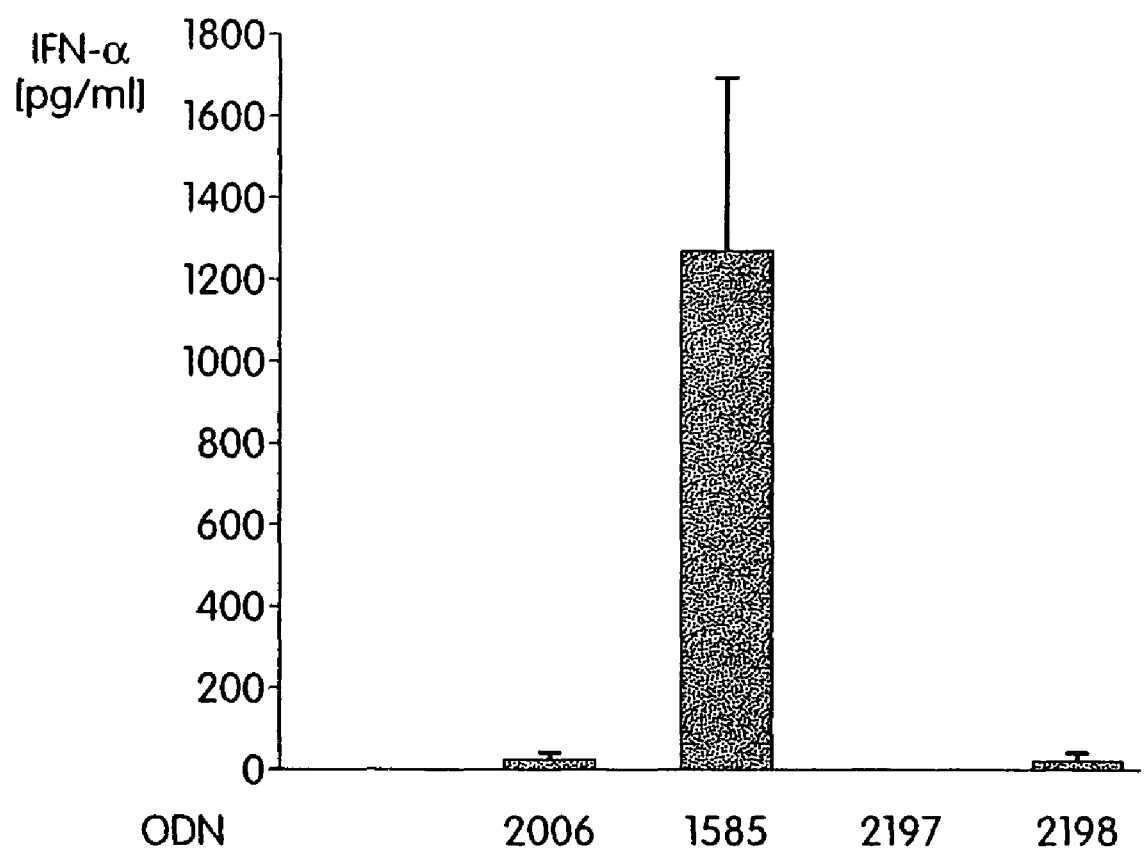
FIG. 5 is a graph depicting the concentration of IFN-A induced in the supernatants of PBMC from different donors following incubation for 48 hours in the presence of 3 μM ODN 2006 (n=7), 1585 (n=7), 2197 (n=6), 2198 (n=5), or media without added ODN (n=7). Error bars indicate SEM.

Freshly isolated PBMC were incubated with CpG ODN (3 µg/ml) for 48 hours. IFN-α was measured in the supernatant by an ELISA which detects 10 of 13 isoforms of IFN-α. Among all sequences initially examined, CpG ODN 1585 (SEQ ID NO:1) showed the highest activity to induce IFN-α in PBMC. ODN 1585 is a chimeric ODN (mixed phosphorothioate-phosphodiester backbone) with poly G on both ends and a central CpG-dinucleotide within a 10mer palindrome. Hartmann G et al. *J Pharmacol Exp Ther* 285:920 (1998). ODN 1585 stimulated IFN-α in the nanogram range (1.3±0.4 ng/ml; n=7) as compared to ODN 2006 which did not induce significant amounts of IFN-α in PBMC (0.021±0.015 ng/ml; n=8) (FIG. 5). The control ODN 2197 (7-deaza-guanosine substitutions in poly G ends, unable to form G tetrads) and ODN 2198 (CG and poly G ends but no palindrome) were essentially inactive (FIG. 5). Based on the sequence of ODN 1585, a new panel of CpG ODN were then designed. ODN 2216 (ggGGGACGATCGTCgggggG; SEQ ID NO:7), which contains poly G ends and three CG dinucleotides within a palindrome, is one example among several sequences with pronounced IFN-α-inducing activity in PBMC (23.7±5.2 ng/ml; n=7).

Figure 6:
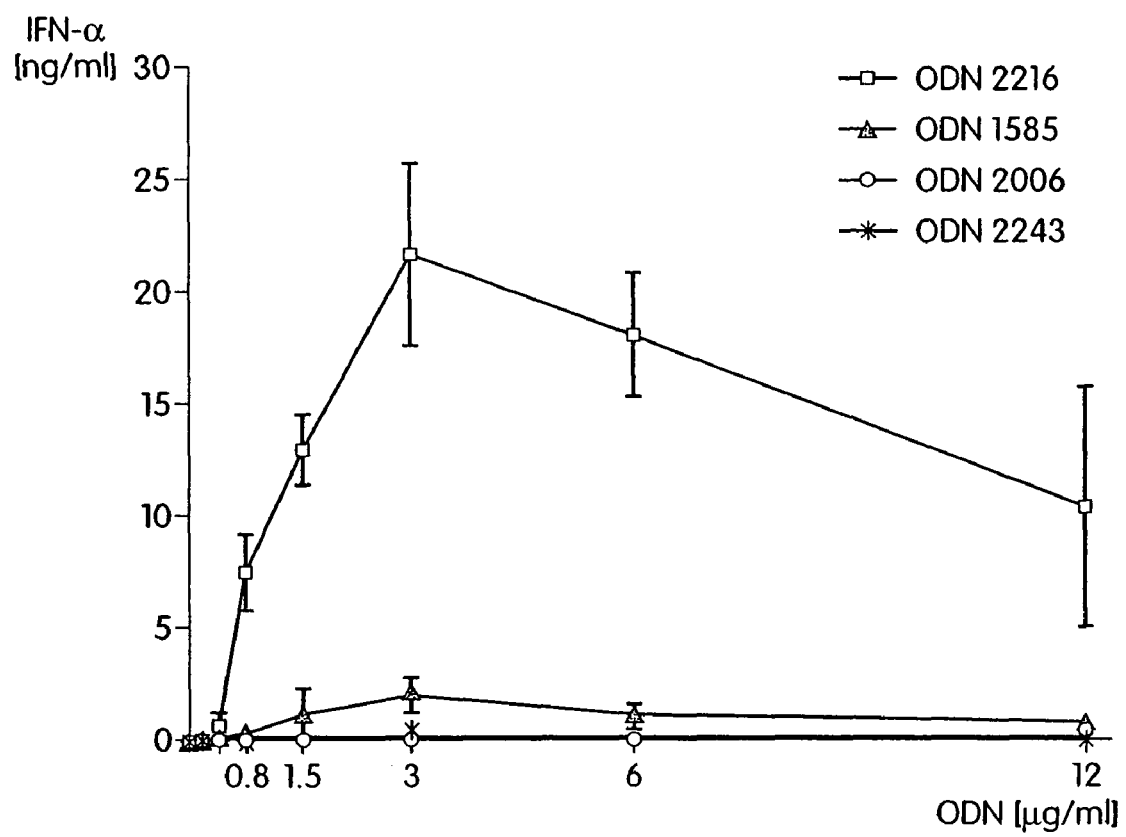
FIG. 6 is a graph depicting the dose-response of CpG ODN-induced IFN-α synthesis by PBMC cultured for 48 hours in the presence of ODN 2216, 1585, 2006, and 2243 at concentrations ranging from 0.2 to 12 μg/ml.

CpG ODN stimulated IFN-α production in a concentration-dependent manner (FIG. 6). The activities of ODN 2216 and ODN 1585 were tested for concentrations up to 12 µg/ml, confirming that the higher potency of ODN 2216 was not a concentration-dependent effect. As little as 0.4 µg/ml ODN 2216 induced considerable amounts of IFN-α (0.7 ng/ml) in PBMC, whereas ODN 2006 and the GC control to ODN 2216 (ggGGGAGCATGCTCgggggG; ODN 2243; SEQ ID NO:150) had no effect even at higher concentrations. Maximum activity was reached at 3 µg/ml. Production of IFN-α could already be detected after 6 hours of incubation (0.2 ng/ml) and reached a plateau after 48 hours.

Figure 7:
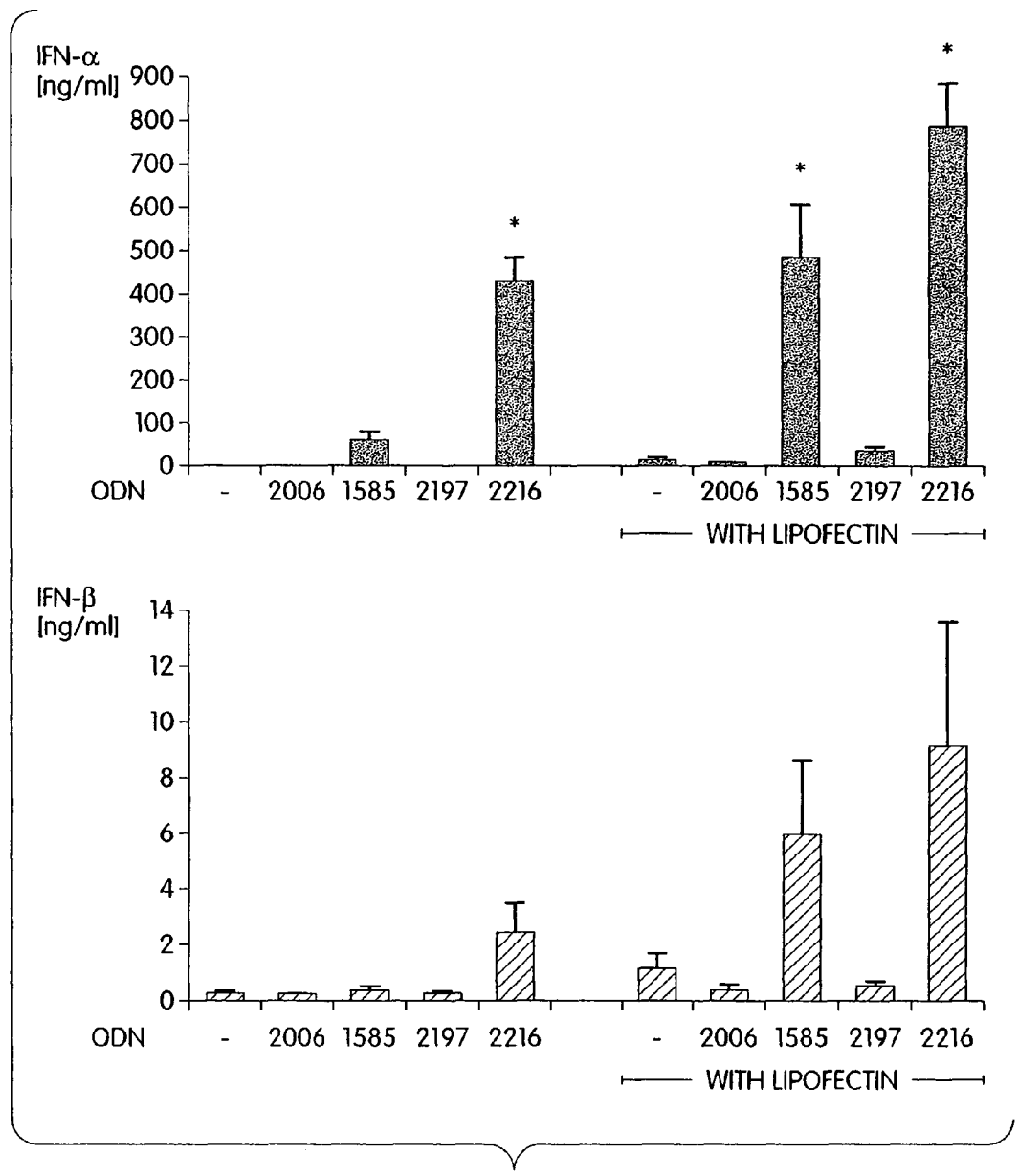
FIG. 7 is a graph depicting CpG ODN-mediated stimulation of IFN-α and IFN-β production in PBMC enriched for plasmacytoid dendritic cells, with (n=3) and without (n=4) addition of lipofectin (10 μg/ml). PBMC were cultured for 48 hours in the presence of IL-3 alone (–) or IL-3 with the addition of ODN 2006, 1585, 2197, or 2216. Results are presented as means of 3 or 4 independent experiments with different donors, each performed in duplicate. Error bars indicate SEM. *p<0.0018 (Bonferroni-Dunn correction).

The natural interferon-producing cell in PBMC upon virus infection is identical to the pDC precursor with a frequency of less than 0.5%. PBMC were enriched 10- to 70-fold for pDC precursors by depletion of T-cells, NK-cells and monocytes (2-18% CD123$^{++}$ pDC; 3-10% CD11c$^+$ myeloid DC (rnDC); 50-90% B-cells; n=4). To increase the viability of pDC, IL-3 was added to all samples. This procedure resulted in a 30- to 60-fold increase in IFN-α production (up to 428.3±56.8 ng/ml with ODN 2216; n=4; FIG. 7, upper panel, left side). The most active CpG ODN in PBMC were also the most active in the samples enriched for pDC. ODN 2006, ODN 2197, or IL-3 alone induced only little IFN-α (means: 0.8, 0.4 and 0.6 ng/ml respectively, n=4). Poly (I:C) (7 µg/ml), which mimics double-stranded RNA and which is known to induce IFN-α in macrophages, was an even weaker stimulus of IFN-α in cells enriched for pDC (0.3 ng/ml, not in figure). The same CpG ODN which induced high amounts of IFN-α also stimulated IFN-β production (up to 2.8±0.8 ng/ml, n=4; FIG. 7, lower panel, left side). Considering that IFN-β represents a single isoform and that IFN-α consists of at least 13 isoforms, remarkable amounts of IFN-β are produced.

To determine whether cellular uptake of CpG ODN was critical for the induction of IFN-α and IFN-β by CpG ODN, the effects of the cationic lipid lipofectin were examined (FIG. 7, upper and lower panel, right side). Positively charged cationic lipids form complexes with negatively charged ODN, which increase cellular uptake of ODN. Lipofectin enhanced the production of IFN-α and IFN-β induced by CpG ODN (up to 786 ng/ml IFN-α, n=3; and up to 9 ng/ml IFN-β, n=3). The increase was seen for all CpG ODN examined but was most prominent for ODN 1585 (20-fold).

Example 6

CpG ODN-Induced IFN-α is Exclusively Produced by Plasmacytoid Dendritic Precursor Cells To examine which cell type within PBMC produces IFN-α in response to CpG ODN, a protocol was developed which allowed the detection of intracellular IFN-α on a single cell basis by flow cytometry. PBMC were incubated with ODN 2216 (SEQ ID NO:7) or ODN 2006 (SEQ ID NO:147) at 3 µg/ml. After five hours, cells were harvested and intracellular staining of IFN-α was performed. For the analysis of intracellular IFN-α, no brefeldin A was added during the incubation period to block protein secretion. PBMC were harvested (approximately 600,000 cells/tube), incubated with anti-CD123-biotin (Pharmingen), washed in PBS (400 g, 5 minutes, 4° C.) and stained with Streptavidin-APC (Pharmingen), FITC-conjugated anti-lineage cocktail (consisting of anti-CD3, -CD14, -CD16, -CD19, -CD20, and -CD56; Becton Dickinson), and anti-HLA DR-PerCP (Becton Dickinson). Then cells were washed in PBS, resuspended in 100 µl of fixation buffer A (Fix and Perm Kit, Caltag Laboratories, Burlingame, Calif.)

and incubated at room temperature for 15 min. Cells were washed in 2 ml PBS again and then resuspended in 100 µl permeabilization buffer B (Fix and Perm Kit). 4 µg/ml mouse anti-human IFN-α mAb (MMHA-11, PBL Biomedical Laboratories) was added. PE-labeled mouse IgG1 (MOPC-21, Pharmingen) was used as control antibody. After 15 min incubation at room temperature in the dark, cells were washed in 2 ml PBS. For detection of intracellular IFN-α cells were again resuspended in 100 µl permeabilization buffer B (Fix and Perm Kit) and stained with PE-labeled rat anti-mouse Ig κ light chain (R8-140, Pharmingen) as secondary antibody. After washing in PBS, cells were analyzed by four-color flow cytometry on a Becton Dickinson FACS Calibur equipped with two lasers (excitation at 488 nm and 635 nm). Spectral overlap was corrected by appropriate compensation and gates were set using isotype control antibodies. Analysis was performed on viable cells within a morphologic gate (FSC, SSC, >97% of viable cells as confirmed by propidium iodide staining). Data were analysed using CELLQUEST (Becton Dickinson) or FLOWJO software (version 2.5.1, Tree Star, Inc., Stanford, Calif.).

Figure 8A:
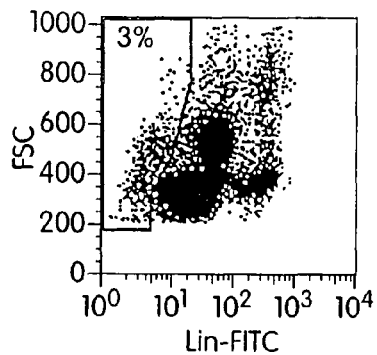
FIG. 8 is a series of four graphs depicting results of four FACS experiments examining intracellular IFN-α. Panel A, identification of lin+ and lin− cells. Panel B, identification of CD123+/−/HLA DR++ mDC (gate II) and CD123++/HLA DR+ pDC (gate III) in lin− cells. Panel C, lack of staining for intracellular IFN-α in lin+ cells. Panel D, staining for intracellular IFN-α in lin− cells.

Results. As shown in FIG. 8A, lineage$^+$ and lineage$^-$ (lin$^+$ and lin$^-$) cells were defined by lineage marker expression and forward scatter characteristics. After stimulation with ODN 2216 intracellular IFN-α was not detectable in lin$^+$ cells which contain monocytes and macrophages as potential IFN-α producing cells (FIG. 8C). Within the lin$^-$ cells, which contain mainly pDC and mDC, a distinct population with intermediate HLA DR (MHC class II) expression stained positive for IFN-α (FIG. 8D).

Figure 8B:
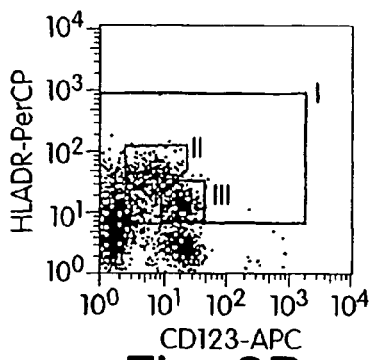
Figure 8C:
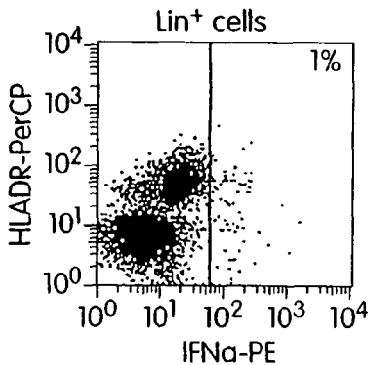
Figure 8D:
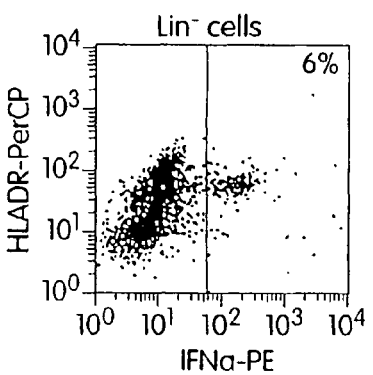
Figures 9A, 9B:
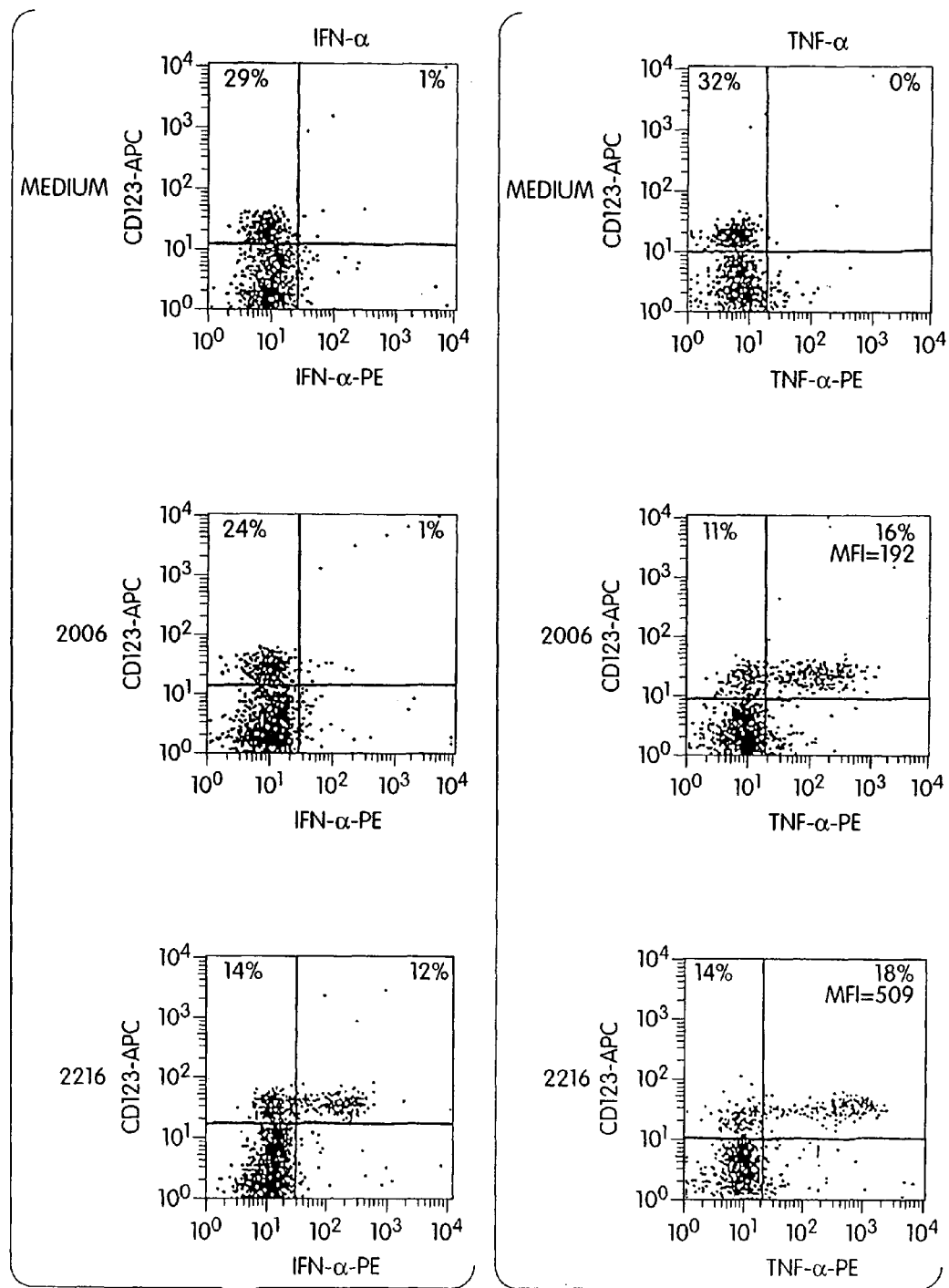
FIG. 9 is a series of six graphs depicting results of six FACS experiments examining intracellular IFN-α (Panels A) and TNF-α (Panels B) in lin−/HLA DR+ plasmacytoid dendritic cell precursor cells after stimulation with different CpG oligonucleotides (2006, 2216, both at 3 μg/ml). Brefeldin A was added during incubation for TNF-α. MFI, mean fluorescence intensity.

Within the lin$^-$ population, mDC and pDC can be distinguished by their HLA DR/CD123 phenotype (FIG. 8B). The mDC are CD123$^\pm$ and HLA DR$^{++}$ (gate II); pDC are CD123$^{++}$ and HLA DR$^+$ (gate III). The CD123$^{++}$/HLA DR$^-$ population are basophils. FIG. 9A shows intracellular staining for IFN-α in lin$^-$/HLA DR$^+$ cells. IFN-α was exclusively produced by pDC in response to ODN 2216 but not in response to ODN 2006. Among pDC 46% stained positive for IFN-α, corresponding to a frequency of 0.25% cells within PBMC which produced IFN-α at this particular time point of staining. In three other experiments frequencies of IFN-α producing cells in response to ODN 2216 were 0.08%, 0.05% and 0.22% of PBMC (16%, 8% and 63% of pDC).

In contrast to the results with pDC, in mDC no IFN-α synthesis was detected after stimulation with ODN 2006 or ODN 2216.

Thus, pDC were the only cells within PBMC which produced IFN-α in response to CpG ODN. Of note, intracellular IFN-α staining was performed without brefeldin A. Thus the amount of IFN-α detected represented the actual IFN-α production at the time point of harvest and not the cumulative amount of IFN-α over several hours. When brefeldin A was added during incubation to block protein secretion (standard protocol for intracellular cytokine staining), no IFN-α-producing cells could be detected.

Example 7

Both IFN-α-Inducing and Non-IFN-α-Inducing CpG ODN Stimulate Early TNF Production in Plasmacytoid Dendritic Cells It has been reported that pDC produce TNF-α in response to IL-3 and thus promote their own maturation in an autocrine fashion. Hartmann G et al. *Antisense Nucleic Acid Drug Dev* 6:291-9 (1996). The intracellular accumulation of TNF-α in pDC therefore was examined in response to different CpG ODN (FIG. 9B). PBMC were incubated for five hours with ODN 2216 (SEQ ID NO:7) or ODN 2006 (SEQ ID NO:147) at 3 µg/ml in the absence of IL-3. Brefeldin A (1 µg/ml, Sigma) was added during the five hour stimulation period to block cytokine secretion. PBMC were harvested (approximately 600,000 cells/tube), incubated with anti-CD123-biotin, washed in PBS (400 g, 5 minutes, 4° C.) and stained with Streptavidin-APC (Pharmingen), FITC-conjugated anti-lineage cocktail and anti-HLA DR-PerCP (Becton Dickinson). Then cells were washed in PBS, resuspended in 100 µl of fixation buffer A (Fix and Perm Kit, Caltag Laboratories, Burlingame, Calif.) and incubated at room temperature for 15 min. Cells were washed in 2 ml PBS again and then resuspended in 100 µl permeabilization buffer B (Fix and Perm Kit). 5 µg/ml PE-labeled mouse anti-human TNF-α mAb (MAb11, Pharmingen) was added as primary antibody. PE-labeled mouse IgG1 (MOPC-21, Pharmingen) was used as control antibody. After 15 min incubation at room temperature in the dark, cells were washed in 2 ml PBS and then analyzed by four-color flow cytometry as described above.

Results. In contrast to IFN-α, the percentage of TNF-α producing pDC in response to ODN 2006 and ODN 2216 was similar (59% versus 56%). Two other experiments showed comparable results (26 vs 22% and 8 vs 6% TNF-α$^+$ pDC with ODN 2006 and ODN 2216, respectively). The production of TNF-α per cell (MFI, mean fluorescence intensity) was consistently higher with ODN 2216 than with ODN 2006 (FIG. 9B). No TNF-α was detected in mDC. Lineage$^+$ cells did not produce significant amounts of TNF-α in response to either ODN 2006 or ODN 2216.

Example 8

Figure 10:
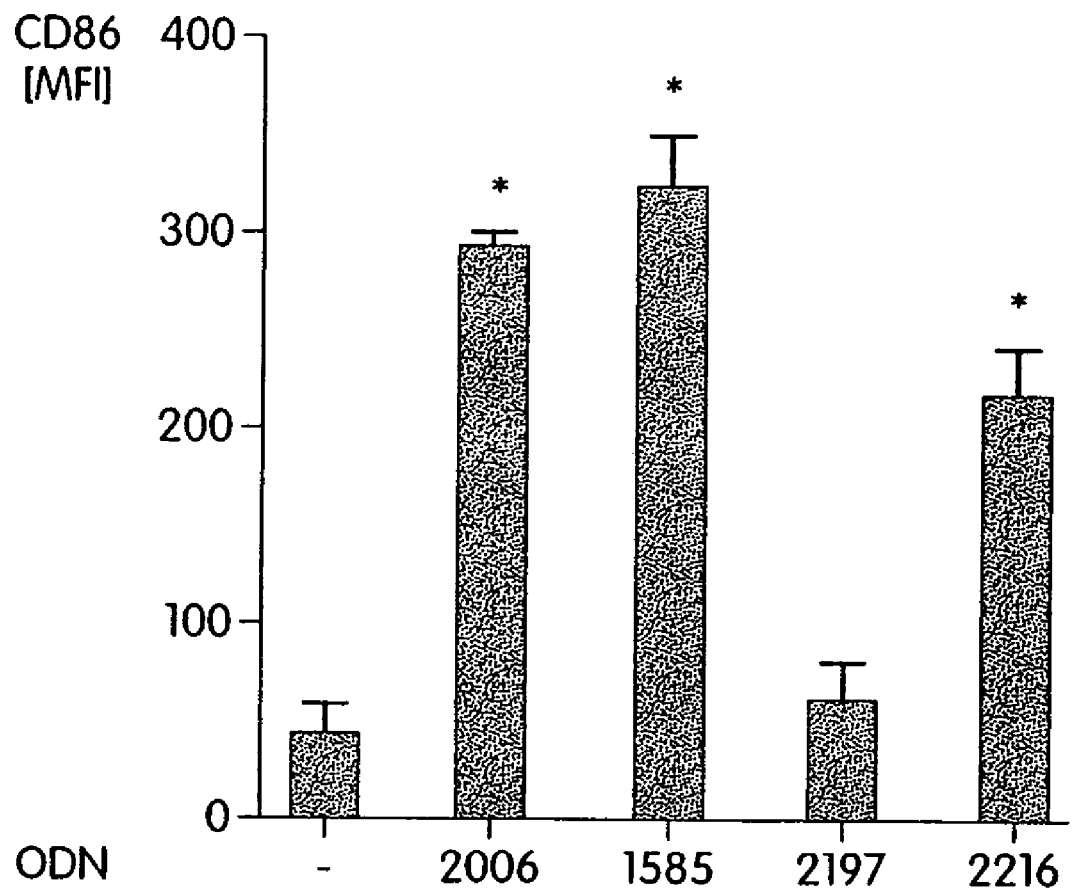
FIG. 10 is a graph depicting CD86 expression on plasmacytoid dendritic cells in response to IL-3 alone (–) or to IL-3 with various CpG ODN (2006, 1585, 2197, or 2216, each at 3 μg/ml). Results are presented as means of three independent experiments with cells from different donors. Error bars indicate SEM. *p<0.0018 (Bonferroni-Dunn correction).

Upregulation of Costimulatory Molecules on pDC in Response to IFN-α-Inducing CpG ODN In previous studies ODN 2006 was reported to stimulate the expression of costimulatory molecules on CD4$^+$ peripheral blood DC. Zhong R K et al. *J Immunol* 163:1354 (1999). In order to examine the capacity of different CpG ODN to upregulate CD80 and CD86 on pDC, PBMC were depleted of monocytes, T cells and NK cells, and the remaining cells were stimulated with different CpG ODN in the presence of IL-3. After 48 hours, expression of CD80 and CD86 was examined on pDC (CD123$^{++}$/HLA DR$^+$) by three-color flow cytometry. B-cells (CD123$^-$/HLA DR$^+$) and mDC (CD123$^\pm$/HLA DR$^{++}$) were excluded from the analysis. As shown in FIG. 10, expression of CD86 on pDC was increased by ODN 2006 (SEQ ID NO:147) as well as by ODN 1585 (SEQ ID NO:1) and ODN 2216 (SEQ ID NO:7). The effect of ODN 1585 was abolished by substitution of the poly G tails with 7-deazaguanosine (ODN 2197; SEQ ID NO:148). The non-palindrome CpG ODN 2198 (SEQ ID NO:149) was inactive. Upregulation of CD80 and HLA DR was similar to CD86. Increased expression of CD80 and CD86 in response to the weakly IFN-α-inducing ODN 2006 was detectable after 6 hours. In contrast, ODN 1585 and ODN 2216 showed a delayed response, starting later than 12 hours. For both strongly IFN-α-inducing CpG ODN (ODN 1585, ODN 2216) and weakly IFN-α-inducing CpG ODN (ODN 2006), a plateau was reached after 48 hours. At later time points, identification of pDC among PBMC by flow cytometry was hampered by downregulation of CD123 during cell culture.

Example 9

Figure 11A:
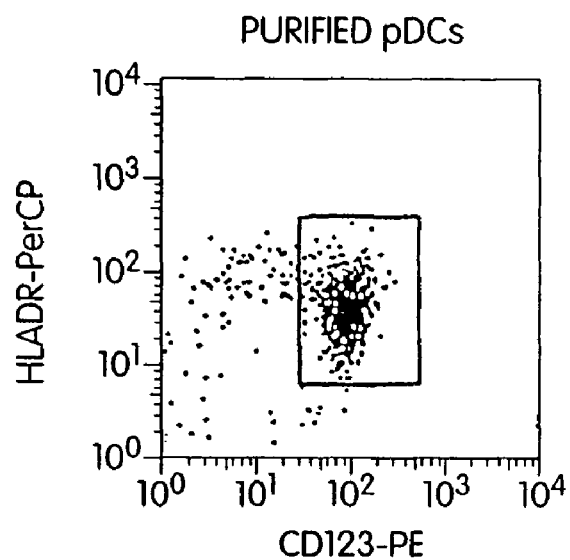
FIG. 11 depicts a graph representing a FACS purification of plasmacytoid dendritic cells (Panel A) and the secretion of IFN-α and IFN-β by purified plasmacytoid dendritic cells in response to IL-3 with and without ODN 2216 (Panel B).
Figure 11B:
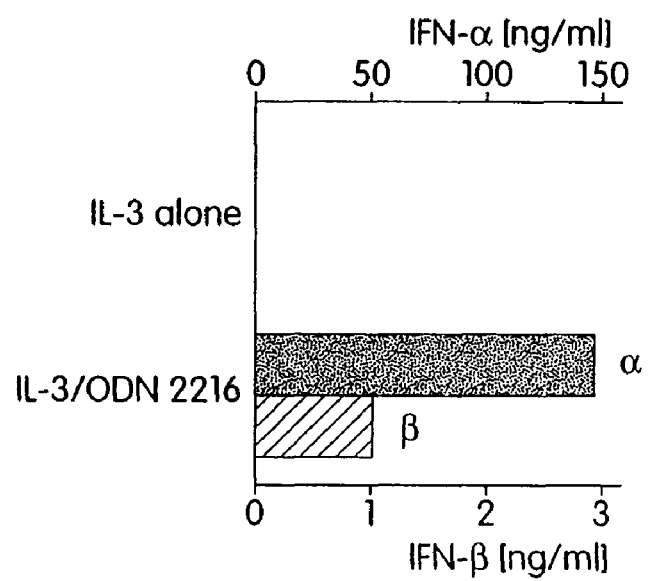

Stimulation of IFN-α and IFN-β Production by CpG ODN is a Direct Effect on Plasmacytoid Dendritic Cells and is Partially Blocked by Anti-CD4 Magnetic Beads In order to examine whether CpG ODN induce IFN-α production directly, purified pDC, rather than pDC-enriched PBMC were studied. PBMC were depleted of monocytes, T-cells, NK cells and B cells. CD123++ and HLA DR+ pDC were sorted by FACS from the remaining cell population to yield purified (97%) pDC (FIG. 11A). Purified pDC (160,000 cells/ml) were incubated with or without ODN 2216 (SEQ ID NO:7) in the presence of IL-3. After 48 hours IFN-α and IFN-β were measured in the supernatant by ELISA. As shown in FIG. 11B, ODN 2216 stimulated the production of high levels of IFN-α (146 ng/ml; 1 pg per single pDC) and IFN-β (1 ng/ml), as compared to IL-3 alone (<10 pg/ml).

Within PBMC as well as within pDC-enriched PBMC, 4.2±0.8 pg IFN-α (0.8 to 1.4 U; n=4) was produced per single pDC. IFN-α production of pDC was much lower when pDC were enriched by using magnetically labeled anti-CD4 mAb. This was not due to a loss of IFN-α producing cells in the CD4- fraction, since the CD4- fraction did not produce IFN-α. Adding the CD4- fraction back to CD4+ DC did not restore the IFN-α response, thereby excluding a secondary effect of CpG ODN via accessory cells in the CD4- fraction. Thus, crosslinking of CD4 on the surface of pDC appeared to be responsible for the reduced activity.

Example 10

IFN-α-Inducing CpG ODN Provide Superior Indirect Activation of NK Cells Compared to Non-IFN-α-Inducing CpG ODN To examine if CpG ODN which induce high amounts of IFN-α also show higher activation of NK cells, PBMC were incubated with different CpG ODN. NK cell activation was measured in terms of CD69 expression (FACS) and by in vitro NK-cell lytic activity. For determination of NK-cell lytic activity, PBMC were incubated with different ODN at various concentrations. After 18 hours cells were harvested and used as effector cells in a standard 4 hour $^{51}$Cr-release assay against K562 target cells as previously described. Hartmann G et al. *Gene Therapy* 6:893 (1999). Positive controls included recombinant IL-2 (100 IU/ml) and negative controls included media alone. Results are expressed as % specific lysis: specific lysis (%)=((experimental counts−spontaneous release counts)/(maximal release counts−spontaneous release counts))×100%.

Figure 12:
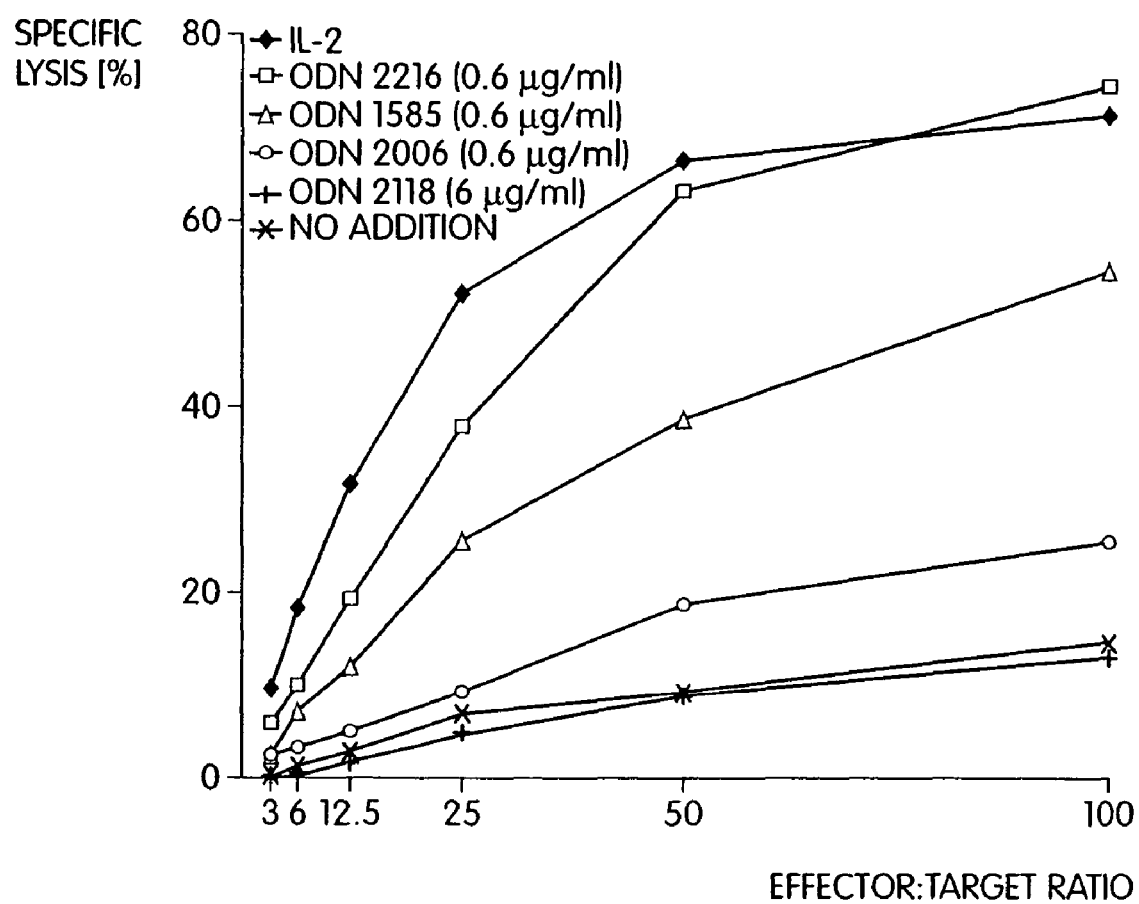
FIG. 12 depicts NK cell-mediated lysis of K562 cells following exposure of PBMC to ODN 2216, 1585, 2006, 2118, IL-2, or media alone.

Results. The IFN-α-inducing ODN 2216 and ODN 1585 increased the percentage of CD69-positive (early marker of activation) NK cells within 24 hours (38±12% with ODN 2216; n=5) as compared to the control without stimulus (8±2%; n=5). ODN 2006 showed a lower response (19%±6%). In agreement with increased CD69 expression, NK cell-mediated lysis of K562 cells was markedly enhanced when PBMC were incubated with CpG ODN. Even at the low concentration of 0.6 μg/ml, ODN 2216 (SEQ ID NO:7) was still as effective as IL-2 (100 IU/ml) to stimulate NK cell lytic activity (FIG. 12). ODN 1585 (SEQ ID NO:1) and ODN 2006 (SEQ ID NO:147) were less effective. Even at higher concentrations (6 μg/ml) the GC control to ODN 1585 (5' ggGGTCAAGCTTGAgggggG 3'; ODN 2118; SEQ ID NO:151) was completely inactive compared to medium alone (FIG. 12). When purified NK cells were incubated with CpG ODN, CD69 expression and lysis of K562 cells was not increased, demonstrating an indirect effect of CpG ODN on NK cells.

Example 11

CpG Oligonucleotide Induces Production of High Amounts of IL-8 by IPCs

IL-8 is a chemokine which attracts other immune cells. IPCs grown in IL-3 produce no IL-8, while CpG oligonucleotide stimulates the production by IPCs of large amounts of IL-8 (mean 23 ng/ml, FIG. 13).

Freshly prepared IPCs (see Example 1, final concentration $2\times10^5$-$5\times10^5$ cells per ml) were cultured for two days in complete medium supplemented with 10 ng/ml IL-3. One set of parallel cultures was supplemented with 10 μg/ml poly IC, and another set of parallel cultures supplemented with 6 μg/ml CpG ODN 2006 (SEQ ID NO:147). Supernatants were analyzed for IL-8 using an ELISA specific for human IL-8 (R&D Systems, Minneapolis, Minn.) according to the supplier's instructions.

Figure 13:
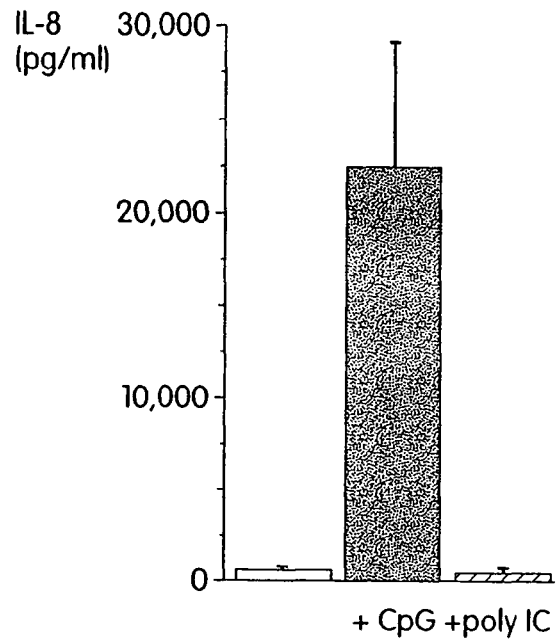
FIG. 13 is a graph depicting the concentration of IL-8 (determined by an IL-8-specific ELISA) present in the supernatant of IPCs cultured for two days in the presence of IL-3 alone (left), IL-3 supplemented with CpG oligonucleotide (middle), or IL-3 supplemented with poly IC (right). Results are representative of three independent experiments.

Results. Representative data from three different donors are shown in FIG. 13. IL-8 secretion by IPCs was strongly induced by the addition of CpG oligonucleotide to complete media containing IL-3. In contrast, addition of poly IC to the media had no effect. This result demonstrates that CpG oligonucleotide induces IPCs to produce high amounts of IL-8.

Example 12

Type I IFN Induces Activation and Proliferation of γδ T Cells

The γδ T cells (Vγ9/Vδ2) are antigen-specific T cells in a preactivated stage which respond to common non-peptidic phosphoantigens. Exposure of γδ T cells to these antigens stimulates IFN-γ production in the absence of APC. To examine γδ T cell activation, PBMC ($2\times10^6$/ml) from healthy donors were stimulated for three days with 6 μg/ml CpG ODN (2006, 1585, or 2216) or medium alone in the presence or absence of 15 μM isopentenyl pyrophosphate (IPP, specific phosphoantigen for Vγ9/Vδ2 cells). Brefeldin A was added for the last 4 hours. After surface staining for Vγ9 TCR and CD3, cells were fixed, permeabilized and stained with mAb against IFN-γ. In three-color flow cytometry γδ T cells were gated using their FSC/SSC profile, CD3 and TCR Vγ9 expression and analyzed for IFN-γ expression. To compare the results from different donors, data were calculated first as x-fold increase compared to medium or IPP controls and then multiplied with the mean of medium and IPP, respectively. Between 14 and 20 donors were analyzed for each CpG ODN. Data are presented as mean+SEM; * (p<0,01) and ** (p<0,001) indicate p values calculated by Student's t-test for paired samples comparing medium control to CpG ODN and IPP alone to IPP+CpG ODN.

To examine γδ T cell proliferation, PBMC from healthy donors were stimulated with IPP (30 μM) in the presence or absence of different CpG ODN (2006, 1585, or 2216, each at 6 μg/ml). The expansion of γδ TCR positive cells was assessed by flow cytometry with an anti Vγ9 antibody and is shown as % TCR Vγ9 positive cells within viable PBMC.

Between 9 and 16 donors were analyzed for each ODN. Data are presented as x-fold increase compared to IPP alone (mean+SEM); * indicates p<0,05 (IPP versus IPP+CpG ODN.

Figure 14:
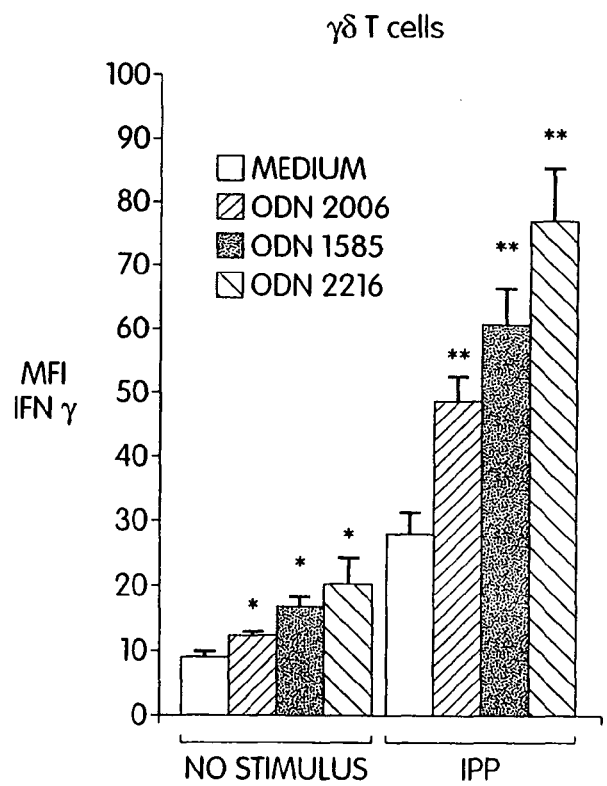
FIG. 14 is a graph depicting IFN-γ production by γδ T cells in response to CpG ODN 2006, 1585, or 2216 in the presence or absence of nonpeptide antigen isopentenyl pyrophosphate (IPP). Results are shown in terms of mean fluorescence intensity (MFI) for intracellular staining for IFN-γ, with medium alone as negative control. Data are presented as mean+ SEM; * (p<0,01) and ** (p<0,001) indicate p values calculated by Student's t-test for paired samples comparing medium control to CpG ODN and IPP alone to IPP+CpG ODN.

Results. Within PBMCs both γδ T cells and NK cells but not αβ T cells responded to CpG ODN with increased CD69 expression, IFN-γ and TNF-α production, perforin content and lytic activity. CpG ODN in combination with IPP synergistically induced the production of IFN-γ (FIG. 14) and perforin in γδ T cells. The synergistic effect was more pronounced for ODN 2216 and 1585, i.e., ODN that are strong inducers of type I IFN, than for ODN 2006. In purified γδ T cells or NK cells, CpG ODN showed no activity or even reduced IPP-stimulated activity.

Figure 15A:
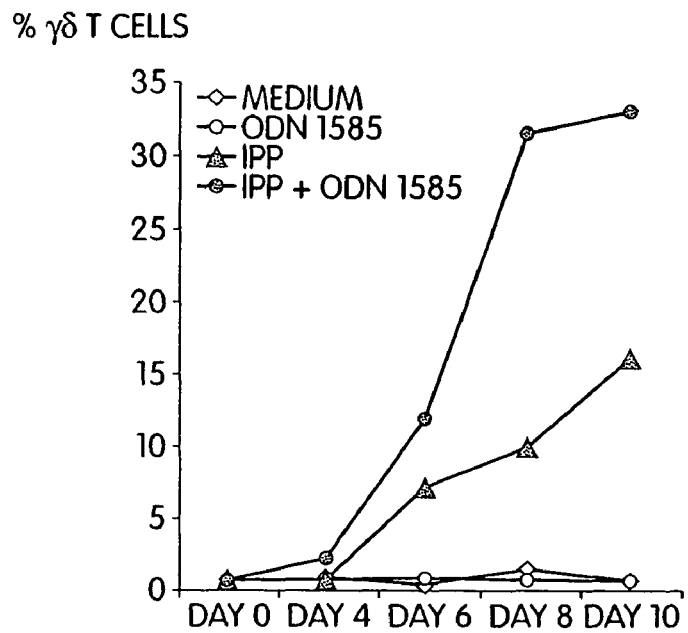
FIG. 15 is a pair of graphs depicting proliferation of γδ T cells in response to CpG ODN 2006, 1585, or 2216 in the presence or absence of nonpeptide antigen isopentenyl pyrophosphate (IPP). Panel A depicts the kinetics of γδ T cell expansion, over 10 days, from one representative experiment. Panel B depicts the expansion of γδ T cells 10 days after stimulation with IPP alone or in combination with different CpG ODN. Between 9 and 16 donors were analyzed for each ODN. Data are presented as x-fold increase compared to IPP alone (mean+SEM); * indicates p<0,05 (IPP versus IPP+CpG ODN.
Figure 15B:
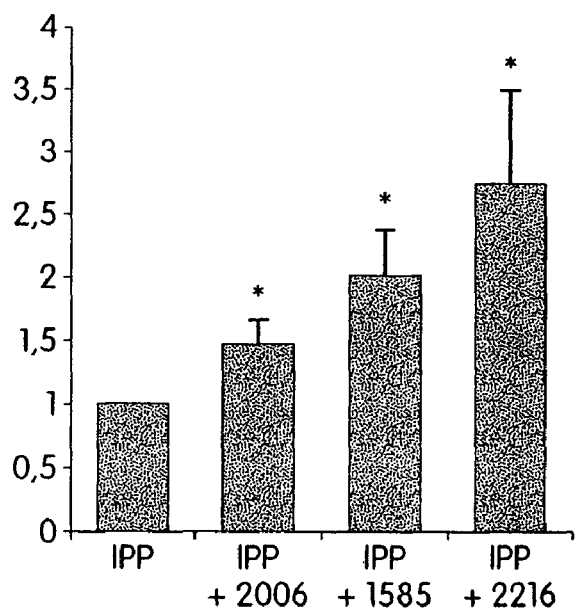

Furthermore CpG ODN synergistically enhanced the proliferative response of γδ T cells to IPP (FIG. 15). FIG. 15A shows the kinetics of γδ T cell expansion from one representative experiment. FIG. 15B shows the expansion of γδ T cells 10 days after stimulation with IPP alone or in combination with different CpG ODN.

The addition of recombinant IFN-α/β or IL-12 mimicked the stimulatory effects of CpG ODN within PBMC. Functional IL12p70 could not be detected in the supernatants of PBMCs stimulated with CpG ODN. The potential of CpG ODN to activate γδ T-cells and NK cells correlated well with their ability to induce IFN-α/β. The blockade of IFN-α/β function by a combination of neutralizing antibody to IFN-α/β protein and the corresponding receptor inhibited CpG ODN-induced activation of γδ T cells and NK cells. A neutralizing antibody to IL-12 or the addition of IL-18 binding protein reduced baseline IFN-γ but not CpG ODN-stimulated IFN-γ. Neutralizing TNF-α, IL-1β or IL-15 showed no effect. In conclusion the results demonstrated that (i) IFN-α/β is a potent activator of γδ T cells; (ii) CpG ODN activates γδ T cells and NK cells via induction of IFN-α/β; (iii) CpG ODN which are strong inducers of type I IFN are more potent than ODN which are not strong inducers of type I IFN to activate γδ T cells and NK cells; (iv) CpG ODN costimulate antigen-specific T cell responses in γδ T cells; and (v) CpG ODN-induced nonspecific activation of γδ T cells and NK cells provides early IFN-γ which promotes Th1 responses.

Example 13

Type I IFN-Inducing ISNA Inhibit IL-12 Production

IFN-β has been described to downregulate IL-12 production. The effect of type I IFN-inducing and non-type I IFN-inducing ISNA on IL-12 production was therefore studied as follows. PBMC ($2\times10^6$/ml) from healthy donors were stimulated with 25 µg/ml of a stimulating anti-CD40 antibody in the presence of IL-4 (100 U/ml), GM-CSF (10 U/ml) and IFN-γ (10 ng/ml). Either medium, 6 µg/ml ODN 2006 (SEQ ID NO:147), 6 µg/ml ODN 1585 (SEQ ID NO:1), or a combination of 5000 U/ml recombinant IFN-α and 500 U/ml IFN-β were added. After 48 hours IL12p70 was measured in the supernatant by ELISA. Data are shown as x-fold of IL12p70 production by anti-CD40 alone (mean=143 pg/ml) and represent the mean (+SEM) of three different donors.

Figure 16:
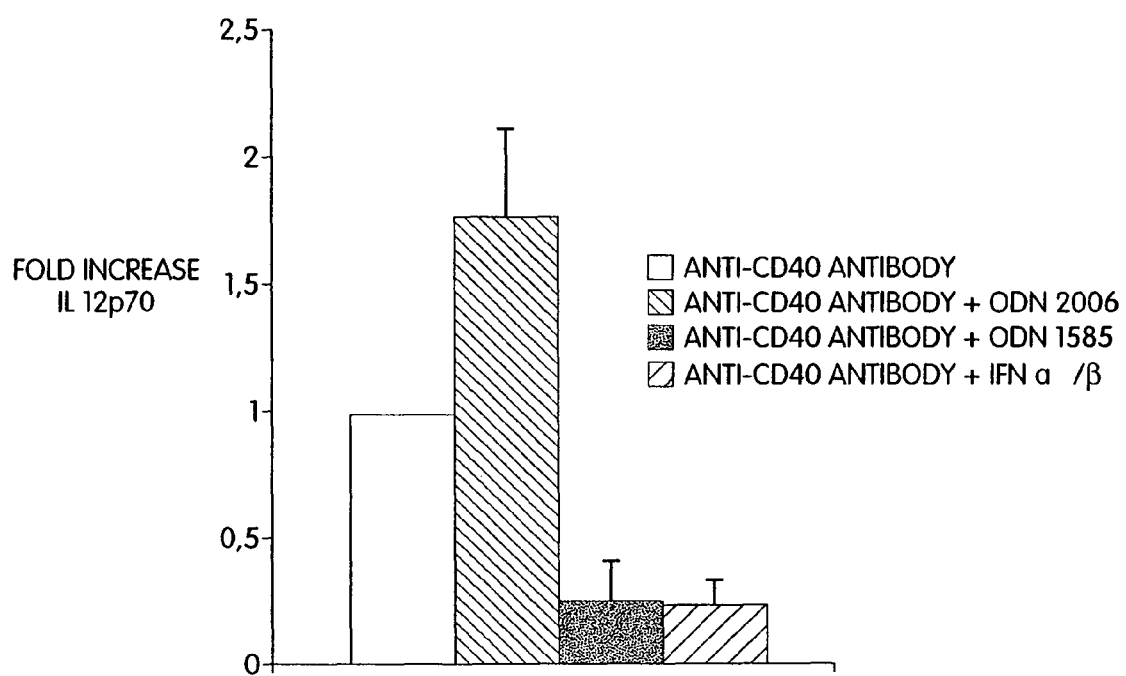
FIG. 16 is a graph depicting regulation of CD40-induced IL-12p70 production by type I IFN and by various CpG ODN. Data are shown as x-fold of IL-12p70 production by anti-CD40 alone (mean=143 pg/ml) and represent the mean+SEM of three different donors.

Results. FIG. 16 shows that ODN 1585 in combination with anti-CD40 inhibited IL12p70 production compared to anti-CD40 control, to an extent similar to the inhibition by addition of recombinant IFN-α and recombinant IFN-β. In contrast, ODN 2006 in combination with anti-CD40 boosted IL12p70 production beyond anti-CD40 positive control. These results show that, in PBMC, ISNA that induce type I IFN can suppress production of IL-12p70, and conversely ISNA that do not induce type I IFN can boost production of IL-12p70.

Analysis of mRNA levels by quantitative real-time PCR revealed the induction of small but equal copy numbers of IL-12p40 and IL-12p35 mRNA by ISNA that do not induce type I IFN. In contrast, ISNA that induce type I IFN induced a higher number of copies of IL-12 p35 mRNA, but IL-12p40 mRNA could not be detected. ISNA that do not induce type I IFN enhanced (170%), and ISNA that induce type I IFN blocked (25%) IL-12p70 synthesis. Inhibition of IL-12p70 could be mimicked by recombinant IFN-β. A combination of neutralizing antibodies to IFN-α/β protein and receptor reversed the type I IFN-inducing ISNA-mediated inhibition of IL-12p70. These results demonstrate that CpG ODN which are strong inducers of type I IFN suppress CD40-dependent IL-12p70 production by an IFN-α/β-mediated negative feedback mechanism on IL-12p40 mRNA production. Thus the interaction of T cells and antigen presenting cells via CD40L leads to a cytokine milieu dominated by IL-12 (ISNA that do not induce type I IFN) or IFN-α/β (ISNA that induce type I IFN). Although both promote Th1 responses, ISNA that do not induce type I IFN may be superior for priming naive T cells, and ISNA that induce type I IFN may have higher activity to support preactivated and memory T cells.

Example 14

Effect of CpG ODN on Primary and Recall Peptide-Specific Human CTL Responses

CD8+ T cells ($1\times10^6$) from HLA A2 positive healthy donors were stimulated in 24 well plates in the presence or absence of CpG ODN 2006 (SEQ ID NO:147), 1585 (SEQ ID NO:1), or 2216 (SEQ ID NO:7) at 6 µg/ml with either a HLA A2-restricted peptide derived from the influenza matrix protein (GILGFVFTL; SEQ ID NO:166) or a peptide derived from the melan A/mart-1 protein (ELAGIGILTV; SEQ ID NO:167). Autologous PBMC ($3\times10^6$) were used as APCs. After 14 days cells were harvested, washed, and restimulated with influenza matrix or melan-A peptides for 6 hours. Brefeldin A was added for the last 4 hours. Cells were stained for CD8 and CD3, subsequently fixed, permeabilized and stained with mAb against IFN-γ. Also after 14 days the percentage of tetramer-positive CD8+ T cells (HLA-A2/melan-A-peptide and HLA-A2/influenza matrix-peptide) was determined by flow cytometry. Tetramers are fluorochrome-labeled MHC-peptide tetramers which are designed to bind specifically to a peptide-specific T cell receptor, making it possible to identify peptide-specific T cells using flow cytometry. Altman J D et al. Science 274:94-96 (1996); U.S. Pat. No. 5,635,363.

Figure 17A:
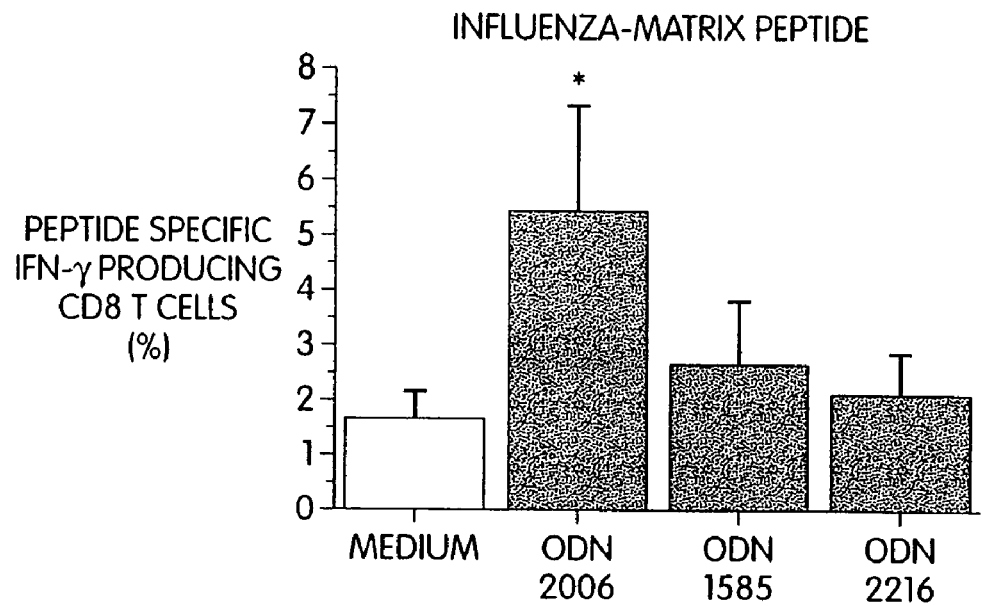
FIG. 17 is a series of graphs depicting the effects of CpG ODN 2006, 1585, and 2216 on recall and primary peptide-specific human CTL responses. Panels A and C, peptide-specific IFN-γ producing CTL as a percentage of all CD8+ T cells for the recall antigen influenza-matrix peptide and for the primary antigen melan-A/mart-1 peptide, respectively. Panels B and D, antigen-specific tetramer-positive staining CD8+ T cells for the recall antigen influenza-matrix peptide and for the primary antigen melan-A/mart-1 peptide, respectively.

Results. In three-color flow cytometry CD8+ T cells (CTL) were analyzed for IFN-γ expression. Results are presented in FIG. 17A and 17C as % IFN-γ positive cells of all CD8+ T cells. Peptide specificity was tested by stimulating with an irrelevant HLA A2 peptide derived from HIV pol and was <0.2% for all samples. Data from 7 donors are presented as mean+SEM. These results show that ODN 2006 increased both primary and recall CTL responses to melan A/mart-1 peptide and to influenza peptide, respectively, in contrast to ODN 1585 and ODN 2216, which induced less recall and had no effect or even inhibited the development of primary CTLs.

Figure 17B:
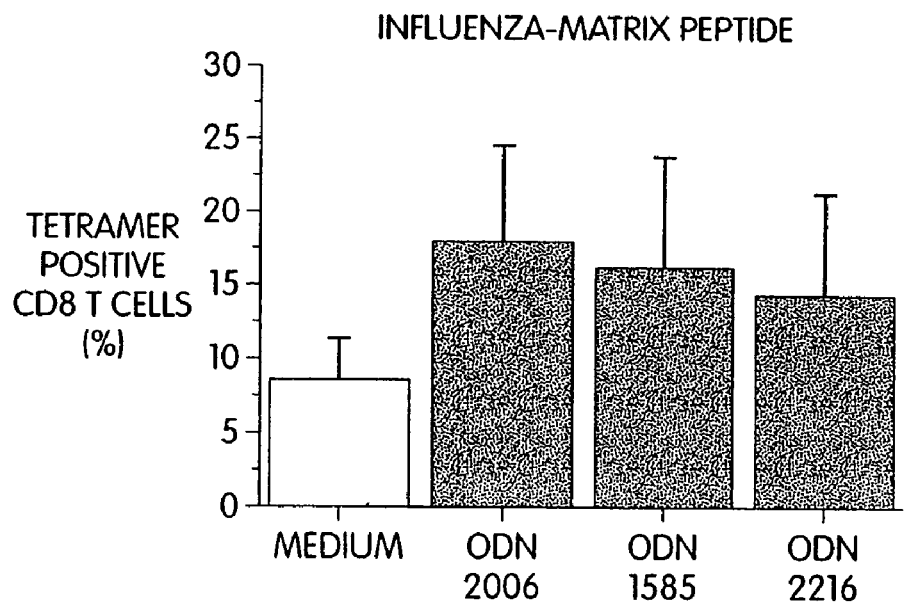
Figure 17C:
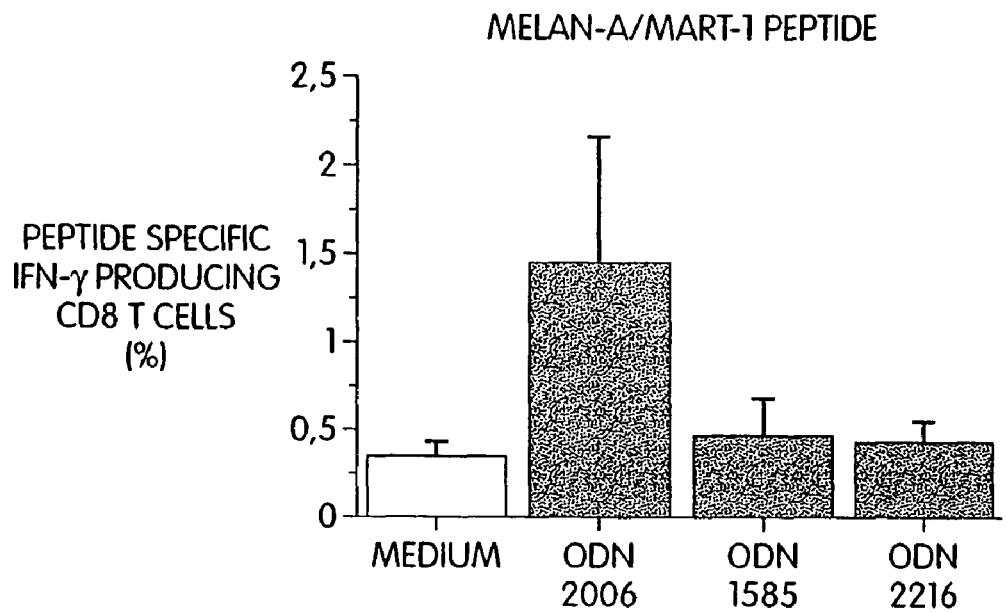
Figure 17D:
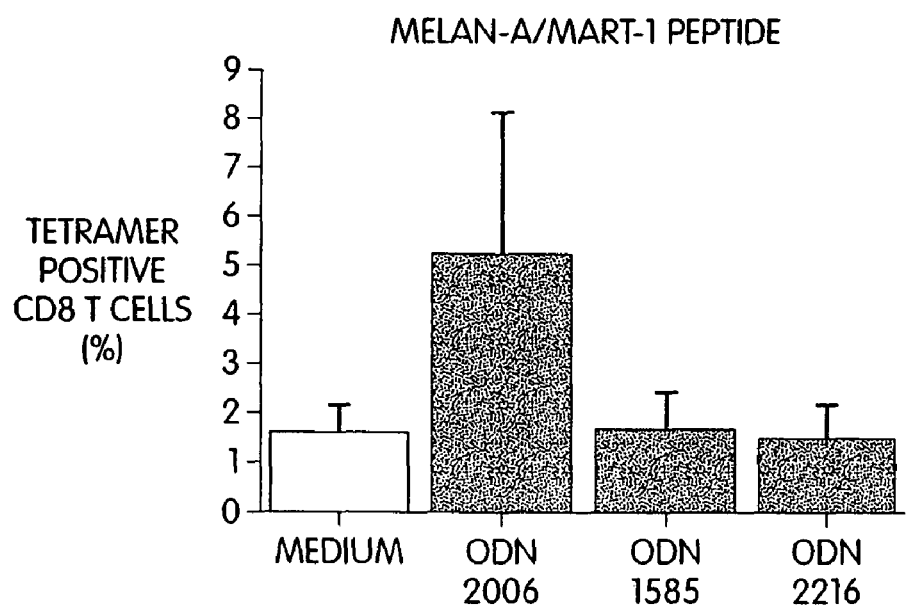

Results from the quantification of antigen-specific CTLs using MHC-tetramer staining are shown for influenza peptide and melan A/mart-1 peptide in FIG. 17B and 17D, respectively. Data from 7 donors are presented as mean+SEM; * indicate p values<0,05 calculated by Student's t-test for paired samples (medium compared to stimulation with CpG ODN).

Example 15

IFN-α Secretion in "High Responders"

PBMC from 12 different donors were incubated with varying concentrations of ODN selected from a panel ODN including: ODN 2336 (SEQ ID NO:37), ODN 2334 (SEQ ID NO:36), ODN 2295 (SEQ ID NO:20), ODN 2255 (SEQ ID NO:16), ODN 2247 (SEQ ID NO:11), ODN 2216 (SEQ ID NO:7), and ODN 2006 (SEQ ID NO:147). Results from this study indicated that 6 of the donors could be classified as "high responders" in that the cells of these blood donors secreted more than 500 pg/ml (up to 7000 pg/ml) IFN-α after incubation with the selected ODN. A discrimination between "high" and "low" responders could be made because the cells of the 6 remaining donors only secreted amounts of IFN-α between 10 and 500 pg/ml. One reason for these differing results might come about from using buffy coats that are at least 24 h old. pDC, as the main cell type secreting IFN-α, survive only about 3 days in cell culture so that PBMC from buffy coats at least 24 hours old may contain very low numbers of this cell type.

IFN-α was measured in the above experiments by using an ELISA kit that recognizes all subtypes of IFN-α. Most other ELISA kits, in contrast, only measure IFN-α2B. Therefore, the amounts of IFN-α2B were compared against all IFN-α subtypes in several experiments to obtain information about possible differences in induction of different IFN-α subtypes. In addition, the amounts of IFN-α were compared against IFN-γ. Based on the results of this study, there was a correlation between the induction of IFN-α2B and all IFN-α subtypes. In contrast, however, ther was no clear correlation between IFN-α and IFN-γ.

Example 16

Induction of IFN-α Secretion by Select CpG ODN

Human PBMCs from a single donor were enriched for DC by going through the first step of the Miltenyi DC isolation kit which depletes monocytes, NK cells, and T cells, leaving mostly B cells, RBCs, and DCs. These were then incubated for two days in the presence of IL-3 (10 ng/ml) and various ODN at 6 µg/ml: ODN 1585 (SEQ ID NO:1), ODN 2022 (SEQ ID NO:2), ODN 2118 (SEQ ID NO:151), ODN 2184 (SEQ ID NO:3), ODN 2185 (SEQ ID NO:4), ODN 2192 (SEQ ID NO:5), ODN 2197 (SEQ ID NO:148), ODN 2198 (SEQ ID NO:149), ODN 2204 (SEQ ID NO:6), ODN 2216 (SEQ ID NO:7), or ODN 2217 (SEQ ID NO:8). In parallel samples, IFN-γ was added at 1000 U/ml. Supernatants were collected and analyzed in an ELISA specific for IFN-α.

Results. ODN induced IFN-α to varying degrees, with some augmentation by the addition of IFN-γ. Some of the ODN induced IFN-α to an exceptional degree (>50,000 pg/ml) even in the absence of added IFN-γ.

Example 17

Donor and Sequence Dependence of IFN-α Response to Various ODN

PBMC taken from four different donors were incubated for two day with a variety of ODN at 0.1 µg/ml. The panel of ODN included the following:

| Sequence | ODN | SEQ ID |
|---|---|---|
| ggGGTCAACGTTGAggggggG | ODN 1585 | SEQ ID NO:1 |
| ggggtcgtcgttttgggggg | ODN 2184 | SEQ ID NO:3 |
| tcgtcgttttgtcgttttgggggg | ODN 2185 | SEQ ID NO:4 |
| ggggtcgacgtcgagggggg | ODN 2192 | SEQ ID NO:5 |
| gmGGTCAACGTTGAgggmggG | ODN 2197 | SEQ ID NO:148 |
| ggGGAGTTCGTTGAggggggG | ODN 2198 | SEQ ID NO:149 |
| ggggtcatcgatgagggggg | ODN 2204 | SEQ ID NO:6 |
| ggGGGACGATCGTCggggggG | ODN 2216 | SEQ ID NO:7 |
| ggggtcgtacgacgggggg | ODN 2217 | SEQ ID NO:8 |
| ggggacgtcgacgtgggggg | ODN 2229 | SEQ ID NO:152 |
| ggggtcgttcgaacgagggggg | ODN 2237 | SEQ ID NO:153 |
| ggggacgttcgaacgtgggggg | ODN 2238 | SEQ ID NO:154 |
| ggGGGAGCATGCTGggggggG | ODN 2243 | SEQ ID NO:155 |
| ggGGGACGATATCGTCggggggG | ODN 2245 | SEQ ID NO:9 |
| ggGGGACGACGTCGTCggggggG | ODN 2246 | SEQ ID NO:10 |
| ggGGGACGAGCTCGTCggggggG | ODN 2247 | SEQ ID NO:11 |
| ggGGGACGTACGTCggggggG | ODN 2248 | SEQ ID NO:12 |
| ggGGGACGATCGTTggggggG | ODN 2252 | SEQ ID NO:13 |
| ggGGAACGATCGTCggggggG | ODN 2253 | SEQ ID NO:14 |
| ggGGGGACGATCGTCggggggG | ODN 2254 | SEQ ID NO:15 |
| ggGGGACGATCGTCGggggggG | ODN 2255 | SEQ ID NO:16 |
| ggGGGTCATCGATGAggggggG | ODN 2260 | SEQ ID NO:17 |
| ggGGGTCAACGTTGAggggggG | ODN 2261 | SEQ ID NO:156 |
| ggGGTCGTCGACGAggggggG | ODN 2293 | SEQ ID NO:18 |
| ggGGTCGTTCGAACGAggggggG | ODN 2294 | SEQ ID NO:19 |
| ggGGACGTTCGAACGTggggggG | ODN 2295 | SEQ ID NO:20 |
| ggGGAACGACGTCGTTggggggG | ODN 2297 | SEQ ID NO:21 |
| ggGGAACGTACGTCggggggG | ODN 2298 | SEQ ID NO:22 |
| ggGGAACGTACGTACGTTggggggG | ODN 2299 | SEQ ID NO:23 |
| ggGGTCACCGGTGAggggggG | ODN 2300 | SEQ ID NO:24 |
| ggGGTCGACGTACGTCGAggggggG | ODN 2301 | SEQ ID NO:25 |
| ggGGACCGGTACCGGTggggggG | ODN 2302 | SEQ ID NO:26 |
| ggGTCGACGTCGAggggggG | ODN 2303 | SEQ ID NO:27 |

| | | |
|---|---|---|
| ggGGTCGACGTCGagggg | ODN 2304 | SEQ ID NO:28 |
| ggGGAACGTTAACGTTggggG | ODN 2305 | SEQ ID NO:29 |
| ggGGACGTCGACGTggggG | ODN 2306 | SEQ ID NO:30 |
| ggGGGTCGTTCGTTggggG | ODN 2311 | SEQ ID NO:31 |
| ggGGGATGATTGTTggggG | ODN 2312 | SEQ ID NO:157 |
| ggGGGAZGATZGTTggggG | ODN 2313 | SEQ ID NO:158 |
| ggGGGAGCTAGCTTggggG | ODN 2314 | SEQ ID NO:159 |
| ggACGATCGTCGggggG | ODN 2328 | SEQ ID NO:32 |
| ggGTCGTCGACGAggggggG | ODN 2329 | SEQ ID NO:33 |
| ggTCGTCGACGAGggggggG | ODN 2330 | SEQ ID NO:34 |
| ggGTCGTCGTCGTGggggG | ODN 2331 | SEQ ID NO:160 |
| ggGGACGATCGTCGggggG | ODN 2332 | SEQ ID NO:35 |
| ggGGACGTCGTCGTggggG | ODN 2333 | SEQ ID NO:161 |
| ggGGTCGACGTCGACGTCGAGggggG | ODN 2334 | SEQ ID NO:36 |
| ggGGAACCGCGGTTggggG | ODN 2335 | SEQ ID NO:162 |

(Z in ODN 2313 represents 5-methyl cytosine)

Supernatants were collected and assayed for IFN-α by ELISA. In a parallel set of experiments PBMC taken from the same four different donors were incubated for two day with the dame panel of ODN at 1 µg/ml.

Results. The results for PBMC derived from the four donors and incubated with ODN at 0.1 µg/ml and with ODN at 1 µg/ml again showed dose and donor variation, with several ODN inducing IFN-α to levels of at least 5000 pg/ml and some inducing IFN-α to levels well in excess of 5000 pg/ml.

Those skilled in the art will recognize, or be able to ascertain using no more than routine experimentation, many equivalents to the specific embodiments of the invention described herein. Such equivalents are intended to be encompassed by the following claims.

The invention claimed is:

1. A chimeric nucleic acid comprising at least two immunostimulatory nucleic acids selected from the group consisting of CpG nucleic acids, T-rich nucleic acids, and poly-G nucleic acids, wherein at least one of the at least two immunostimulatory nucleic acids induces production of interferon alpha (IFN-α) from human peripheral blood mononuclear cells and has the sequence set forth by ggGGGACGATCGTCggggG (SEQ ID NO:7), wherein each lower case letter represents phosphorothioate linkage and each upper case letter indicates a phosphodiester linkage, and wherein at least one immunostimulatory nucleic acid is an oligonucleotide comprising a diol at either or both termini.

2. The chimeric nucleic acid of claim 1, wherein the diol is hexaethyleneglycol (HEG).

3. The chimeric nucleic acid of claim 1, wherein the diol is tetraethyleneglycol (TEG).

4. The chimeric nucleic acid of claim 1, wherein the chimeric nucleic acid induces production of type I IFN from human peripheral blood mononuclear cells but has minimal effects activating B cells.

5. A composition comprising the chimeric nucleic acid of claim 4 and a pharmaceutically acceptable excipient.

6. The composition of claim 5, further comprising an antigen.

7. The composition of claim 5, further comprising a microsphere.

8. A method of inducing an immune response in a subject, the method comprising administering to the subject a chimeric nucleic acid of claim 1 in an amount sufficient to induce an immune response in the subject.

9. A method of inducing an immune response in a subject, the method comprising administering to the subject a chimeric nucleic acid of claim 4 in an amount sufficient to induce an immune response in the subject.

\* \* \* \* \*

UNITED STATES PATENT AND TRADEMARK OFFICE
CERTIFICATE OF CORRECTION

PATENT NO. : 7,776,344 B2  Page 1 of 1
APPLICATION NO. : 11/179008
DATED : August 17, 2010
INVENTOR(S) : Gunther Hartmann et al.

It is certified that error appears in the above-identified patent and that said Letters Patent is hereby corrected as shown below:

At column 1, line 18, "government may have" should read --government has--.

Signed and Sealed this

Twenty-third Day of November, 2010

David J. Kappos
*Director of the United States Patent and Trademark Office*

SEQUENCE LISTING

<160> NUMBER OF SEQ ID NOS: 169

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 1
ggggtcaacg ttgagggggg                                                   20

<210> SEQ ID NO 2
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(24)
<223> OTHER INFORMATION: Backbone has phosphorothioate linkages.

<400> SEQUENCE: 2
tcgtcgtttt gtcgttttgt cgtt                                              24

<210> SEQ ID NO 3
<211> LENGTH: 20

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(20)
<223> OTHER INFORMATION: Backbone has phosphorothioate linkages.

<400> SEQUENCE: 3
ggggtcgtcg ttttggggggg                                              20

<210> SEQ ID NO 4
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(24)
<223> OTHER INFORMATION: Backbone has phosphorothioate linkages.

<400> SEQUENCE: 4
tcgtcgtttt gtcgttttgg gggg                                          24

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(20)
<223> OTHER INFORMATION: Backbone has phosphorothioate linkages.

<400> SEQUENCE: 5
ggggtcgacg tcgaggggggg                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(20)
<223> OTHER INFORMATION: Backbone has phosphorothioate linkages.

<400> SEQUENCE: 6
ggggtcatcg atgaggggggg                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
```

```
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 7
gggggacgat cgtcgggggg                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(20)
<223> OTHER INFORMATION: Backbone has phosphorothioate linkages.

<400> SEQUENCE: 8
gggggtcgta cgacgggggg                                                   20

<210> SEQ ID NO 9
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(16)
<223> OTHER INFORMATION: Backbone has phosphodiester linkages.
<220> FEATURE:
<221> NAME/KEY: misc_feature
<222> LOCATION: (17)...(21)
<223> OTHER INFORMATION: Backbone has phosphorothioate linkages.
<220> FEATURE:
<221> NAME/KEY: misc_feature
<222> LOCATION: (22)...(22)
<223> OTHER INFORMATION: Backbone has phosphodiester linkages.

<400> SEQUENCE: 9
gggggacgat atcgtcgggg gg                                                22

<210> SEQ ID NO 10
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(16)
<223> OTHER INFORMATION: Backbone has phosphodiester linkages.
<220> FEATURE:
<221> NAME/KEY: misc_feature
<222> LOCATION: (17)...(21)
<223> OTHER INFORMATION: Backbone has phosphorothioate linkages.
<220> FEATURE:
<221> NAME/KEY: misc_feature
<222> LOCATION: (22)...(22)
<223> OTHER INFORMATION: Backbone has phosphodiester linkages.

<400> SEQUENCE: 10
```

```
ggggacgac gtcgtcgggg gg                                              22
```

```
<210> SEQ ID NO 11
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(16)
<223> OTHER INFORMATION: Backbone has phosphodiester linkages.
<220> FEATURE:
<221> NAME/KEY: misc_feature
<222> LOCATION: (17)...(21)
<223> OTHER INFORMATION: Backbone has phosphorothioate linkages.
<220> FEATURE:
<221> NAME/KEY: misc_feature
<222> LOCATION: (22)...(22)
<223> OTHER INFORMATION: Backbone has phosphodiester linkages.

<400> SEQUENCE: 11 ggggacgag ctcgtcgggg gg                                              22
```

```
<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 12 ggggacgta cgtcgggggg                                                 20
```

```
<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(15)
<223> OTHER INFORMATION: Backbone has phosphodiester linkages.
<220> FEATURE:
<221> NAME/KEY: misc_feature
<222> LOCATION: (16)...(19)
<223> OTHER INFORMATION: Backbone has phosphorothioate linkages.
<220> FEATURE:
```

```
<221> NAME/KEY: misc_feature
<222> LOCATION: (20)...(20)
<223> OTHER INFORMATION: Backbone has phosphodiester linkages.

<400> SEQUENCE: 13
gggggacgat cgttgggggg                                                  20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(15)
<223> OTHER INFORMATION: Backbone has phosphodiester linkages.
<220> FEATURE:
<221> NAME/KEY: misc_feature
<222> LOCATION: (16)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 14
ggggaacgat cgtcgggggg                                                  20

<210> SEQ ID NO 15
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(15)
<223> OTHER INFORMATION: Backbone has phosphodiester linkages.
<220> FEATURE:
<221> NAME/KEY: misc_feature
<222> LOCATION: (16)...(20)
<223> OTHER INFORMATION: Backbone has phosphorothioate linkages.
<220> FEATURE:
<221> NAME/KEY: misc_feature
<222> LOCATION: (21)...(21)
<223> OTHER INFORMATION: Backbone has phosphodiester linkages.

<400> SEQUENCE: 15 gggggggacga tcgtcggggg g                                               21

<210> SEQ ID NO 16
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(15)
<223> OTHER INFORMATION: Backbone has phosphodiester linkages.
```

```
<220> FEATURE:
<221> NAME/KEY: misc_feature
<222> LOCATION: (16)...(20)
<223> OTHER INFORMATION: Backbone has phosphorothioate linkages.
<220> FEATURE:
<221> NAME/KEY: misc_feature
<222> LOCATION: (21)...(21)
<223> OTHER INFORMATION: Backbone has phosphodiester linkages.

<400> SEQUENCE: 16
gggggacgat cgtcgggggg g                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(15)
<223> OTHER INFORMATION: Backbone has phosphodiester linkages.
<220> FEATURE:
<221> NAME/KEY: misc_feature
<222> LOCATION: (16)...(20)
<223> OTHER INFORMATION: Backbone has phosphorothioate linkages.
<220> FEATURE:
<221> NAME/KEY: misc_feature
<222> LOCATION: (21)...(21)
<223> OTHER INFORMATION: Backbone has phosphodiester linkages.

<400> SEQUENCE: 17
gggggtcatc gatgaggggg g                                              21

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 18
ggggtcgtcg acgagggggg                                                20

<210> SEQ ID NO 19
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
```

<223> OTHER INFORMATION: Backbone has phosphorothioate linkages.
<220> FEATURE:
<221> NAME/KEY: misc_feature
<222> LOCATION: (3)...(16)
<223> OTHER INFORMATION: Backbone has phosphodiester linkages.
<220> FEATURE:
<221> NAME/KEY: misc_feature
<222> LOCATION: (17)...(21)
<223> OTHER INFORMATION: Backbone has phosphorothioate linkages.
<220> FEATURE:
<221> NAME/KEY: misc_feature
<222> LOCATION: (22)...(22)
<223> OTHER INFORMATION: Backbone has phosphodiester linkages.

<400> SEQUENCE: 19
ggggtcgttc gaacgagggg gg          22

<210> SEQ ID NO 20
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(16)
<223> OTHER INFORMATION: Backbone has phosphodiester linkages.
<220> FEATURE:
<221> NAME/KEY: misc_feature
<222> LOCATION: (17)...(21)
<223> OTHER INFORMATION: Backbone has phosphorothioate linkages.
<220> FEATURE:
<221> NAME/KEY: misc_feature
<222> LOCATION: (22)...(22)
<223> OTHER INFORMATION: Backbone has phosphodiester linkages.

<400> SEQUENCE: 20
ggggacgttc gaacgtgggg gg          22

<210> SEQ ID NO 21
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(16)
<223> OTHER INFORMATION: Backbone has phosphodiester linkages.
<220> FEATURE:
<221> NAME/KEY: misc_feature
<222> LOCATION: (17)...(21)
<223> OTHER INFORMATION: Backbone has phosphorothioate linkages.
<220> FEATURE:
<221> NAME/KEY: misc_feature
<222> LOCATION: (22)...(22)
<223> OTHER INFORMATION: Backbone has phosphodiester linkages.

<400> SEQUENCE: 21
ggggaacgac gtcgttgggg gg          22

<210> SEQ ID NO 22
<211> LENGTH: 20
<212> TYPE: DNA
<213> ORGANISM: Artificial Sequence

```
<220> FEATURE:
<223> OTHER INFORMATION: Synthetic Olignucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 22
ggggaacgta cgtcgggggg                                           20

<210> SEQ ID NO 23
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(18)
<223> OTHER INFORMATION: Backbone has phosphodiester linkages.
<220> FEATURE:
<221> NAME/KEY: misc_feature
<222> LOCATION: (19)...(23)
<223> OTHER INFORMATION: Backbone has phosphorothioate linkages.
<220> FEATURE:
<221> NAME/KEY: misc_feature
<222> LOCATION: (24)...(24)
<223> OTHER INFORMATION: Backbone has phosphodiester linkages.

<400> SEQUENCE: 23
ggggaacgta cgtacgttgg gggg                                      24

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 24
ggggtcaccg gtgagggggg                                           20
```

<210> SEQ ID NO 25
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(18)
<223> OTHER INFORMATION: Backbone has phosphodiester linkages.
<220> FEATURE:
<221> NAME/KEY: misc_feature
<222> LOCATION: (19)...(23)
<223> OTHER INFORMATION: Backbone has phosphorothioate linkages.
<220> FEATURE:
<221> NAME/KEY: misc_feature
<222> LOCATION: (24)...(24)
<223> OTHER INFORMATION: Backbone has phosphodiester linkages.

<400> SEQUENCE: 25
ggggtcgacg tacgtcgagg gggg                                24

<210> SEQ ID NO 26
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(16)
<223> OTHER INFORMATION: Backbone has phosphodiester linkages.
<220> FEATURE:
<221> NAME/KEY: misc_feature
<222> LOCATION: (17)...(21)
<223> OTHER INFORMATION: Backbone has phosphorothioate linkages.
<220> FEATURE:
<221> NAME/KEY: misc_feature
<222> LOCATION: (22)...(22)
<223> OTHER INFORMATION: Backbone has phosphodiester linkages.

<400> SEQUENCE: 26
ggggaccggt accggtgggg gg                                  22

<210> SEQ ID NO 27
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(13)
<223> OTHER INFORMATION: Backbone has phosphodiester linkages.
<220> FEATURE:
<221> NAME/KEY: misc_feature
<222> LOCATION: (14)...(18)
<223> OTHER INFORMATION: Backbone has phosphorothioate linkages.
<220> FEATURE:
<221> NAME/KEY: misc_feature
<222> LOCATION: (19)...(19)
<223> OTHER INFORMATION: Backbone has phosphodiester linkages.

-continued

<400> SEQUENCE: 27
gggtcgacgt cgagggggg                                                        19

<210> SEQ ID NO 28
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(13)
<223> OTHER INFORMATION: Backbone has phosphodiester linkages.
<220> FEATURE:
<221> NAME/KEY: misc_feature
<222> LOCATION: (14)...(18)
<223> OTHER INFORMATION: Backbone has phosphorothioate linkages.

<400> SEQUENCE: 28
ggggtcgacg tcgagggg                                                         18

<210> SEQ ID NO 29
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(16)
<223> OTHER INFORMATION: Backbone has phosphodiester linkages.
<220> FEATURE:
<221> NAME/KEY: misc_feature
<222> LOCATION: (17)...(21)
<223> OTHER INFORMATION: Backbone has phosphorothioate linkages.
<220> FEATURE:
<221> NAME/KEY: misc_feature
<222> LOCATION: (22)...(22)
<223> OTHER INFORMATION: Backbone has phosphodiester linkages.

<400> SEQUENCE: 29
ggggaacgtt aacgttgggg gg                                                    22

<210> SEQ ID NO 30
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(18)
<223> OTHER INFORMATION: Backbone has phosphorothioate linkages.
<220> FEATURE:
<221> NAME/KEY: misc_feature
<222> LOCATION: (19)...(19)

<223> OTHER INFORMATION: Backbone has phosphodiester linkages.

<400> SEQUENCE: 30
ggggacgtcg acgtgggggg					19

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 31
gggggtcgtt cgttggggggg					20

<210> SEQ ID NO 32
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(13)
<223> OTHER INFORMATION: Backbone has phosphodiester linkages.
<220> FEATURE:
<221> NAME/KEY: misc_feature
<222> LOCATION: (14)...(18)
<223> OTHER INFORMATION: Backbone has phosphorothioate linkages.
<220> FEATURE:
<221> NAME/KEY: misc_feature
<222> LOCATION: (19)...(19)
<223> OTHER INFORMATION: Backbone has phosphodiester linkages.

<400> SEQUENCE: 32
gggacgatcg tcggggggg					19

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(13)
<223> OTHER INFORMATION: Backbone has phosphodiester linkages.
<220> FEATURE:
<221> NAME/KEY: misc_feature
<222> LOCATION: (14)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 33
gggtcgtcga cgagggggggg                                              20

<210> SEQ ID NO 34
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(13)
<223> OTHER INFORMATION: Backbone has phosphodiester linkages.
<220> FEATURE:
<221> NAME/KEY: misc_feature
<222> LOCATION: (14)...(18)
<223> OTHER INFORMATION: Backbone has phosphorothioate linkages.
<220> FEATURE:
<221> NAME/KEY: misc_feature
<222> LOCATION: (19)...(19)
<223> OTHER INFORMATION: Backbone has phosphodiester linkages.

<400> SEQUENCE: 34
ggtcgtcgac gagggggg                                                 19

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 35
ggggacgatc gtcggggggg                                               20

<210> SEQ ID NO 36
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:

```
<221> NAME/KEY: misc_feature
<222> LOCATION: (3)...(21)
<223> OTHER INFORMATION: Backbone has phosphodiester linkages.
<220> FEATURE:
<221> NAME/KEY: misc_feature
<222> LOCATION: (22)...(26)
<223> OTHER INFORMATION: Backbone has phosphorothioate linkages.
<220> FEATURE:
<221> NAME/KEY: misc_feature
<222> LOCATION: (27)...(27)
<223> OTHER INFORMATION: Backbone has phosphodiester linkages.

<400> SEQUENCE: 36
ggggtcgacg tcgacgtcga ggggggg                                         27

<210> SEQ ID NO 37
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(15)
<223> OTHER INFORMATION: Backbone has phosphodiester linkages.
<220> FEATURE:
<221> NAME/KEY: misc_feature
<222> LOCATION: (16)...(20)
<223> OTHER INFORMATION: Backbone has phosphorothioate linkages.
<220> FEATURE:
<221> NAME/KEY: misc_feature
<222> LOCATION: (21)...(21)
<223> OTHER INFORMATION: Backbone has phosphodiester linkages.

<400> SEQUENCE: 37
ggggacgacg tcgtgggggg g                                               21

<210> SEQ ID NO 38
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 38 aacgttct                                                               8

<210> SEQ ID NO 39
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 39
accatggacg aactgtttcc cctc                                            24

<210> SEQ ID NO 40
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 40
accatggacg acctgtttcc cctc                                            24
```

```
<210> SEQ ID NO 41
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 41
accatggacg agctgtttcc cctc                                              24

<210> SEQ ID NO 42
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 42
accatggacg atctgtttcc cctc                                              24

<210> SEQ ID NO 43
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 43
accatggacg gtctgtttcc cctc                                              24

<210> SEQ ID NO 44
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 44
accatggacg tactgtttcc cctc                                              24

<210> SEQ ID NO 45
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 45
accatggacg ttctgtttcc cctc                                              24

<210> SEQ ID NO 46
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 46
agctatgacg ttccaagg                                                     18

<210> SEQ ID NO 47
<211> LENGTH: 20
<212> TYPE: DNA
<213> ORGANISM: Artificial Sequence
<220> FEATURE:
```

```
<223> OTHER INFORMATION: Synthetic Oligonucleotide

<400> SEQUENCE: 47
ataggaggtc caacgttctc                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
atcgactctc gaacgttctc                                               20

<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
atcgactctc gagcgttctc                                               20

<210> SEQ ID NO 50
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 50
atgacgttcc tgacgtt                                                  17

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
atggaaggtc caacgttctc                                               20

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
atggaaggtc cagcgttctc                                               20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
atggactctc cagcgttctc                                               20
```

```
<210> SEQ ID NO 54
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 54
atggaggctc catcgttctc                                                  20

<210> SEQ ID NO 55
<211> LENGTH: 7
<212> TYPE: DNA
<213> ORGANISM: Artificial Sequence
<220> FEATURE:
<223> OTHER INFORMATION: Synthetic Oligonucleotide

<400> SEQUENCE: 55 caacgtt                                                                 7

<210> SEQ ID NO 56
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 56
cacgttgagg ggcat                                                       15

<210> SEQ ID NO 57
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 57 ccaacgtt                                                                8

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 58
gagaacgatg gaccttccat                                                  20

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 59
gagaacgctc cagcactgat                                                  20

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 60
gagaacgctc gaccttccat                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 61
gagaacgctc gaccttcgat                                              20

<210> SEQ ID NO 62
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 62
gagaacgctg gaccttccat                                              20

<210> SEQ ID NO 63
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 63
gcatgacgtt gagct                                                   15

<210> SEQ ID NO 64
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 64
gcgtgcgttg tcgttgtcgt t                                            21

<210> SEQ ID NO 65
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 65
gctagacgtt agcgt                                                   15

<210> SEQ ID NO 66
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 66
gctagacgtt agtgt                                                   15

<210> SEQ ID NO 67
<211> LENGTH: 15
```

```
<212> TYPE: DNA
<213> ORGANISM: Artificial Sequence
<220> FEATURE:
<223> OTHER INFORMATION: Synthetic Oligonucleotide

<400> SEQUENCE: 67
gctagatgtt agcgt                                                    15

<210> SEQ ID NO 68
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 68
ggggtcaacg ttgacgggg                                                19

<210> SEQ ID NO 69
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 69
ggggtcagtc gtgacgggg                                                19

<210> SEQ ID NO 70
<211> LENGTH: 6
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_difference
<222> LOCATION: (5)...(5)
<223> OTHER INFORMATION: y = t/u or c

<400> SEQUENCE: 70 gtcgyt                                                              6

<210> SEQ ID NO 71
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 71 tcaacgtc                                                            8

<210> SEQ ID NO 72
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 72 tcaacgtt                                                            8

<210> SEQ ID NO 73
<211> LENGTH: 8
<212> TYPE: DNA
<213> ORGANISM: Artificial Sequence
<220> FEATURE:
```

```
<223> OTHER INFORMATION: Synthetic Oligonucleotide

<400> SEQUENCE: 73 tcagcgct                                                              8

<210> SEQ ID NO 74
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 74
tcagcgtgcg cc                                                        12

<210> SEQ ID NO 75
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 75 tcatcgat                                                              8

<210> SEQ ID NO 76
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 76
tccacgacgt tttcgacgtt                                                20

<210> SEQ ID NO 77
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 77
tccataacgt tcctgatgct                                                20

<210> SEQ ID NO 78
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 78
tccatagcgt tcctagcgtt                                                20

<210> SEQ ID NO 79
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 79
tccatcacgt gcctgatgct                                                20
```

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 80
tccatgacgg tcctgatgct                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 81
tccatgacgt ccctgatgct                                               20

<210> SEQ ID NO 82
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 82
tccatgacgt gcctgatgct                                               20

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 83
tccatgacgt tcctgacgtt                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 84
tccatgacgt tcctgatgct                                               20

<210> SEQ ID NO 85
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 85
tccatgccgg tcctgatgct                                               20

<210> SEQ ID NO 86
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 86
tccatgcgtg cgtgcgtttt                                               20

<210> SEQ ID NO 87
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 87
tccatgcgtt gcgttgcgtt                                               20

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 88
tccatggcgg tcctgatgct                                               20

<210> SEQ ID NO 89
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 89
tccatgtcga tcctgatgct                                               20

<210> SEQ ID NO 90
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 90
tccatgtcgc tcctgatgct                                               20

<210> SEQ ID NO 91
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 91
tccatgtcgg tcctgacgca                                               20

<210> SEQ ID NO 92
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 92
tccatgtcgg tcctgatgct                                               20

<210> SEQ ID NO 93
<211> LENGTH: 20
```

```
<212> TYPE: DNA
<213> ORGANISM: Artificial Sequence
<220> FEATURE:
<223> OTHER INFORMATION: Synthetic Oligonucleotide

<400> SEQUENCE: 93
tccatgtcgg tcctgctgat                                              20

<210> SEQ ID NO 94
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 94
tccatgtcgt ccctgatgct                                              20

<210> SEQ ID NO 95
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 95
tccatgtcgt tcctgtcgtt                                              20

<210> SEQ ID NO 96
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 96
tccatgtcgt ttttgtcgtt                                              20

<210> SEQ ID NO 97
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 97
tcctgacgtt cctgacgtt                                               19

<210> SEQ ID NO 98
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 98
tcctgtcgtt cctgtcgtt                                               19

<210> SEQ ID NO 99
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 99
```
tcctgtcgtt ccttgtcgtt                                              20

<210> SEQ ID NO 100
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 100
tcctgtcgtt ttttgtcgtt                                              20

<210> SEQ ID NO 101
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 101
tccttgtcgt tcctgtcgtt                                              20

<210> SEQ ID NO 102
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 102
tcgtcgctgt ctccccttct t                                            21

<210> SEQ ID NO 103
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 103
tcgtcgctgt ctgcccttct t                                            21

<210> SEQ ID NO 104
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 104
tcgtcgctgt tgtcgtttct t                                            21

<210> SEQ ID NO 105
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 105
tcgtcgtcgt cgtt                                                    14

<210> SEQ ID NO 106
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 106
tcgtcgttgt cgttgtcgtt                                              20

<210> SEQ ID NO 107
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 107
tcgtcgttgt cgttttgtcg tt                                           22

<210> SEQ ID NO 108
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 108
tcgtcgtttt gtcgttttgt cgtt                                         24

<210> SEQ ID NO 109
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 109
tctcccagcg ggcgcat                                                 17

<210> SEQ ID NO 110
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 110
tctcccagcg tgcgccat                                                18

<210> SEQ ID NO 111
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 111 tcttcgaa                                                            8

<210> SEQ ID NO 112
<211> LENGTH: 8
<212> TYPE: DNA
<213> ORGANISM: Artificial Sequence
<220> FEATURE:
<223> OTHER INFORMATION: Synthetic Oligonucleotide

<400> SEQUENCE: 112 tcttcgat                                                            8
```

```
<210> SEQ ID NO 113
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 113
tgtcgttgtc gtt                                                          13

<210> SEQ ID NO 114
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 114
tgtcgttgtc gttgtcgtt                                                    19

<210> SEQ ID NO 115
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 115
tgtcgttgtc gttgtcgttg tcgtt                                             25

<210> SEQ ID NO 116
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 116
tgtcgtttgt cgtttgtcgt t                                                 21

<210> SEQ ID NO 117
<211> LENGTH: 7
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_difference
<222> LOCATION: (6)...(6)
<223> OTHER INFORMATION: y = t/u or c

<400> SEQUENCE: 117 tgtcgyt                                                                 7

<210> SEQ ID NO 118
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 118
atggaaggtc caaggggctc                                                   20

<210> SEQ ID NO 119
<211> LENGTH: 20
```

<212> TYPE: DNA
<213> ORGANISM: Artificial Sequence
<220> FEATURE:
<223> OTHER INFORMATION: Synthetic Oligonucleotide

<400> SEQUENCE: 119
atggaaggtc cagggggctc                                               20

<210> SEQ ID NO 120
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 120
atggaaggtc cggggttctc                                               20

<210> SEQ ID NO 121
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 121
atggactctc cggggttctc                                               20

<210> SEQ ID NO 122
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 122
atggactctg gaggggctc                                                20

<210> SEQ ID NO 123
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 123
atggactctg gagggtctc                                                20

<210> SEQ ID NO 124
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 124
atggactctg ggggttctc                                                20

<210> SEQ ID NO 125
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 125

-continued atggaggctc catggggctc                                              20

<210> SEQ ID NO 126
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 126
gagaaggggc cagcactgat                                              20

<210> SEQ ID NO 127
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 127
gagaaggggg gaccttccat                                              20

<210> SEQ ID NO 128
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 128
gagaaggggg gaccttggat                                              20

<210> SEQ ID NO 129
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 129
gcatgagggg gagct                                                   15

<210> SEQ ID NO 130
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 130
gctagaggga gtgt                                                    14

<210> SEQ ID NO 131
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 131
gctagagggg agggt                                                   15

<210> SEQ ID NO 132
<211> LENGTH: 15
<212> TYPE: DNA
<213> ORGANISM: Artificial Sequence

```
<220> FEATURE:
<223> OTHER INFORMATION: Synthetic Oligonucleotide

<400> SEQUENCE: 132
gctagatgtt agggg                                                    15

<210> SEQ ID NO 133
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 133
gggggacgat cgtcggsgggg                                              20

<210> SEQ ID NO 134
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 134
gggggggggg gggggggggg                                               20

<210> SEQ ID NO 135
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 135
ggggtcaacg ttgaggggggg                                              20

<210> SEQ ID NO 136
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 136
ggggtcgacg tcgaggggggg                                              20

<210> SEQ ID NO 137
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 137
tccatcgggg gcctgatgct                                               20

<210> SEQ ID NO 138
<211> LENGTH: 20
<212> TYPE: DNA
<213> ORGANISM: Artificial Sequence
<220> FEATURE:
<223> OTHER INFORMATION: Synthetic Olignucleotide

<400> SEQUENCE: 138
tccatgaggg gcctgatgct                                               20
```

```
<210> SEQ ID NO 139
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 139
tccatgcggg tgggatgct                                              20

<210> SEQ ID NO 140
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 140 tccatgggggtcctgatgct                                              20

<210> SEQ ID NO 141
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 141
tccatggggt ccctgatgct                                             20

<210> SEQ ID NO 142
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 142
tccatggggt gcctgatgct                                             20

<210> SEQ ID NO 143
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 143
tccatggggt tcctgatgct                                             20

<210> SEQ ID NO 144
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 144
tccatgtggg gcctgatgct                                             20

<210> SEQ ID NO 145
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 145
tccatgtggg gcctgctgat                                                  20

<210> SEQ ID NO 146
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 146
tccatgtggg tggggatgct                                                  20

<210> SEQ ID NO 147
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(24)
<223> OTHER INFORMATION: Backbone has phosphorothioate linkages.

<400> SEQUENCE: 147
tcgtcgtttt gtcgttttgt cgtt                                             24

<210> SEQ ID NO 148
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(20)
<223> OTHER INFORMATION: Backbone has phosphorothioate linkages.
<220> FEATURE:
<221> NAME/KEY: misc_feature
<222> LOCATION: (21)...(21)
<223> OTHER INFORMATION: Backbone has phosphodiester linkages.
<220> FEATURE:
<221> NAME/KEY: misc_difference
<222> LOCATION: (2)...(2)
<223> OTHER INFORMATION: m = a or c
<220> FEATURE:
<221> NAME/KEY: misc_difference
<222> LOCATION: (18)...(18)
<223> OTHER INFORMATION: m = a or c

<400> SEQUENCE: 148
gmggtcaacg ttgagggmgg g                                                21

<210> SEQ ID NO 149
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)

```
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 149 gggggagttcg ttgagggggg                                              20

<210> SEQ ID NO 150
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 150
gggggagcat gctcgggggg                                               20

<210> SEQ ID NO 151
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 151
ggggtcaagc ttgagggggg                                               20

<210> SEQ ID NO 152
<211> LENGTH: 20
<212> TYPE: DNA
<213> ORGANISM: Artificial Sequence
```

<220> FEATURE:
<223> OTHER INFORMATION: Synthetic Oligonucleotide
<220> FEATURE:
<221> NAME/KEY: misc_feature
<222> LOCATION: (1)...(20)
<223> OTHER INFORMATION: Backbone has phosphorothioate linkages.

<400> SEQUENCE: 152
ggggacgtcg acgtggggggg                                                    20

<210> SEQ ID NO 153
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(22)
<223> OTHER INFORMATION: Backbone has phosphorothioate linkages.

<400> SEQUENCE: 153
ggggtcgttc gaacgagggg gg                                                  22

<210> SEQ ID NO 154
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(22)
<223> OTHER INFORMATION: Backbone has phosphorothioate linkages.

<400> SEQUENCE: 154
ggggacgttc gaacgtgggg gg                                                  22

<210> SEQ ID NO 155
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphorothioate linkages.

<400> SEQUENCE: 155
gggggagcat gctgggggggg                                                    20

<210> SEQ ID NO 156
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:

```
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(15)
<223> OTHER INFORMATION: Backbone has phosphodiester linkages.
<220> FEATURE:
<221> NAME/KEY: misc_feature
<222> LOCATION: (16)...(20)
<223> OTHER INFORMATION: Backbone has phosphorothioate linkages.
<220> FEATURE:
<221> NAME/KEY: misc_feature
<222> LOCATION: (21)...(21)
<223> OTHER INFORMATION: Backbone has phosphodiester linkages.

<400> SEQUENCE: 156
gggggtcaac gttgagggggg g                                              21

<210> SEQ ID NO 157
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 157
gggggatgat tgttgggggg                                                 20

<210> SEQ ID NO 158
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.
<220> FEATURE:
<221> NAME/KEY: modified_base
<222> LOCATION: (7)...(7)
<223> OTHER INFORMATION: n = 5- methylcytidine
<220> FEATURE:
<221> NAME/KEY: modified_base
<222> LOCATION: (10)...(10)
<223> OTHER INFORMATION: n = 5-methylcytidine
```

<400> SEQUENCE: 158
gggggangan tgttgggggg                                                                      20

<210> SEQ ID NO 159
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 159
gggggagcta gcttgggggg                                                                      20

<210> SEQ ID NO 160
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 160
gggtcgtcgt cgtgggggg                                                                       20

<210> SEQ ID NO 161
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)

```
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 161
ggggacgtcg tcgtgggggg                                              20

<210> SEQ ID NO 162
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(2)
<223> OTHER INFORMATION: Backbone has phosphorothioate linkages.
<220> FEATURE:
<221> NAME/KEY: misc_feature
<222> LOCATION: (3)...(14)
<223> OTHER INFORMATION: Backbone has phosphodiester linkages.
<220> FEATURE:
<221> NAME/KEY: misc_feature
<222> LOCATION: (15)...(19)
<223> OTHER INFORMATION: Backbone has phosphorothioate linkages.
<220> FEATURE:
<221> NAME/KEY: misc_feature
<222> LOCATION: (20)...(20)
<223> OTHER INFORMATION: Backbone has phosphodiester linkages.

<400> SEQUENCE: 162
ggggaaccgc ggttgggggg                                              20

<210> SEQ ID NO 163
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 163
accgatgacg tcgccggtga cggcaccacg acggccaccg tgctg                  45

<210> SEQ ID NO 164
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 164
accgatgacg tcgccggtga cggcaccacg                                   30

<210> SEQ ID NO 165
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 165
gggggggggg ggaacgttgg gggggggggg                                   30

<210> SEQ ID NO 166
<211> LENGTH: 9
<212> TYPE: PRT
<213> ORGANISM: Artificial Sequence
```

```
<220> FEATURE:
<223> OTHER INFORMATION: Synthetic Peptide

<400> SEQUENCE: 166

Gly Ile Leu Gly Phe Val Phe Thr Leu
1               5

<210> SEQ ID NO 167
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 167

Glu Leu Ala Gly Ile Gly Ile Leu Thr Val
1               5                   10

<210> SEQ ID NO 168
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(23)
<223> OTHER INFORMATION: Each n is any nucleotide and optionally may
      be missing.

<400> SEQUENCE: 168
gggnnnnnnn nnnnnnnnnn nnnggg                                          26

<210> SEQ ID NO 169
<211> LENGTH: 49
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (4)..(23)
<223> OTHER INFORMATION: Each n is any nucleotide and optionally may
      be missing.
<220> FEATURE:
<221> NAME/KEY: misc_feature
<222> LOCATION: (27)..(46)
<223> OTHER INFORMATION: Each n is any nucleotide and optionally may
      be missing.

<400> SEQUENCE: 169
gggnnnnnnn nnnnnnnnnn nnngggnnnn nnnnnnnnnn nnnnnnggg                 49
```